United States Patent [19]
Chin et al.

[11] Patent Number: 5,810,770
[45] Date of Patent: Sep. 22, 1998

[54] FLUID MANAGEMENT PUMP SYSTEM FOR SURGICAL PROCEDURES

[75] Inventors: Sing Fatt Chin, Fremont; Charles Nelson, Pleasanton; John Nguyen, San Jose; Heber Saravia, San Francisco, all of Calif.; Brett Naglreiter, Hallandale, Fla.

[73] Assignee: Stryker Corporation, Kalamazoo, Mich.

[21] Appl. No.: 763,368

[22] Filed: Dec. 13, 1996

[51] Int. Cl.⁶ ........................ A61M 31/00
[52] U.S. Cl. ........................ 604/65
[58] Field of Search .............. 604/30, 31, 49, 604/50, 65, 67, 66; 128/DIG. 12, DIG. 13

[56] References Cited

U.S. PATENT DOCUMENTS

| | | |
|---|---|---|
| 4,061,142 | 12/1977 | Tuttle . |
| 4,276,023 | 6/1981 | Phillips et al. . |
| 4,509,507 | 4/1985 | Yabe . |
| 4,650,462 | 3/1987 | DeSatnick et al. . |
| 4,655,752 | 4/1987 | Honkanen et al. . |
| 4,820,265 | 4/1989 | DeSatnick et al. . |
| 4,904,168 | 2/1990 | Cavoto et al. . |
| 4,935,005 | 6/1990 | Haines . |
| 4,951,977 | 8/1990 | Shutt . |
| 5,017,059 | 5/1991 | Davis . |
| 5,037,386 | 8/1991 | Marcus et al. . |
| 5,065,783 | 11/1991 | Ogle, II . |
| 5,098,387 | 3/1992 | Wiest et al. . |
| 5,201,714 | 4/1993 | Gentelia et al. . |
| 5,399,160 | 3/1995 | Dunberger et al. . |
| 5,403,277 | 4/1995 | Dodge et al. . |
| 5,456,673 | 10/1995 | Ziegler et al. . |
| 5,484,402 | 1/1996 | Saravia et al. . |
| 5,487,649 | 1/1996 | Dorsey, III et al. . |

FOREIGN PATENT DOCUMENTS

| | | |
|---|---|---|
| 0 529 902A2 | 3/1993 | European Pat. Off. . |
| WO 93/22560 | 11/1993 | WIPO . |

OTHER PUBLICATIONS

*3M Fluid Control System,* 1992, 3 pages.
American Hydro–Surgical, *Installation/Operating Instructions For "Quick Disconnect" Probe Tips,* 2 pages, 1996.
Davol, *Arthro Flo Irrigator,* 4 pages, 1996.

*Primary Examiner*—Michael Buiz
*Assistant Examiner*—Manuel Mendez
*Attorney, Agent, or Firm*—Flynn, Thiel, Boutell & Tanis, P.C.

[57] ABSTRACT

A fluid management pump system (30) for supplying sterile solution to a surgical site. The system includes an inflow tube (42) for supplying sterile solution to the surgical site. The solution is forced through the inflow tube by a pump (40). Fluid is drained from the surgical site in order to maintain the pressure at the site through an outflow tube (44). Both the inflow and outflow tubes are attached to a cassette (52). The cassette is mounted to a control unit (50). Internal to the cassette are pinch valves (54, 56) for controlling fluid flow through, respectively, the inflow and outflow tubes. The open/closed states of the inflow and outflow tubes are controlled by solenoids (58, 60) internal to the control unit that act on the pinch valves. The control unit actuates the solenoids and supplies the energization current to the pump based on operator entered commands and indication that the pressure at the surgical site. A column of air representative of liquid-state fluid pressure at the surgical site is supplied to the control unit through the cassette.

24 Claims, 26 Drawing Sheets

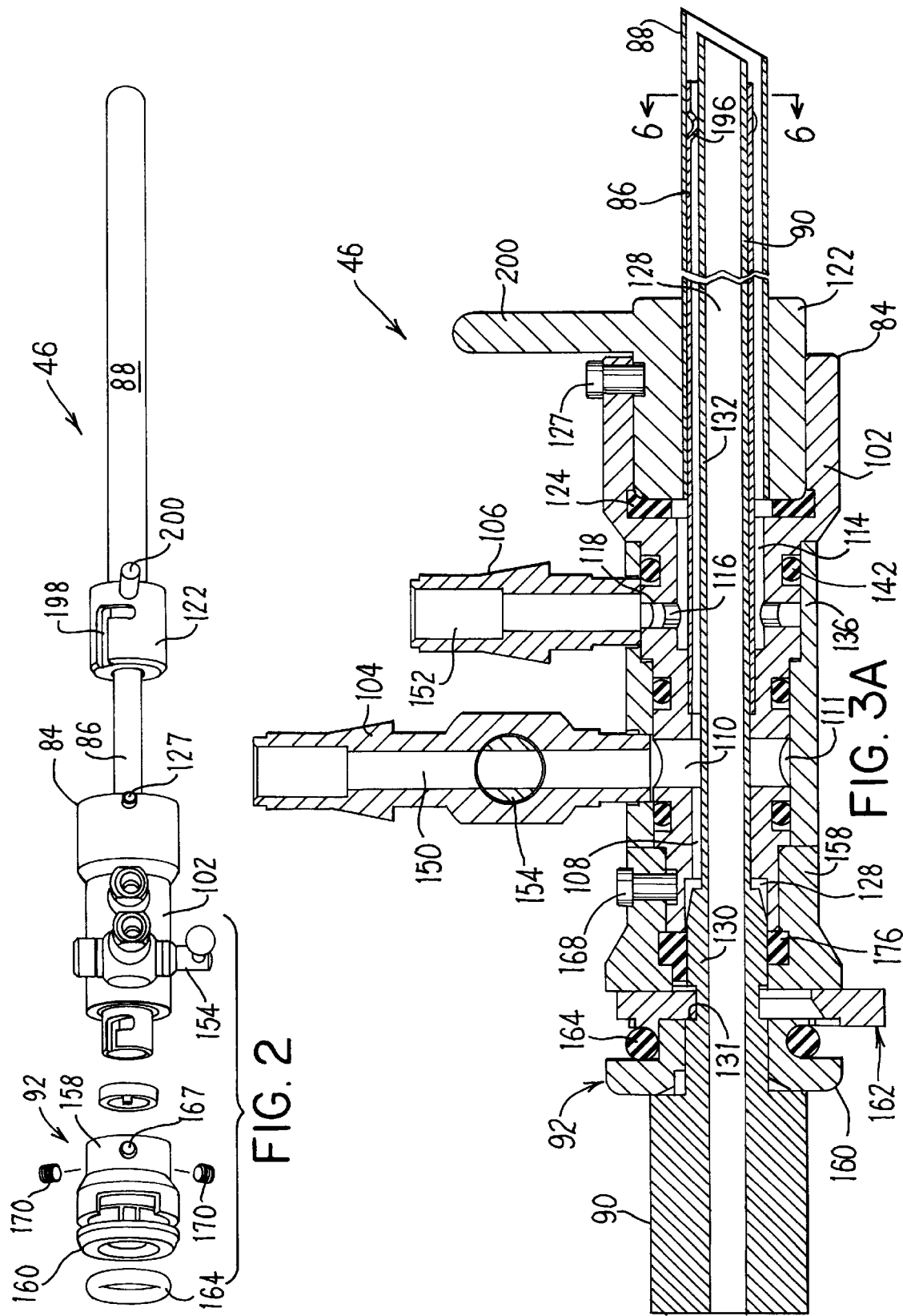

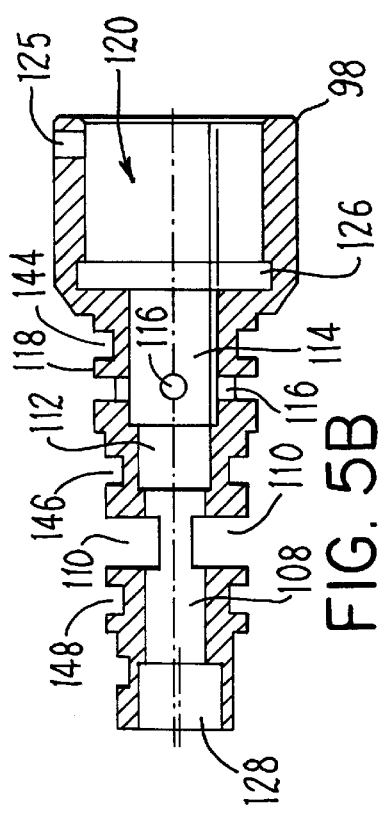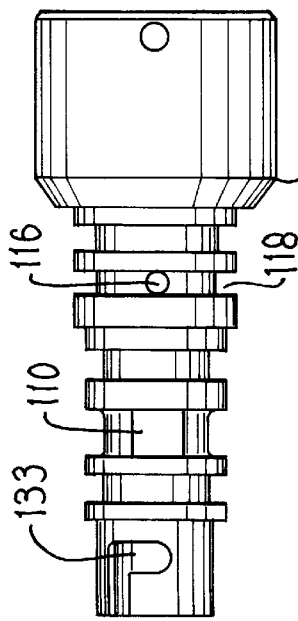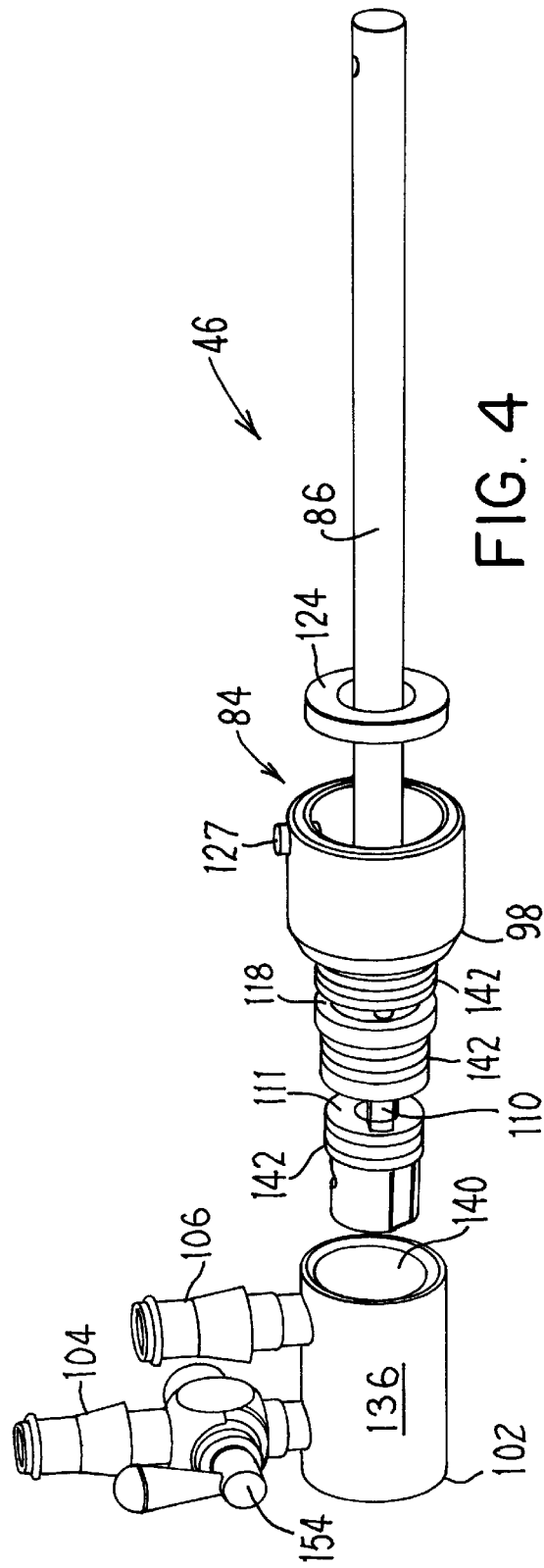

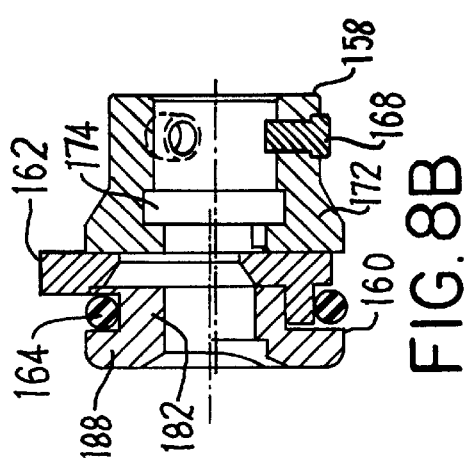
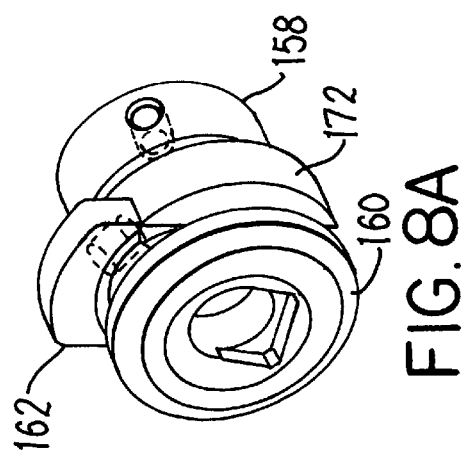
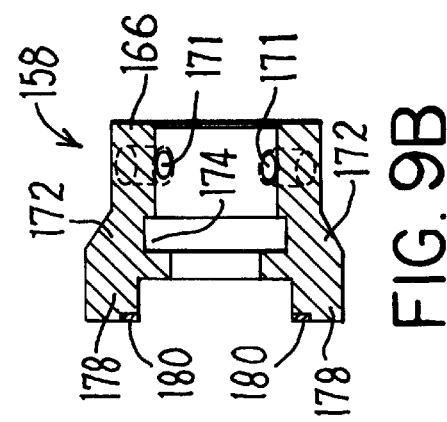
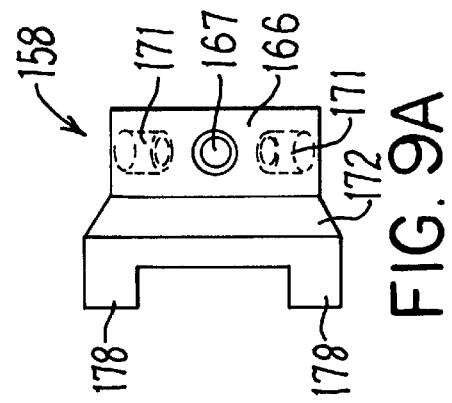
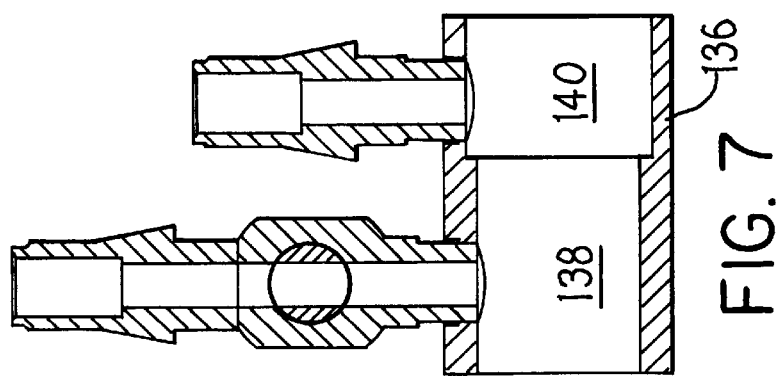

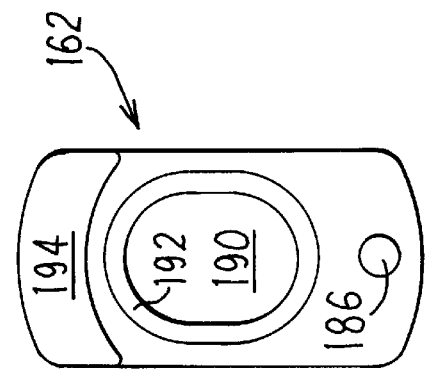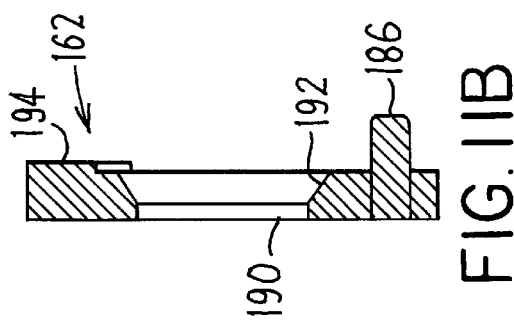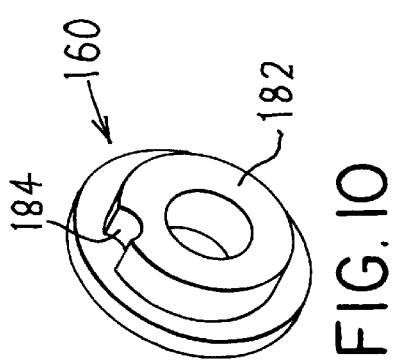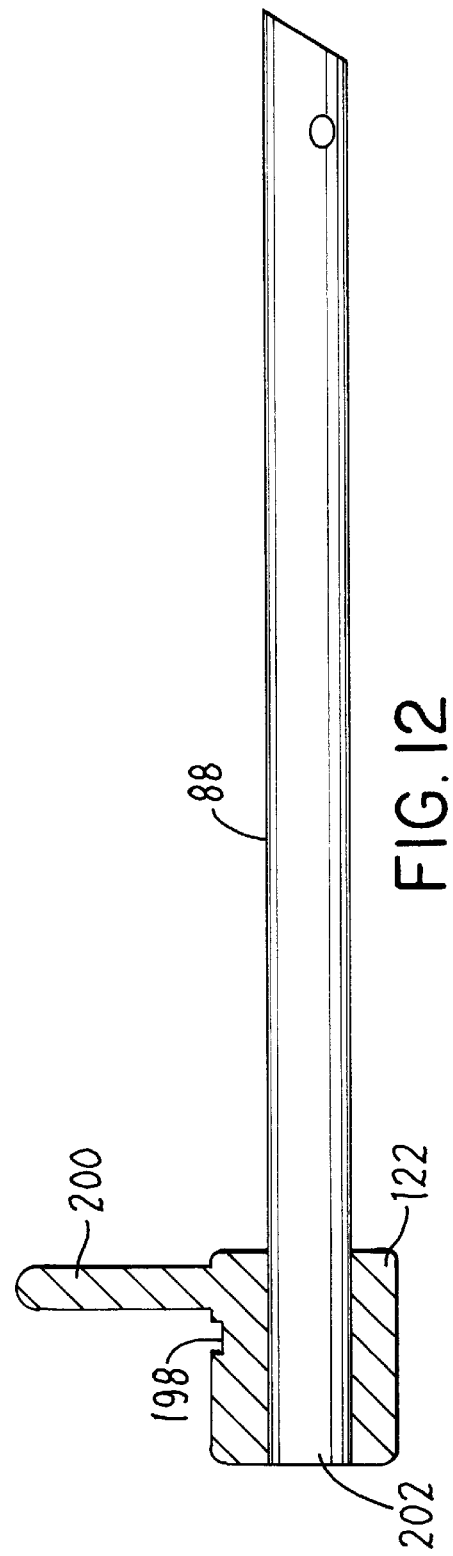

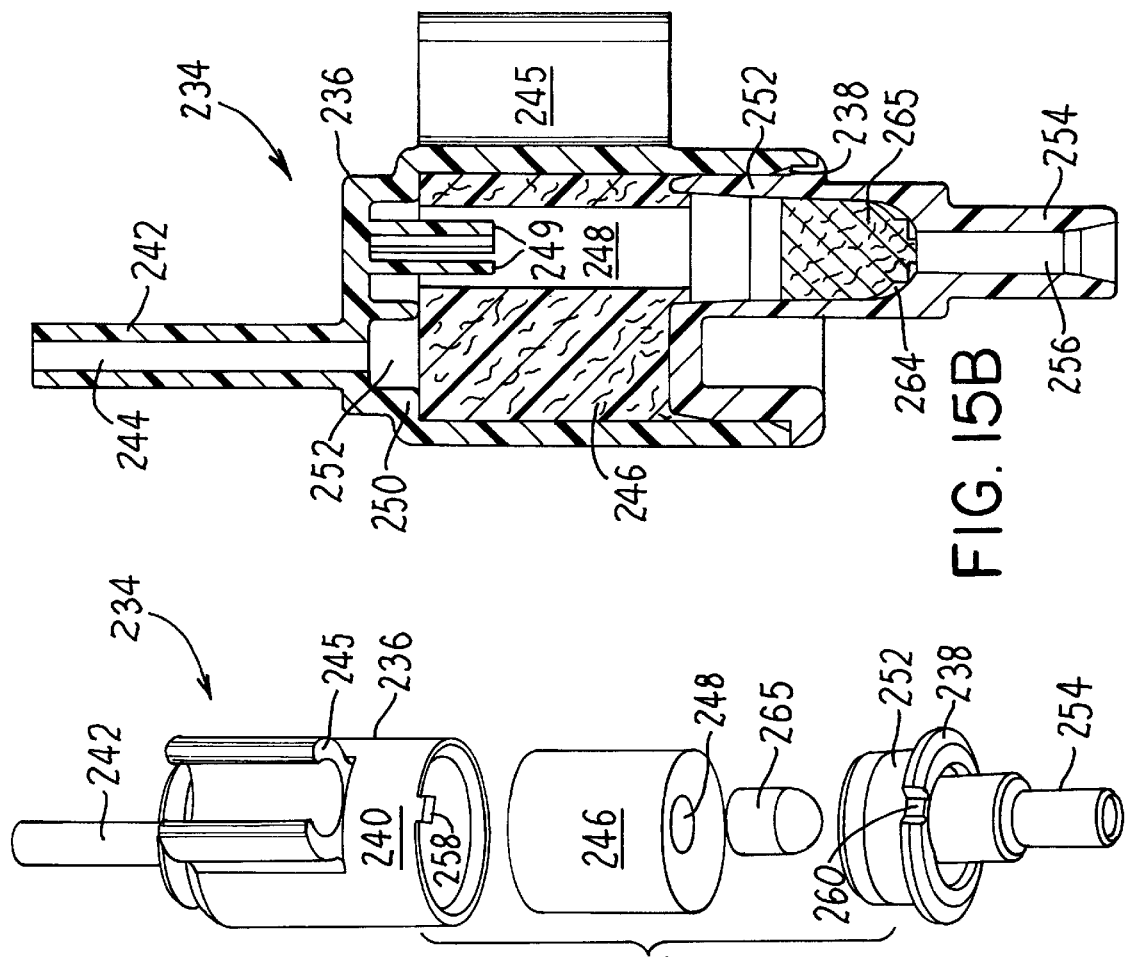
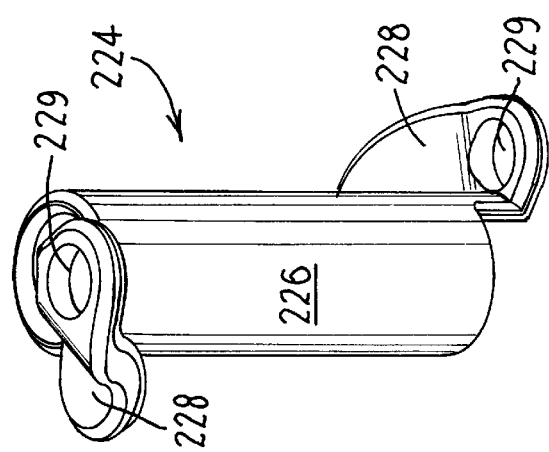
FIG. 15B
FIG. 15A
FIG. 14

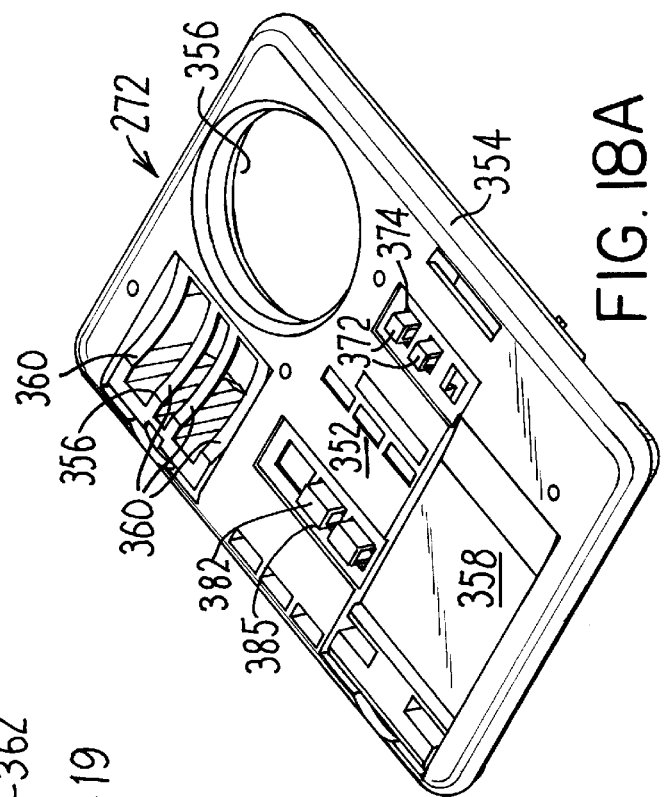
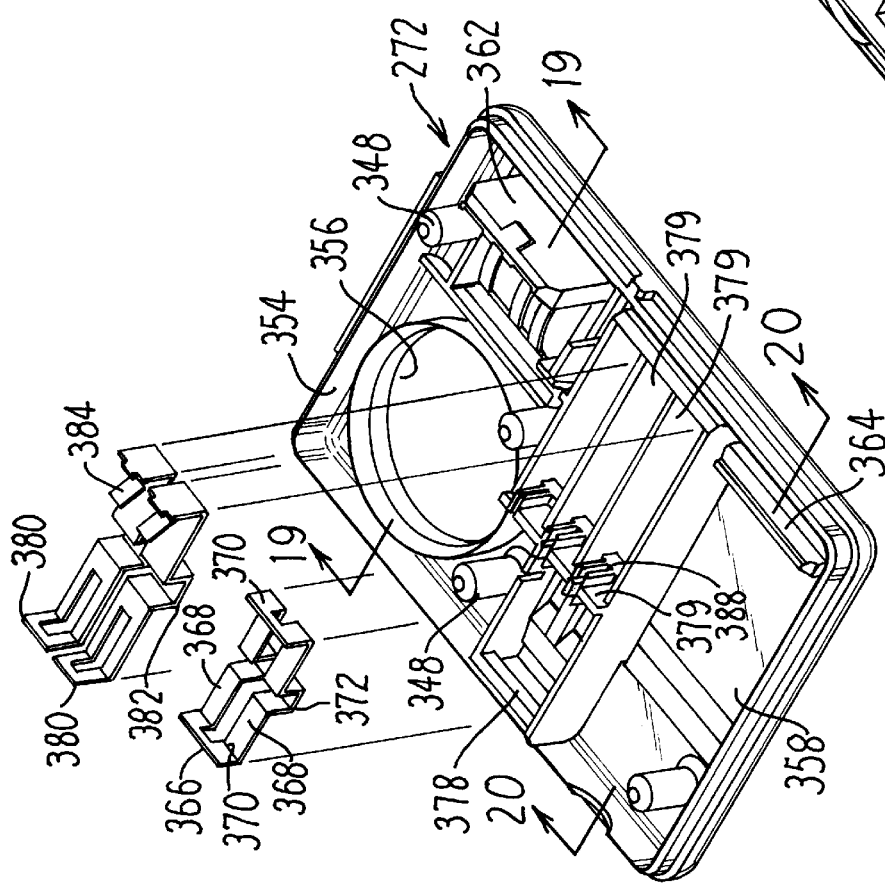

FLUID MANAGEMENT PUMP SYSTEM FOR SURGICAL PROCEDURES

FIELD OF THE INVENTION

This invention relates generally to a fluid management pump system for supplying fluid to a surgical site and, more particularly, to a fluid management pump system that is relatively compact in size and includes components that are readily coupled together to assemble the system.

BACKGROUND OF THE INVENTION

Fluid management pump systems are employed during surgical procedures to introduce sterile solution into surgical sites. One such procedure in which a fluid management pump is employed during an endoscopic surgical procedure. In endoscopic surgery, an endoscope is inserted into the body at the site where the surgical procedure is to be performed. The endoscope is a surgical instrument that provides a view of the portion of the body in which it is inserted. Other surgical instruments are placed in the body at the surgical site. The surgeon views the surgical site through the endoscope in order to manipulate the other surgical instruments. The development of endoscopes and their companion surgical instruments has made it possible to perform minimally invasive surgery that eliminates the need to make large incisions to gain access to the surgical site. Instead, during endoscopic surgery, small openings, called portals, are formed in the patient. An advantage of performing endoscopic surgery is that since the portions of the body that are cut open are minimized, the portions of the body that need to heel after the surgery are likewise reduced. Still another advantage of endoscopic surgery is that it exposes less of the interior tissue of the patient's body to the open environment. This minimal opening of the patient's body lessens the extent to which the patient's internal tissue and organs are open to infection.

The ability to perform endoscopic surgery is enhanced by the development of fluid management pumps. A fluid management pump is designed to pump a sterile solution into the enclosed portion of the body at which the endoscopic surgical procedure is being performed. This solution expands and separates the tissue at the surgical site so as to increase both the field of view of the surgical site and the space available to the surgeon for manipulating the surgical instruments. One type of endoscopic surgery in which fluid management pumps have proven especially useful is in arthroscopic surgery. In arthroscopic surgery, a specially designed endoscope, called arthroscope, is employed to examine inter-bone joints and the ligaments and muscles that connect the bones. A fluid management pump is often employed in arthroscopic surgery to expand the space between the bones and adjacent soft tissue in order to increase the field in which the surgeon can perform the intended surgical procedure. Fluid management pumps are, during arthroscopic surgery, used to increase the surgical view of the joints that form an elbow, a knee, a wrist, or an ankle. Fluid management pumps are used both in endoscope surgery and in other surgical procedures to remove debris generated by the procedure.

A fluid management pump system includes a number of different components. There is the pump unit that supplies the motive force for pumping the sterile solution through an inflow tube into the surgical site. The actuation of the pump is regulated by a control unit. The control unit receives as input signals both surgeon entered commands and an indication of the liquid-state fluid pressure at the surgical site.

Still another component of a fluid management pump system is the tube set. The tube set includes the fluid communication tubes that are connected between the pump unit, the control unit and the surgical site in the patient which is infused with the distention fluid. The tube set includes the previously described inflow tube through which the solution is introduced into the surgical site. There is also an outflow tube through which the solution and any waste material carried therewith is removed from the surgical site. Fluid flow from the site is typically regulated by a valve integral with the control unit that selectively opens and closes the inflow and outflow tubes. The tube set also includes a pressure feedback tube. The pressure feedback tube provides a fluid communication path between the surgical site and the control unit so that a pressure transducer integral with the control unit can monitor the fluid pressure at the surgical site. The pressure signal the transducer supplies is used by the control unit to regulate the actuation of the pump unit and to control the open/closed state of the fluid inflow and outflow tubes.

Most fluid management pump systems further include cannulae that are inserted into the patient. The cannulae function as the actual fluid communication paths between the surgical site and the tubes forming the tube set. In order to minimize the number of portals that need to be formed in the patient, it is current practice to provide a single cannula that provides both the fluid communication into the body for the inflow tube and the pressure feedback tube and that functions as the guide bore through which the endoscope is inserted. These particular cannulae are called pressure sensing cannulae.

While current fluid management pump systems have proven useful devices for distending endoscopic surgical sites, there are limitations associated with their use. Typically, a significant amount of time needs to be spent coupling the individual tubes forming the tube set to the motor, the pressure transducer and the associated valves. The reason large amounts of time are required is because the tubing itself must be kept sterile. Consequently, each time a fluid management pump system is used with a new patient a whole new tube set must be installed. This necessitates ensuring that each tube is properly connected to the complementary part of the pump unit and/or the control unit. It is also necessary to provide a sterile barrier between the pressure feedback tube and the complementary transducer in the control unit.

Moreover, many fluid management pump systems are provided with pumps that, in addition to a motor and a fluid impeller, include a gear assembly connected between the motor and the impeller. The actuation of this gear assembly inevitably adds to the noise level of the surgical suite in which these fluid management pump systems are employed.

While currently available pressure sensing cannulae have served to reduce the number of portals that need to be cut in a patient's body, there are some limitations in their effectiveness. For example, many pressure sensing cannulae are provided with complicated locking mechanisms for releasably securing the complementary endoscope in the cannula. Consequently, during the installation and removal of the endoscope, the surgeon is required to devote some time and concentration to the steps required to first lock the endoscope in place and then unlock it. Furthermore, it has proven difficult to provide pressure sensing cannulae that while having a relatively small overall diameter are designed to both provide a guide bore for the endoscope and provide conduits through which both sufficient amounts of sterile solution can be supplied to the surgical site and the pressure of the fluid at the site can be accurately sensed.

It is still another goal when providing a fluid management pump system to design the control unit so that it is both as compact and as light weight as possible. The reason it is desirable to keep the size and weight of the control unit as low as possible is that it is desirable to mount the control unit on an intravenous pole so that it can easily be placed near the patient and easily moved away therefrom. This goal has, however, proved difficult to reach. A significant reason for this is that the environment in which these control unit are used, surgical suites, are electrically very noisy environments. Consequently, there has been a tendency to design these control units with complex shielding structures so as minimize the affect ambient electrical noise has on their internal signal processing.

SUMMARY OF THE INVENTION

This invention relates to an improved fluid management pump system that is formed out of a set of components that are readily assembled together to form a working system. Still other features of this invention are that it includes: control unit that generates a relatively small amount of sonic and electrical noise; a pressure sensing cannula configured to facilitate the making of relatively accurate pressure measurements at the surgical site; that it has a control unit capable of detecting small changes in fluid pressure at the surgical site relatively accurately; and that the control unit is both sufficiently compact in size and light in weight that it can be easily suspended from a support pole in the surgical suite.

BRIEF DESCRIPTION OF THE DRAWINGS

The invention is pointed out with particularity in the claims. The above and further features of the invention may be better understood by reference to the following description taken in conjunction with the accompanying drawings in which:

FIG. 2 is partially disassembled view of the pressure sensing cannula employed of this fluid management pump system;

FIG. 4 is a partially disassembled view of the main body subassembly of the pressure sensing cannula;

FIGS. 5A and 5B are, respectively, side and cross sectional views of the cannula body of the pressure sensing cannula;

FIG. 7 is a cross sectional view of the housing of the main body subassembly of the pressure sensing cannula;

FIGS. 8A and 8B are, respectively, perspective and cross sectional views of the cap of the pressure sensing cannula;

FIGS. 9A and 9B are, respectively, side and cross sectional views of the cap insert of the cap of FIGS. 8A and 8B;

FIG. 10 is a rear perspective view of the cap cover of the cap of FIGS. 8A and 8B;

FIGS. 11A and 11B are, respectively, plan and cross sectional views of the cap lock of the cap of FIGS. 8A and 8B;

FIG. 12 is a cross sectional view of the outer sleeve and sleeve adapter of the pressure sensing cannula;

FIG. 14 is a perspective view of the barrel around which a portion of the pressure line inlet tube is wrapped;

FIGS. 15A and 15B are, respectively, exploded and cross sectional views of the air-water separator of the tube set;

FIGS. 18A and 18B are views, respectively, of the outside and inside of the cover of the cassette, wherein FIG. 18B further illustrates some of the components seated in the cover;

FIGS. 31A, 31B, 31C, 31D, 31E and 31F are arranged together to form a schematic diagram of the components internal to the control unit that control the actuation the pump and the valves of the fluid management system.

DETAILED DESCRIPTION

Figure 1:
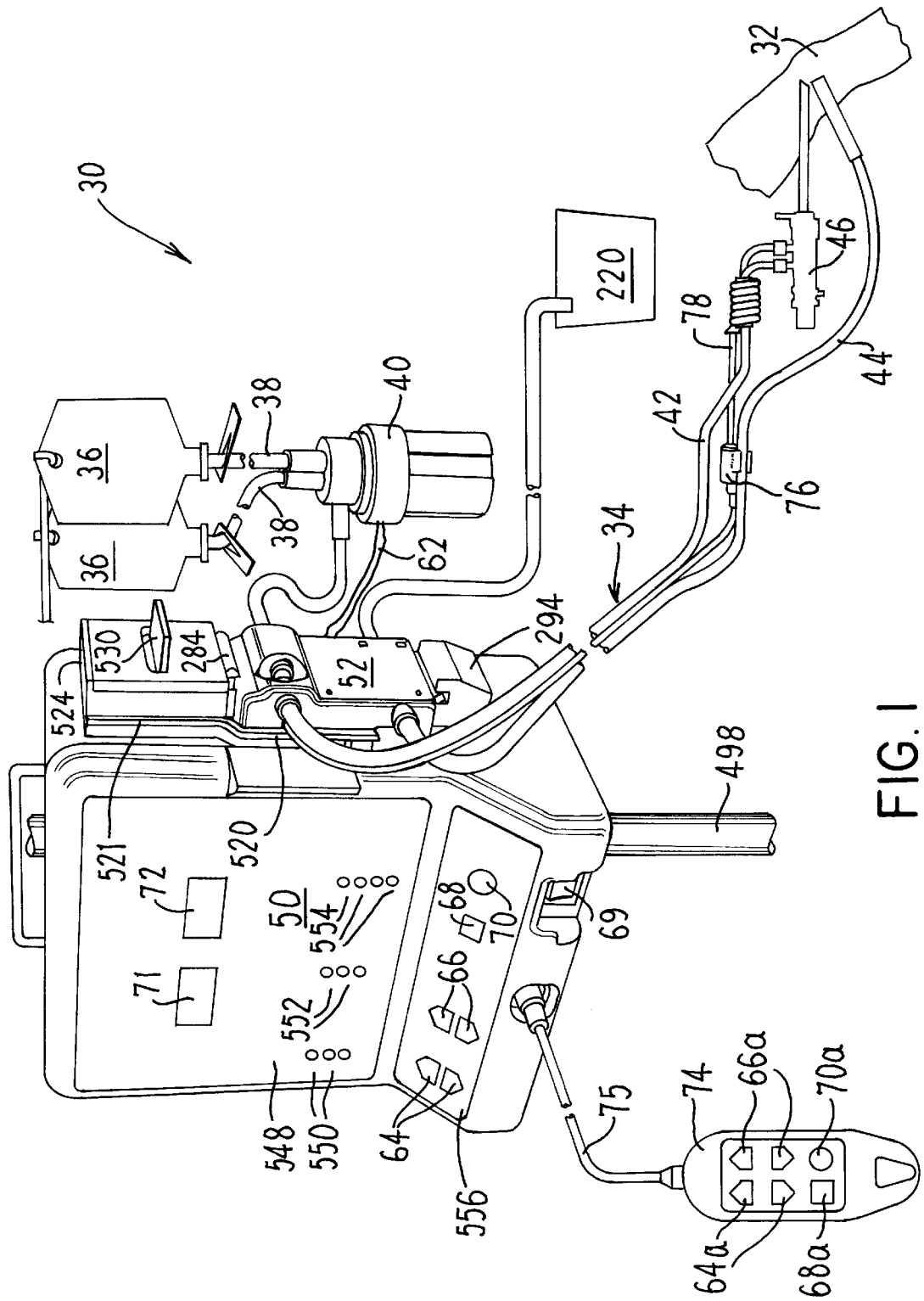
FIG. 1 depicts the basic components of the fluid management pump system of this invention.

FIG. 1 depicts a fluid management pump system 30 of this invention that is employed to supply a sterile distention solution to a surgical site within a body and, more particularly, the joint capsule of a knee 32. The fluid management pump system 30 includes a tube set 34 through which sterile solution from containers 36 is selectively introduced into the knee 32 and drained from the knee. The tube set 34 includes a pair of fluid inlet tubes 38 each of which is connected to a separate one of the containers 36. The fluid inlet tubes 38 serve as input lines to a centrifugal pump 40 that serves as the pump unit of the fluid management pump system 30. The output liquid flow from pump 40 is applied to an inflow tube 42 that is part of the tube set 34. The sterile solution that is forced through the inflow tube 42 is introduced into the surgical site through a pressure sensing cannula 46. The tube set 34 further includes an outflow tube 44 through which fluid including any waste carried thereby, is selectively drained from the surgical site.

The actuation of the pump 40 and the control of the fluid flow through inflow and outflow tubes 42 and 44, respectively, are regulated by a control unit 50. In the fluid management pump system 30 of this invention, the tube set 34 includes a cassette 52 through which both the inflow and outflow tubes 42 and 44, respectively, extend. The cassette 52 is removably mounted to one side of the control unit 50. Internal to the cassette 52 are pinch valves 54 and 56 (FIGS. 19 and 20, respectively) which, respectively open and close inflow tube 42 and outflow tube 44. The open/closed states of the inflow and outflow tubes 42 and 44, respectively, are controlled by solenoids 58 and 60, respectively, (FIG. 29) that are internal to the control unit 50. It will also be seen that in the illustrated version of the invention, a power cable 62 through which energization signals are applied to the pump 40 extends from the cassette 52 to the pump. The control unit 50 selectively generates the energization signals required to actuate the pump 40 and applies the signals to the pump through cassette 52.

Control unit 50 actuates pump 40 and regulates the flow of distention solution to and from the surgical site based on surgeon entered commands and fluid pressure at the surgical site. In the depicted version of the invention, the front face of the control unit 50 is provided with a first set of buttons 64 that allow the surgeon to control the rate at which the sterile solution is introduced into the surgical site through the inflow tube 42. A second set of buttons 66 allow the surgeon to set the fluid pressure at the surgical site. A single lavage button 68 allows the surgeon to set the pump 40 to operate at a lavage rate so as to flush the surgical site. The depicted control unit 50 also has a basic power on/off switch 69 and a run/stop button 70. The run/stop button 70 is depressed to regulate the basic starting and stopping of the system without changing the flow rate and the pressure settings. Control unit 50 also includes a first display 71 for indicating the surgeon set pressure for the surgical site and a second display 72 on which the actual pressure is presented.

A portable hand control 74 is connected to the control unit 50 by a flexible cable 75. Hand control 74 is provided with buttons 64a, 66a, 68a, and 70 that allow medical personnel to enter the same commands that are entered through buttons 64–70. The portability of hand control 74 allows the surgeon to enter commands for controlling the operation of the fluid management pump system 30 without having to actuate the buttons of the control unit 50.

Figure 28:
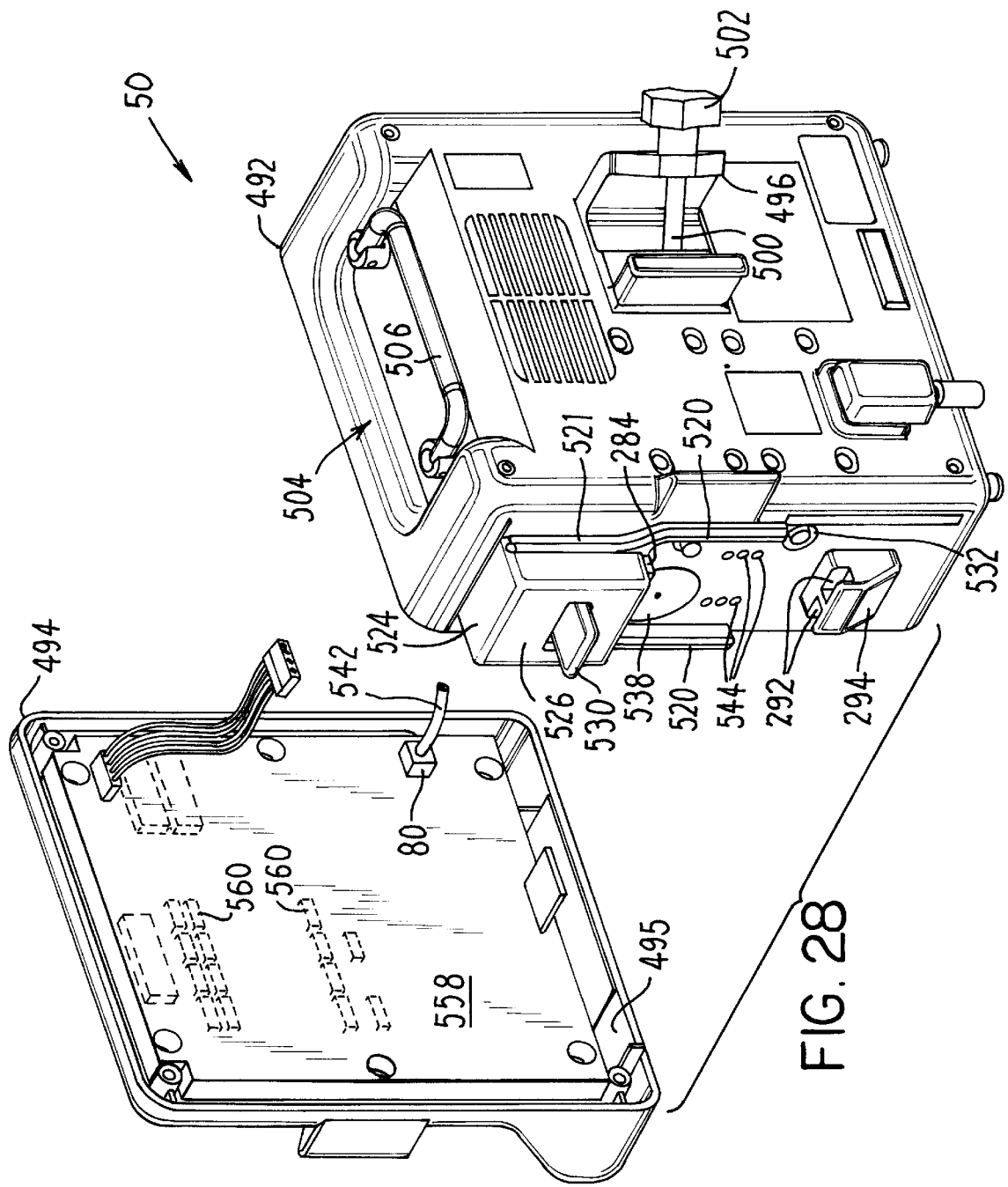
FIG. 28 is a perspective partially exploded view of the control unit of the fluid management pump system of this invention.

The control unit 50 monitors the fluid pressure of the surgical site over a pressure sensing assembly 76 that is also part of the tube set 34. One end of pressure sensing assembly 76 is connected to the pressure sensing cannula 46. The opposed end of the pressure sensing assembly 76 terminates inside the cassette 52. Between the pressure sensing cannula 46 and the cassette 52, pressure sensing assembly 76 includes a pressure line inlet tube 78. Normally, a water column that extends from the pressure sensing cannula 46 has a head that terminates in the pressure line inlet tube 78. Internal to the control unit 50 is a pressure transducer 80 (FIG. 28). The cassette 52 provides a gas tight seal between the pressure sensing assembly 76 and a pressure transducer 80. During normal operation of the fluid management pump system 30, the head of the water column in the pressure line inlet tube 78 changes position as a function of the fluid pressure at the surgical site. The change in position of the head of the water column causes the air pressure in the portion of the pressure sensing assembly 76 connected to the transducer 80 to change. This change in air pressure is monitored by transducer 80 so as to serve as a measure of the liquid-state fluid pressure at the surgical site. As will be described hereinafter, based on the fluid pressure at the surgical site, the control unit 50 both actuates the pump 40 and opens and closes the inflow and outflow tubes 42 and 44, respectively.

FIGS. 2 and 3A illustrate the basic components of the pressure sensing cannula 46. The cannula 46 includes a main body subassembly 84 from which a cannula tube 86 extends. An outer sleeve 88 is attached to the main body subassembly 84 so extend over the cannula tube 86. The cannula tube 86 and the outer sleeve 88 are the portions of the cannula 46 that are inserted into the portal formed in the patient so as to terminate at the surgical site. The cannula tube 86 serves as both the guide bore in which an endoscope 90 is placed and the conduit through which sterile solution is introduced into the surgical site. The elongated space between the outer wall of the cannula tube 86 and the inside wall of the outer sleeve 88 serve as the conduit through which the column of fluid from the surgical site is directed to the pressure line inlet tube 78. The pressure sensing cannula 46 also includes a cap 92 that is attached to the end of the main body subassembly 84 opposite the end from which the cannula tube 86 extends. Cap 92 is provided with a locking mechanism for holding the endoscope 90 in place. In the following description of the pressure sensing cannula 46, it shall hereinafter be understood that in reference to the cannula and the components thereof, "proximal" shall mean a location or position towards the exposed end of the cap 92 and "distal" shall mean a location or position towards the exposed ends of the cannula tube 86 and the outer sleeve 88 that are positioned at the surgical site.

The main body subassembly 84 of cannula 46, as seen by reference to FIG. 4, includes both a cannula body 98 and a housing 102 that is rotatably fitted over the cannula body. The cannula body 98 serves as the component to which the cannula tube 86 is attached and the socket in which the outer sleeve 88 is releasably secured. The cannula body 98 also defines the base of the fluid conduits formed in the cannula 46. The housing 102 is provided with a stopcock 104 and an outlet stud 106 to which the inflow tube 42 and pressure line inlet tube 78 are, respectively, attached. The cannula body 98, as best seen by reference to FIGS. 3A, 3B, 5A and 5B, is generally circular in profile though the individual sections thereof are of varying diameter. The cannula body 98 is further formed so that the interior thereof has a set of bores and counterbores of varying diameters that extend between ends of the cannula body. The smallest diameter bore formed in the cannula body is the inflow bore 108. The inflow bore 108 starts from a position spaced inwardly from the proximal end of the cannula body 98 and terminates at a position distal from the portion of the cannula body that is subtended by the inflow stopcock 104. The portion of the cannula body that defines inflow bore 108 is further shaped to include two diametrically opposed inflow ports 110 that extend from the outer surface of the cannula body to inflow port 108. Inflow ports 110 are axially centered in the plane in which the center axis of the inflow stopcock 104. The inflow ports open into a shallow annular groove formed around the outside of the cannula body 98. Groove 111 and inflow ports 110 thus serve as fluid communication paths through which the sterile solution flowing through inflow stopcock 104 is introduced into inflow bore 108.

Cannula body 98 is formed with a tube bore 112 that is immediately distal from the inflow bore 108 and is concentric with the inflow bore. The cannula body 108 is formed so that the tube bore 112 has a diameter that is equal to the outside diameter of the cannula tube 86; this diameter is slightly greater than the diameter of the inflow bore 108. The proximal end of the cannula tube 86 is secured in the tube bore 112 such that the outer surface of the tube 86 is secured to the inner wall of the cannula body 98 that defines the bore 112. As best seen by reference to FIG. 3B, the cannula tube 86 is formed so as to have an inside diameter equal to the diameter of inflow bore 108. Thus, the conduit through which the sterile solution flows is smooth walled from the location where the fluid is introduced into the cannula body 108 through the inflow ports 110.

A pressure feedback bore 114 is formed in the cannula body 98 so as to be located immediately adjacent and distally positioned relative to the tube bore 112. The pressure feedback bore 114 is both formed concentrically with and has a diameter greater than the tube bore 112. Thus, the section of the cannula tube 86 that extends through feedback bore 114 is equidistantly spaced from the inner walls of the cannula body 98 that define the fluid feedback bore 114. The portion of the cannula body 98 forming the pressure feedback bore 114 is formed to define four equidistantly spaced fluid feedback ports 116 that extend from the outside of the cannula body to the pressure feedback bore 114. The fluid feedback ports 116 are axially located in the plane in which the center axis of the outlet stud 106 is located. This portion of the cannula body 98 is further formed with an annular groove 118 along the outer surface of the body into which the fluid feedback ports 116 open. Consequently, the fluid from the surgical site that flows back towards the control unit 50 for feedback purposes flows from the pressure feedback bore 114, through the fluid feedback ports 116 and the groove 118 and into the outlet stud 106.

The distal end of the cannula body 98, which is located adjacent the end of the portion of the cannula body that forms the pressure feedback bore 114, is the largest diameter portion of the cannula body. This end of the cannula body 98 is shaped to define a counterbore, an outer tube socket 120, in which the outer sleeve 88 is seated. More particularly, outer tube socket 120 is sized to receive both the outer sleeve 88 and sleeve adapter 122 that is seated over the proximal end of the outer sleeve 88. A ring-shaped outer tube seal 124 is seated in the base of the outer tube socket 120, the portion of the socket adjacent the pressure feedback bore 114. More particularly, the outer perimeter of outer tube seal 124 is seated in a counterbore 126 that is formed contiguously with the outer tube socket 120 and is located immediately distal from the portion of the cannula body 98 that defines the pressure feedback bore 114. Outer tube seal 124 serves as a barrier to prevent the feedback liquid in the pressure feedback bore 114 from leaking out of the distal end of the cannula body 98. Both the outer tube socket 120 and associated counterbore 126 are concentric with the pressure feedback bore 114. A lock pin 127 extends laterally through a lateral bore 125 the distal end of the cannula body 98 into the socket 120. Lock pin 127 facilitates the securement of the outer sleeve 88 to the cannula body 98 as will be described hereinafter.

The proximal end of the cannula body 98 is formed with a counterbore that functions as an endoscope receiving socket 128. More particularly, the endoscope receiving socket 128 extends from the proximal end of the cannula body 98 to the inflow bore 108. The endoscope receiving socket 128 has a diameter that is greater than that of the inflow bore 108; the diameter of the endoscope receiving socket is sized so that a shoulder section 130 of the endoscope 90 can be snugly fitted therein. The cannula body 98 is further shaped so that the endoscope receiving socket 128 is not coaxially aligned with the center axis of the inflow bore 108 and the bores commonly aligned therewith. Rather, the center axis of the endoscope receiving socket 128 is displaced from the axis of the inflow bore 108. In some versions of this invention, this displacement is between 0.010 and 0.025 inches, in more preferred versions of the invention, this displacement is approximately 0.015 inches. As a result of the axial displacement of the endoscope receiving socket 128, when the endoscope 90 is seated in the pressure sensing cannula 46, the elongated tube-like main body 132 of the endoscope is not centered along the associated cannula tube 86. Instead, as seen best in FIGS. 3A and 6, the main body 132 of the endoscope is disposed against an arcuate section of the inside wall of the cannula tube 86.

By reference to FIG. 5A, it can also be seen that the proximal end on the cannula body 98 is formed so as to have an L-shaped slot 133 in the outer surface thereof. Slot 133 extends rearwardly from the proximal end of the cannula body 98 and subtends an arc that extends approximately 45° around the cannula body. As will be described hereinafter, slot 133 is provided to facilitate the proper seating alignment of the cap 92 onto the cannula body 98.

Figure 3B:
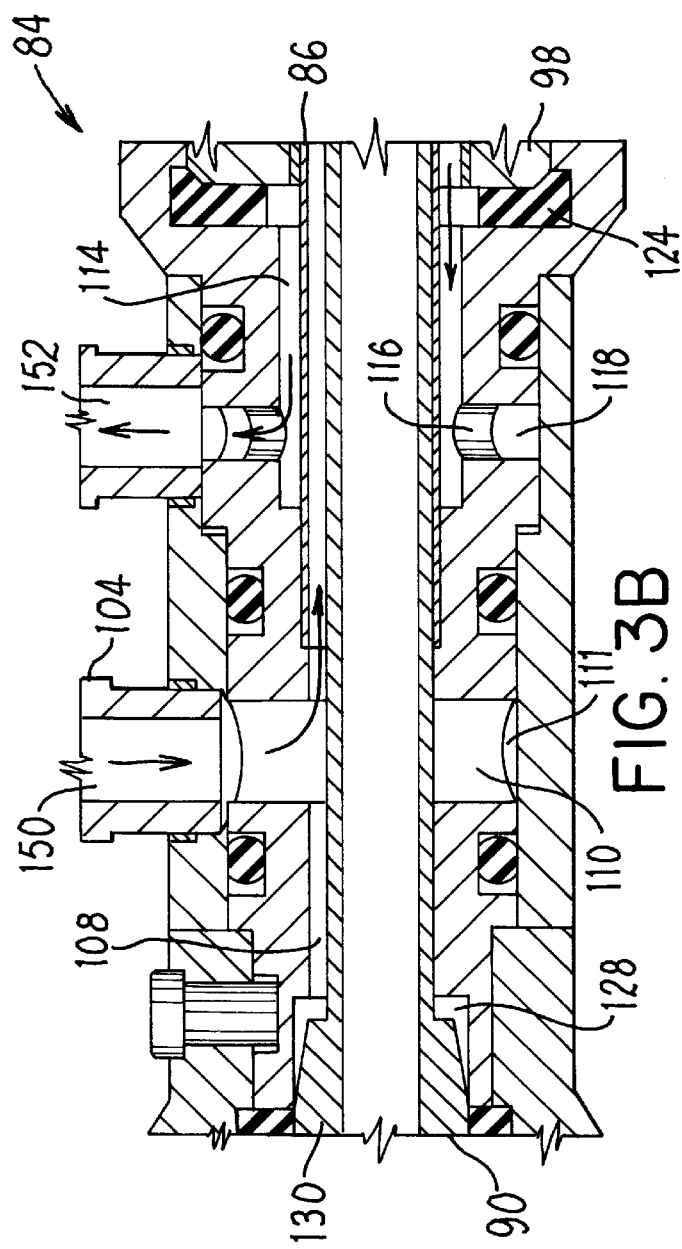
FIG. 3B is an enlarged view of a portion of the main body subassembly of the pressure sensing cannula illustrated in FIG. 3A.

The housing 102 of the main body subassembly 84 of the pressure sensing cannula 46 is now described primarily by reference to FIGS. 3B, 4 and 7. The housing 102 includes a sleeve-like shell 136 that is fitted over the cannula body 98. Shell 136 is formed to have bore 138 that extends from the proximal end of the shell. Bore 138 functions as the space the portions of the cannula body 98 that define the inflow bore 108 and the tube bore 112 are seated. The shell 136 is further formed to have a counterbore 140 that is slightly larger in diameter than bore 138 that extends from bore 138 to the distal end of the shell. Counterbore 140 serves as the space in which the portion of the cannula body 98 that defines the pressure feedback bore 114 is seated, this portion of the cannula body having an outer diameter that is slightly large than the outer diameter of the immediately proximal portions of the cannula body.

Three O-rings 142 extend around the cannula body 98 to provide fluid-tight seals between the cannula body and the shell 136 of the housing 102. A first O-ring 142 is seated in a groove 144 formed in the outer surface of the cannula body along a plane distal to the plane in which the feedback ports 116 are centered so as to prevent the feedback fluid from leaking out from the distal end of the housing 102. A second O-ring 142 is seated in a groove 146 formed in the cannula body 98 located between the inflow ports 110 and the feedback ports 116 so as to prevent contact between the inflowing sterile solution and fluid that forms the monitored water column. A third O-ring 142 is located in a groove 148 formed in the cannula body 98 along a plane proximal to the inflow ports 110. The third, most proximal O-ring thus serves as barrier to prevent the inflowing sterile solution from leaking from the proximal end of the housing 102. In the illustration version of the invention, the diameter of groove 144 is greater than that of the grooves 146 and 148. Thus, the most distal O-ring 142 is greater in diameter than that of the two proximal O-rings 142.

The stopcock 104 and outlet stud 106 are fitted to shell 136 and are longitudinally aligned with each other. Stopcock 104 and outlet stud 106 are formed with bores 150 and 152 respectively. The inflowing sterile solution flows into the inflow ports 110 through stopcock bore 150. The fluid that forms the monitored water column flows from the feedback bores 116 and into stopcock bore 152. The tips of both stopcock 104 and outlet stud 106 are shaped to receive luer locks that, respectively, are fitted on the ends of the inflow tube 42 and the pressure line inlet tube 78. A valve 154 is integrally attached to stopcock 104 so as to allow manual adjustment of the introduction of sterile solution at the point the solution is introduced into the pressure sensing cannula 46.

The cap 92 of the main body subassembly 84 of the pressure sensing cannula of this invention is actually multi-piece sub-assembly as illustrated by FIGS. 8A and 8B. The cap 92 includes a cap insert 158 that is the component that is secured to the cannula body 98. A cap cover 160 is secured to the proximal end of the cap insert 158 and serves as the outermost component of the pressure sensing cannula 46. A cap lock 162 is slidably disposed between the cap insert 158 and the cap cover 160. The cap lock 162 serves as the component of the pressure sensing cannula 46 that secures the endoscope 90 in place. An elastic O-ring 164 seated around the cap cover 160 latches the cap lock 162 in place.

The cap insert 158, as seen by FIGS. 8B, 9A and 9B, includes a ring-like base 166 that is seated over the proximal end of the cannula body 98. A guide pin 168 is seated in a bore 167 formed in the base 166 of the cap insert 158 so as to project into the center of the cap insert. When the cap 94 is coupled to the cannula body 98, guide pin 168 is fitted in guide slot 133 in order to properly align the cap. Two set screws 170 (FIG. 2) are fitted in threaded bores 171, in the base 166. When the cap 94 is properly positioned relative to the cannula body 98, set screws 170 are tightened so as to secure the cap in place. It will be further noted from FIG. 3A that the distal end of the cap insert 158 abuts the proximal end of the housing 102. Thus, the securement of the cap 94 to the cannula body 98 also serves to likewise hold the housing 102 over the cannula body.

The cap insert 158 is further formed with a transition section 172 located proximal to the base 166 that is further tapered outwardly from the base. Transition section is formed to define an internal bore 174 that is larger in diameter than the distal bore in the base in which the end of the cannula body 98 is seated. A seal 176 (FIG. 3A) is fitted in bore 174 to provide a liquid-tight barrier around the proximal terminus of the endoscope receiving socket 128 which is in fluid communication with inflow bore 108. A pair of parallel, spaced apart guide webs 178 are integrally formed with cap insert 158 so as to be located on the opposed sides of the proximal end of the transition section 172. As will be described hereinafter, the cap lock 162 is slidably secured between webs 178. In terms of relative dimension, webs 178 extend a small distance forward of the front surface of cap lock 162. The inner corners of the forward extending sections of the webs 178 are each provided with a small inwardly stepped surface 180. Stepped surfaces 180 do not extend the length of the webs 178 but are arcuate in profile and are centered along the center axis of the cap insert 158. The stepped surfaces 180 are flush with the adjacent front face of the cap lock 162.

The cap cover 160 includes a ring-like base section 182, as is seen by reference to FIGS. 8B and 10. Opposed sides of the base section 182 of the cap cover 160 are seated in the spaces defined by the stepped surfaces 180 of the cap insert 158 so as to facilitate the welding of the cap cover to the cap insert along the interface of these surfaces. The base section 182 of the cap cover 160 is formed to have a single slot 184 along the outer perimeter thereof. Slot 184 is designed to accommodate a pin 186 (FIG. 11A) integral with the cap lock 162 as will be discussed hereinafter. Integral with the base section 182 cap cover 160 has an outer eye ring 188 that has a diameter greater than that of the base section. The eye ring 188 is the outermost, or most proximal, portion of the pressure sensing cannula 46.

The cap lock 162, described with reference to FIGS. 8A, 8B, 11A and 11B, is generally in the form of an elongated, flat plate. The cap lock 162 is seated in the rectangular profiled space defined by the transition section 172 and webs 178 of the cap insert 158. The cap cover 160, which is located over the cap lock 162 prevents forward movement of the cap lock. An oval opening 190 extends through the center of the cap lock 162 to provide a passageway through which the endoscope 90 is inserted into the cannula body 98 and the cannula tube 86. The front, or proximal-directed, face of the cap lock 162 is formed to have an inwardly tapered surface 192 around opening 190. One end of cap lock 162 is further formed with a stepped surface 194 that extends forward of the front face of the cap lock. When the cap lock 162 is depressed, stepped surface abuts the base section 182 of the cap cover 160 so as to limit the movement of the cap lock. The opposed end of the cap lock is provided with the forward directed pin 186. When the cap is in the latched state, pin 186 is seated in slot 182.

The cap lock 162 is maintained in a latched state by O-ring 164. The O-ring 164 is located around the outside of the base section 182 of the cap cover 160 so as to normally hold pin 186 of cap lock 162 in slot 184. When the cap lock 162 is in this position, the curved portion of the tapered portion 192 adjacent the pin 186 is disposed in the space subtended by the center opening that extends through the cap cover 160. Consequently, when an endoscope 90 is inserted in the pressure sensing cannula 46, the shoulder section 130 of the endoscope displaces the cap lock 162. The cap lock 162 then seats in a reduced diameter neck section 131 of the endoscope 90 (FIG. 3A) so as to lock the endoscope in place. The endoscope 90 is removed from the pressure sensing cannula 46 of this invention by the simple downward depression of the end of the cap lock 162 that forms stepped surface 194. This displacement of the cap lock 162 releases cap lock from the space defined by the neck section 131 of the endoscope 90 so as to allow the removal of the endoscope.

Returning to FIGS. 3A and 3B, it is observed that the proximal end on the cannula tube 86 is welded into the tube bore 98 of the cannula body 98. The distal end of the cannula tube 86 is positioned at the surgical site. The cannula tube 86 is generally sleeve-like in shape. In the illustrated version of the invention, the cannula tube 86 is formed with an inwardly directed dimple 196 immediately forward of the distal end of the tube. Relative to the common center axis of the cannula tube 86 and the concentric bores 108, 112, 114 and 120 internal to the cannula body 98, the dimple 196 is located along a line that is diametrically opposite the line along which the axis of the endoscope receiving socket 128 is located. Consequently, when the endoscope 90 is inserted in the pressure sensing cannula 46, the elongated body of the endoscope presses against the dimple 196. Thus, dimple 196 ensures that the off-center relationship between the axis of the cannula tube and the axis of the endoscope 90 is maintained throughout the length of the cannula tube.

As seen by reference to FIGS. 2 and 12, the outer sleeve 88 is generally tube like in shape. The proximal end of the outer sleeve is welded or otherwise permanently secured in the sleeve adapter 122. The sleeve adapter 122 generally has a solid, cylindrical body. The outer surface of the sleeve adapter 122 is formed with an L-shaped groove 198 that extends rearwardly from the proximal end of the sleeve adapter. When the main body subassembly 84 of the pressure sensor cannula 46 is inserted in the outer sleeve 88, the lock pin 127 associated with the cannula body 98 is initially seated in groove 198. The laterally extending section of groove 198 is spaced relative to the proximal end of the sleeve adapter 122 so that when the sleeve 88 is rotated so as to be located in place, the sleeve adapter is compressed against the outer tube seal 124. Consequently, the outer tube seal 124, in addition to providing a seal around the sleeve adapter 122, provides an outwardly directed force that urges the portion of the sleeve adapter that defines groove 198 against the lock pin 127. This force serves as a latching force to prevent the unintended rotation of the sleeve adapter 122. To facilitate the rotation of the outer sleeve 88 required to couple and uncouple it to the main body subassembly 84, the sleeve adapter 122 is provided with lever arm 200 that extends radially away from the distal end of the sleeve adapter.

A bore 202 extends longitudinally through the sleeve adapter 122 so as to accommodate the outer sleeve 88. The sleeve adapter 122 is, however, formed so that bore 202 is not coaxially aligned with the center axis of sleeve adapter 122. Rather, the axis of the bore 202 is offset from the axis of the sleeve adapter 122 so as to be aligned with the axis of the endoscope receiving socket 128. Thus, as seen by reference to FIG. 6, when the pressure cannula 46 and endoscope 90 are positioned at the surgical site, the outer sleeve 88 of the cannula is concentrically aligned with the elongated main body 132 of the endoscope. Consequently, when the main body subassembly 84 and the outer sleeve 88 of the cannula 46 are coupled together, the cannula tube 86 and the outer sleeve 88 are axially offset from each other. As a result of this axial offset, the elongated space between the cannula tube 86 and outer sleeve 88 has a crescent shaped profile. As represented by arrow tails 204, this is the space through which the liquid-state fluid at the surgical site is feedback to the tube set 34 so that the fluid pressure at the surgical site can be monitored.

Figure 6:
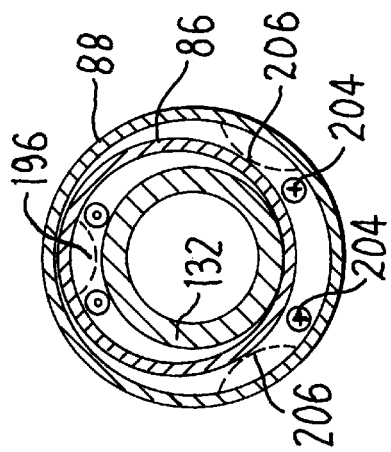
FIG. 6 is a cross sectional view taken along line 3—3 of FIG. 3A illustrating the relative axial relationships of the endoscope, the cannula tube and the outer sleeve of the pressure sensing cannula.

The distal end of the outer sleeve 88 is formed to have two inwardly directed dimples 206. As shown by FIG. 6, dimples 206 are spaced 60° from each other and both dimples 206, relative to the center axis of the endoscope 90, are spaced 60° from dimple 196 integral with the cannula tube 98. The outer surface of the distal end of the cannula tube 98 abuts the dimples 206. The dimples 206 thus help maintain the axial displacement of the cannula tube 86 and the outer sleeve 88.

Figure 13:
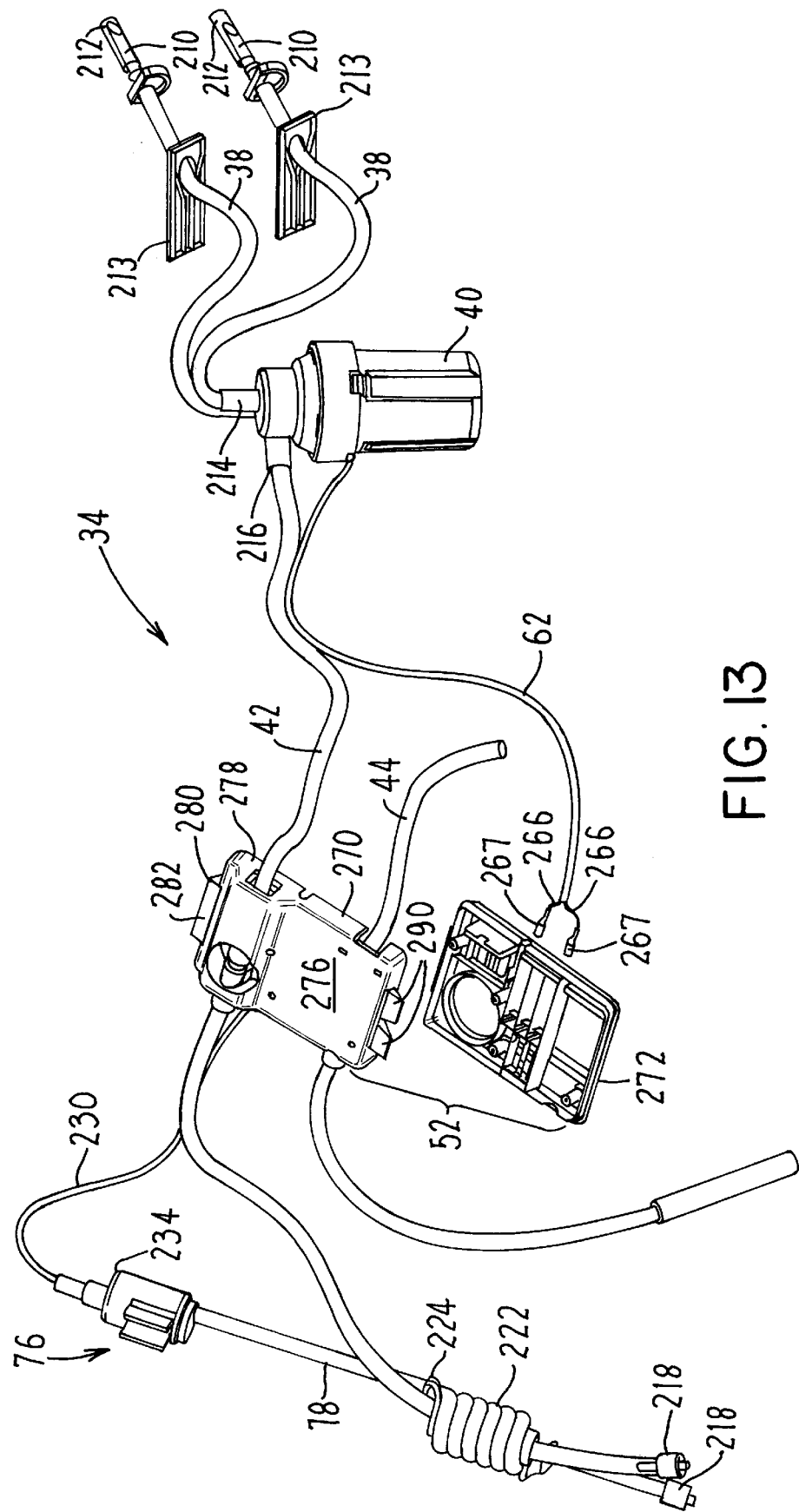
FIG. 13 depicts the basic components forming the tube set.
Figure 16:
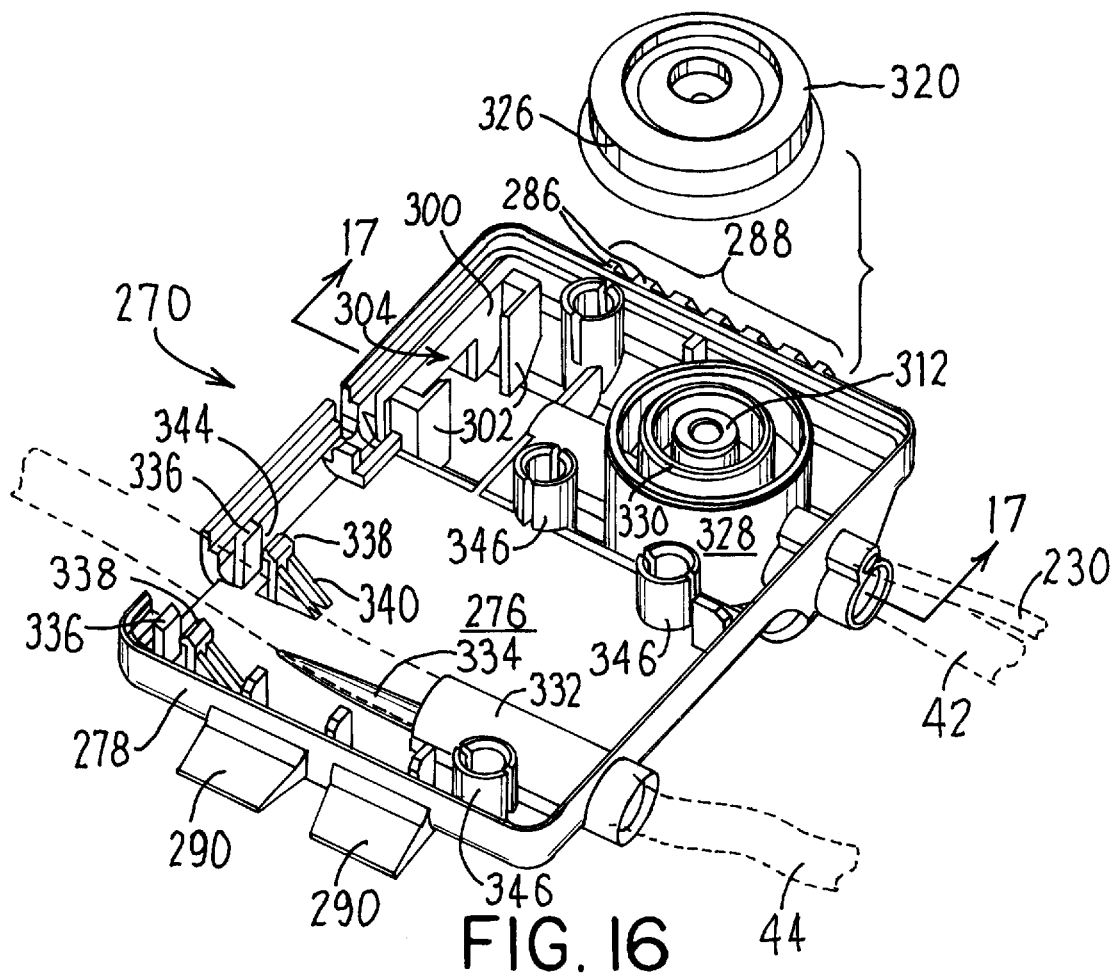
FIG. 16 is a view of the inside of the chassis of the cassette of the tube set.
Figure 17:
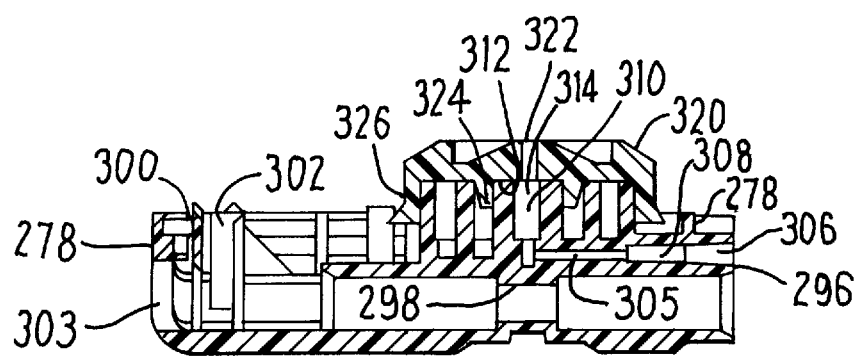
FIG. 17 is a cross sectional view of the chassis taken along line 17—17 of FIG. 16.

FIG. 13 illustrates the basic components forming the tube set 34. Each fluid inlet tube 38 is provided at one end with a spike 210 designed for insertion into a container 36 of sterile fluid and that provides a flow path for the fluid from the container into the tube. Prior to use, the end of each spike 210 is contained in a removable cover 212. The opposed ends of the fluid inlet tubes 38 are fitted into inlet ports 214 formed in the pump 40. A slide clamp 213 is fitted over each fluid inlet tube 38 between the spike 210 and the pump 40. The slide clamps 213 are conventional devices for manually regulating fluid flow from the containers 36 to pump 40.

The inflow tube 42 extends from an outlet port 216 integral with the pump 40. In the depicted versions of the invention, inflow tube 42 is a single piece of tubing; the tube extends as a single piece through the cassette 52. A luer lock connector 218 is fitted to the end of the inflow tube 42 distal from the pump 40. Luer lock connector 218 facilitates the coupling of the inflow tube 42 to stopcock 104 of the pressure sensing cannula 46.

The outflow tube 44, like the inflow tube 42, is formed from a single piece of tubing. One end of the outflow tube 44 is connected to the surgical site through a drain cannula, not illustrated and not part of this invention. The opposed end of the outflow tube 44 leads to an appropriate receptacle 220 (FIG. 1) for collecting the fluid and other material drained from the surgical site. The pressure line inlet tube 78 is the component of the pressure sensing assembly 76 that is directed connected to the pressure sensing cannula 46. The free end of the pressure line inlet tube 78 is provided with a luer lock connector 218 to facilitate the connection of the tube to outlet stud 106 of the pressure sensing cannula 46. The pressure line inlet tube 78 is formed with a material that has a relatively low surface tension. One such material is a polymer tubing sold as Tygon 2075 by Norton Performance Plastics of Akron, Ohio. In many preferred versions of the invention the inside diameter of the pressure line inlet tube 78 is between 0.100 and 0.250 inches; in more preferred versions this tubing has an inside diameter of 0.125 inches. When the pressure line inlet tube 78 is placed in fluid communication with the surgical site through the cannula 46 a liquid-state fluid column forms in the tube. As a result of the low surface tension of the material forming pressure line inlet tube 78, as the fluid column shifts position in the tube 78, drops of liquid are not left behind as the meniscus that forms the fluid column retracts. Thus, inside the pressure line inlet tube 78 a well defined separation forms between the head of the liquid-state fluid column and the base of an air column; it is the pressure of this air column that is monitored by the transducer 80 internal to the control unit 50.

In the depicted version of the invention a section 222 of the pressure line inlet tube 78 is wrapped in a helical pattern around a barrel 224. The barrel 224, as seen in FIG. 14, includes a sleeve like body 226. Helically shaped guide tabs 228 are integrally formed with the ends of the body 226 so as to extend outwardly therefrom. The end of each guide tab 228 is formed with an opening 229 through which the pressure line inlet tube 78 is inserted. The pressure line inlet tube 78 extends through one guide tab 228, is wrapped around the body 226 of the barrel 224 to form the helical wrap section 222 of the tube, and then extends throughout the second guide tab 228. The guide tabs 228 thus prevent the pressure line inlet tube 78 from unwinding from the barrel 224. In the illustrated version of the invention, the end of the inflow tube 42 that is coupled to the pressure sensing cannula 46 extends through the center of the barrel 224, through the center of the helically wrapped section 222 of the pressure line inlet tube 78. The helically wrapped section 222 of the pressure line inlet tube 78 thus performs three functions, it provides a relatively long length of tubing in a relatively small space, in which the head of the monitored fluid column can form. Secondly, it functions as a sleeve to hold the ends of the inflow tube 42 and the pressure sensing assembly 76 together. Thirdly, the helical wrapped section 222 serves as a handle for the user to grasp the assembly during use.

An air column line 230, also part of the pressure sensing assembly 76, serves as a conduit between the pressure line inlet tube 78 and the cassette 52. In the illustrated version of the invention, the pressure line inlet tube 78 and the air column line 230 are connected together by an air-water separator 234. The air water separator, now described by reference to FIGS. 15A and 15B, preforms two functions. During normal operation of the fluid management pump system 30 of this invention, air water separator functions as a filter to prevent air-borne bacteria present in the feedback fluid drawn from the patient from reaching the pressure transducer 80 internal to the control unit 50. Secondly, in the event a portion of the liquid-state fluid in the pressure line inlet tube 78 reaches the end of the tube 78, the air-water separator serves as a barrier that prevent this liquid from entering the air column line 230. This prevents the liquid from contacting the control unit 50.

Air-water separator 234 includes a housing that is formed out of a base section 236 and a lid 238. The base sections 236 is formed to have an cylindrical shell 240 that is closed at one end. A stem 242 with an inlet bore 244 extends from the closed end of the shell 240. The pressure line inlet tube 78 is fitted over the stem 242 so as to connect the tube 78 to the air water separator 234. In the illustrated version of the invention, an elongated C-shaped tube clip 245 is formed integrally with shell 240. Clip 245 facilitates the removable securement of the inflow tube 42 or the outflow tube 44 to the air-water separator 234.

A sponge 246 is disposed inside the shell 240 of the air-water separator 234. Sponge 246 is capable of absorbing some water and is further designed to allow air to pass therethrough. One suitable sponge 246 is a polyvinyl acetate sponge with a density of CF100 that is manufactured by the Merocel Corporation of Mystic, Conn. Sponge 246 has a generally cylindrical shape. The sponge 246 is further formed to have a bore 248 that extends therethrough and that is axially offset from the longitudinal axis of the sponge. In order to facilitate the proper seating of the sponge 246 in the shell 240, the base is formed with a set of fingers 249 the extend from the closed end of the base into the space defined by shell 240. Sponge 246 is seated in the shell 240 so that the fingers 249 are seated in bore 248.

The sponge 246 is positioned in the base section 236 so that the liquid absorbing section thereof directly faces the bore 244 associated with stem 242. Moreover, the sponge 246 rests on an inwardly directed annular lip 250 formed integral with the base section 236. The base section 236 is further formed so as to define an internal counterbore 252, concentric with bore 244. It is counterbore 252 that serves as the flow path from the pressure line inlet tube 78 to the sponge 246. Consequently, the initial volume of liquid introduced into the air-water separator is immediately absorbed by the sponge 246. The air in the sponge 246 will be forced into the air column line 230. The absorbative characteristics of the sponge 246 thus delay the flow of the water through the air-water separator 234. The lid 238 includes a round base 252 which is seated in the open end of shell 240. When the lid 238 is so seated, the lid compresses the sponge 246 against the opposed, closed surface of the shell 240 so as to prevent liquid flowing directly from counterbore 252 through sponge bore 248 and out through the air-water separator 234. The lid 238 is further formed to have an outlet stem 254 that extends away from the air-water separator. The outlet stem 254 defines a bore 256 through which there is fluid communication between the air-water separator 234 and air column line 230. The lid 238 is secured to the base section 236 of the air-water separator 234, so that outlet bore 256 is concentrically aligned with the bore 244 internal to the sponge 246. To facilitate this relative alignment, the base section 236 and the lid 238 are, respectively, provided with a positioning tab 258 and a complementary slot 260.

Outlet stem 254 is further formed with an internal counterbore 264. Counterbore 264 is located between the bore 248 internal to the sponge 246 and the outlet bore 256 of the air-water separator 234. A bacteria filter 265 is seated in counter bore 264. One suitable bacteria filter is Filter No. X-7909 marketed by Porex of Fairburn, Ga. This filter 265, in addition, to preventing air-borne transmission of bacteria, is formed of material that expand when exposed to water. Consequently, when water initially strikes the surface of filter 265, it causes the filter to expand and form a barrier that prevents gas flow through the filter. Once this barrier forms, the position of the base of the air column in the air column line essentially remains constant. Therefore, the air pressure presented to the transducer 80 internal to the control unit 50 likewise remains constant. As will be discussed hereinafter, the detection of this constant pressure state by the control unit 50 is interpreted by the control unit as a malfunction of the fluid management pump system 30.

Returning to FIG. 13, it can be seen that the cable 62 over which energization signals are supplied to the pump 40 includes two wires 266. Connectors 267 are attached to the end of the wires 266 to provide the mechanical connection to the components internal to the cassette 52 through which the energization signals are supplied to the pump 40.

The cassette 52 has a body that is formed out of two pieces of plastic, a chassis 270 and a cover 272. The chassis 270 serves as the front panel of the cassette 52 as well as the portion of the cassette to which the inflow tube 42, the outflow tube 44 and the air column line 230 are mounted. The cover 272 serves as the back panel of the cassette 52, the portion of the cassette that is disposed against the control unit 50. The wires 266 integral with power cable 62 are attached to the chassis 270.

The chassis 270 of the cassette 52 is now described by reference to FIGS. 13, 16, 17 and 19. The chassis 270 is formed to have an outer face panel 276 that is generally but, not completely, a planar structure. Integral with face panel 276, chassis 270 is shaped to have a curved rim 278 that extends around the perimeter of the chassis and that provides depth to the chassis. Extending upwardly from a portion of the rim 278 that defines the top surface of the cassette 52 is a latch tab 280. Latch tab 280 is shaped to have a front latch surface 282. Latch surface 282 is the surface of the cassette 52 that abuts against a complementary lock tongue 284 (FIG. 1) integral with the control unit 50 that holds the cassette 52 to the control unit. A set of small triangular shaped webs 286 provide structural rigidity to the material forming the latch surface 282. Collectively, the exposed surfaces of webs 286 define a latch landing 288. The latch landing 288 is the surface of the cassette 52 that initially abuts the lock tongue 284 when the cassette is attached to the control unit 50.

Chassis 270 is further formed so as to have two legs 290 that extend outwardly from the portion of the rim 278 that defines the bottom surface of the cassette 52. In the depicted version of the invention, each leg 290 has a generally planar shape. The legs 290, while integral with the rim 278, are positioned to have a slight upward orientation. When the cassette 52 is secured to the control unit 50, the legs 290 are seated in slots 292 formed in a cassette holder 294 that is part of the control unit 50 (FIG. 28). The seating of the legs 290 in the slots 292 thus properly positions the cassette 52 so that the cassette can be locked to the control unit 50.

Molded integrally with the chassis 270 is an upper sleeve 296. Upper sleeve 296 extends laterally from a position spaced from a side surface defined by rim 278 to a position approximately three-quarters of the length into the chassis 270. The upper sleeve 296 serves as a conduit in which the inflow tube 42 is seated. Upper sleeve 296 is formed to have a neck section 298 in the center thereof with an inside diameter that is less than the inside diameter of the rest of the sleeve. The portion of the sleeve 296 defining the neck section 298 slightly compresses the inflow tube 42. Further movement of the inflow tube is blocked by a adhesive applied between the tube and the chassis 270.

The side of the chassis 270 opposite the side in which the upper sleeve 296 is formed with a generally U-shaped guide plate 300 that projects upwardly from the inside surface of the face panel 196 into the center of the chassis. Guide plate 300 is parallel aligned with the side edge of the chassis 270. Two L-shaped guide posts 302 extend upwardly from the face panel adjacent the guide plate. More particularly, the guide posts 302 are spaced apart from and oriented so that the elongated portions thereof are parallel aligned with the guide plate 300. The inflow tube 42 extends between the guide posts 302, through the center of the guide plate 300. From the guide plate 300, inflow tube 42 extends out of the cassette 52 through an opening 303 in the rim 278 of the chassis 270. The space between the guide plate 300 and guide posts through which the inflow tube 42 extends is a blade seating space 304. As described hereinafter, a component of the pinch valve 54 selectively compresses the portion of the inflow tube 42 that extends through the blade seating space 304 so as to control fluid flow through the tube 42.

Figure 19:
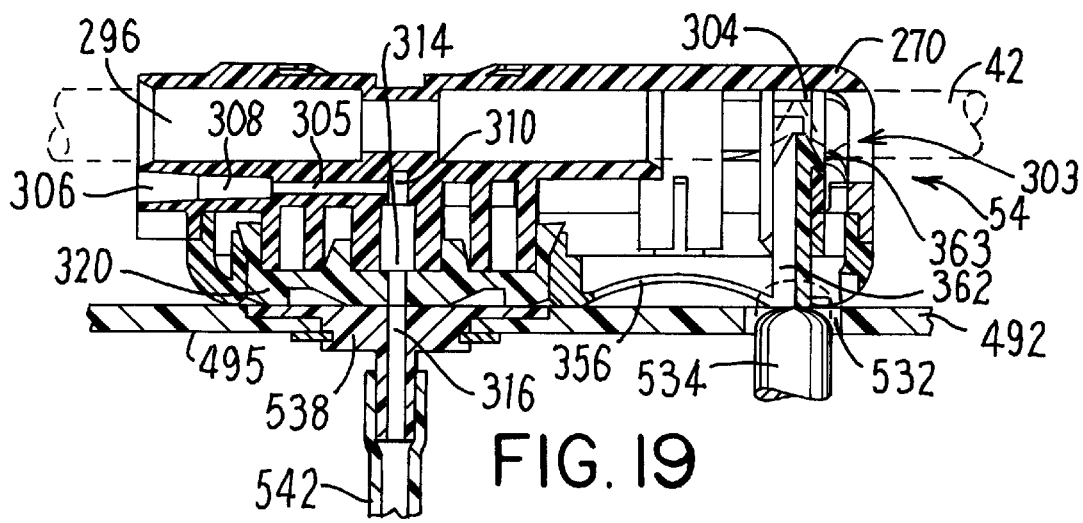
FIG. 19 is a cross sectional view of the pinch valve internal to the cassette employed to regulate fluid flow through the inflow tube and the solenoid plunger that actuates the pinch valve.

A pressure feedback bore 305 is formed in the chassis 270 so as to extend parallel with the upper sleeve 296 as seen best in FIG. 19. More particularly, in the illustrated version of the invention, the chassis 270 is formed to have a counterbore bore 306 that has an opening in line with the opening to the upper sleeve 296. The end of the air column line 230 is seated in counterbore 306. An intermediate bore 308 internal to the chassis 270 connects counter bore 306 to bore 305. Bores 305, 308 and counterbore 306 are coaxially aligned with each other. Bore 306 has a diameter between that of the diameter of pressure feedback bore 305 and counterbore 308. Pressure feedback bore 305 is in fluid communication with a feedback fluid outflow bore 310 that extends perpendicularly from the pressure feedback bore 305. The feedback fluid outflow bore 310 is formed in a cylindrical boss 312 formed as part of the chassis 270. The feedback fluid outflow bore 310 has a discharge port 314 positioned to open into a complementary bore 316 formed in the control unit 50. Thus, the air column formed in the pressure sensing assembly 76 is presented to the transducer 80 in the control unit 50 through the discharge port 314 A face seal 320 fitted to the chassis 270 provides a fluid-tight seal between the discharge port 314 integral with the cassette and the complementary port 316 formed in the control unit 50. Seal 320 is composed of flexible material such as a thermoplastic or an elastomer. Seal 320 has a generally circular shape and is formed with a center opening 322 that allows fluid communication from ports 314 to port 316. The face seal 320 is further formed to have an inwardly directed annular lip 324 that is radially spaced a slight distance away from the portion of the seal 320 that defines opening 322. The lip 324 of seal 320 is fitted around the outside of the boss 312 that is integral with the chassis 270. The face seal 320 is further formed to have an annular rim 326 that is oriented in the same direction of the lip 324.

To facilitate the mating of face seal 320 to the cassette 52, chassis 270 is formed with two annular webs 328 and 330 that are concentric with boss 312. Web 328 is the larger diameter web. The annular rim 326 of the face seal 320 is fitted around the outside of web 328. Web 330 is the smaller diameter web; it is located between boss 312 and web 328. Web 330 provides rigidity to the barrier established by seal 320.

The chassis 270 is also formed with a lower sleeve 332 that is integral with the inside surface of face panel 276. Lower sleeve 332 is positioned to have an opening in line with the opening associated with upper sleeve 296 and extends slightly less than half way through the cassette 52. The lower sleeve 332 serves as the conduit in which the outflow tube 44 is seated. The chassis 270 is further formed so that a shallow groove 334 is formed in the inside surface of the face panel 276 adjacent the lower sleeve 332. Groove 334 serves as a seating space for outflow tube 44 so as to minimize the compression of the tube 44.

Figure 20:
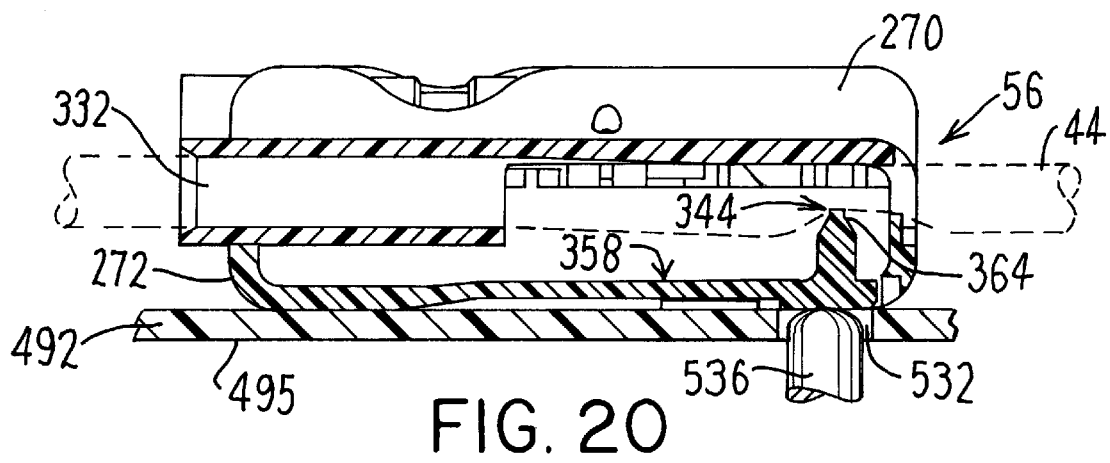
FIG. 20 is a cross sectional view of the pinch valve internal to the cassette employed to regulate fluid flow through the outflow tube and the solenoid plunger that actuates the pinch valve.

The side of the chassis 270 opposite the side with which the lower sleeve 332 is formed is formed with two pairs of guide posts 336 and 338. Guide posts 336 are located proximal to the adjacent rim 278 of the chassis, guide posts 338 are located distal to the rim. Each guide post 338 is located a slight distance away from a complementary one of the guide posts 336. Structural strength is provided to the guide posts 338 by triangularly shaped reinforcing flanges 340 that extend between the guide posts and the adjacent surface of the face panel 276. The outflow tube 44 extends between the spaced guide posts 338, the spaced guide posts 336 and out of the cassette 52 through an opening 342 formed in the rim 278 of the chassis 270. The space between the guide posts 336 and 338 is a blade seating space 344 (FIG. 20). As will be described hereinafter, the section of the outflow tube 44 that extends through the blade seating space 344 is the portion of the tube 44 that is selectively opened and closed by the pinch valve 56.

Chassis 270 is further formed to have a number of tube shaped sockets 346 that extend upwardly from the inside surface of the face panel 276. Sockets 346 receive posts 348 integral with cover 272 to facilitate the assembly of the cassette 52.

The cover 272, now described by reference to FIGS. 18A and 18B, is formed from a plastic that is both flexible and returns to its initial, molded shape after the deforming force is removed. One such plastic suitable for forming the cover 272 is marketed as Cycolac T2502 by General Electric Plastics. The cover 272 is formed to have a generally planar back panel 352 that serves as the back panel of the cassette 52 that is positioned against the control unit 50. A rim 354 that extends around the perimeter of the back panel 352 so as to provide the cover 272 with depth and structural rigidity. The posts 348 extend away from the inside face of the back panel and into sockets 346 so as provide structural rigidity to the cassette 52.

A circular opening 356 is formed in the back panel 352. The boss 312 and seal 320 associated with the chassis 270 extend through opening 354 so as to provide an interface between the discharge port 314 of the cassette 52 and the complementary bore 316 in the control unit 50. The cover 272 is further formed so that an integral part of the back panel 352 are two pivoting cantilever arms 356 and 358. Cantilever arm 356, which pivots relative around an axis adjacent opening 354, forms part of the pinch valve 54 that regulates fluid flow through the inflow line 42. Cantilever arm 358 extends approximately three-quarters of the distance along the width of the back panel 352, along the end of the panel opposite the end in which cantilever arm 356 is formed. Cantilever arm 358 is part of the pinch valve 56 that regulates fluid flow through outflow line 44. In the illustrated versions of the invention, it will be noted that while cantilever arm 358 is formed out of a generally solid section of plastic, cantilever arm 356 is formed out of four spaced apart webs 360. Cantilever arm 356 is formed out of a set of webs 360 because, owing to its relatively short length, it would not have the required degree of flexibility if it were formed out of a solid section of plastic.

Integral with cantilever arm 356 is a valve blade 362 that extends perpendicularly away from the arm 356 toward the chassis 270. As seen by reference to FIG. 19, valve blade 362, which is part of pinch valve 54, is the component of the valve that normally seats against the portion of the inflow tube 42 that extends through blade seating space 304. When the cantilever arm 356 is depressed, valve blade 362 is urged into the blade seating space 304 so as to pinch the outflow tube 44 closed. Owing to the elasticity of the material forming the cover 272, when the force depressing cantilever arm 356 is withdrawn, the arm returns to its static position; valve blade 362 thus releases the compressive force closing the inflow tube 42. Blade 362 is further formed to have a small tab 366 in the center thereof. Tab 363 clips under the center section of guide plate 300 to limit outward extension of the blade 362 when valve 54 is in the open state.

Integral with cantilever arm 358 is a valve blade 364 that extends perpendicularly away from the arm 358 toward the chassis 270. As seen by reference to FIG. 20, valve blade 364, which is part of pinch valve 56, is the component of the valve that normally seats against the portion of the outflow tube 44 that extend through blade seating space 344. When the cantilever arm 356 is depressed, valve blade 364 is urged into the blade seating space 344 so as to pinch the outflow tube 44 closed. When the force depressing cantilever arm 356 is withdrawn, the arm and valve blade 364 return to their initial state so as to allow fluid flow to resume through the outflow tube 44.

An ID contact 366 is mounted to the cover 272 to provide control unit 50 an indication of the type of the tube set 42 that is mounted thereto. The ID contract 366 is formed from a single piece of conductive metal and is shaped to have two parallel spaced apart rails 368. The ends of the rails 368 are connected together by cross webs 370. The ID contact 366 is shaped so that the center of the rails 368 are raised relative to the remaining portions of the rails so as to define contact terminals 372.

The ID contact 366 is positioned in the cover 272 so that the contact terminals 372 project out of two of three openings 374 formed in the back panel 352. To facilitate the securement of the ID contact 366 to the cover 272, the ID contact is shaped so that the ends of rails 366 and the cross webs 370 are oriented at an angle approximately 75° from the plane in which the rails 366 are aligned. The ends of the webs 370 of the ID contact 366 are seated in grooves, (not illustrated) defined in rails 378 (one shown) formed integrally with cover 272. More particularly, one rail 378 is formed integrally with rim 354; the opposed rail 378 is formed as part of a web 379 that extends inwardly from the inside surface of back panel 352.

The exact placement of the ID contact 366 relative to the openings 374 is a function of which one of two types of tube sets 34 the cassette 52 is assembled to form. If the cassette 52 is to be integrated into a first type of tube set 34, the ID contact 366 is positioned so that the contact terminals 372 project out of the middle and upper openings 374. If the cassette is to be integrated into a second type of tube set, the ID contact 366 is secured in the cover 272 so that the contact terminals 372 extend out of the middle and lower openings 374.

The cover 272 is further provided with two power contacts 380 that serve as conductive paths between the control unit 50 and the cable 62 over which the energization signals are applied to the pump 40. Each power contact 380 is in the form of a strip of conductive metal that is shaped with a raised center section that serves as a contact terminal 382. A tab 384 that extends away from one end of the contact 380. The tab 384 serves as the portion of the contact 380 to which a complementary connector 267 integral with one of the wires 266 is attached.

The power contacts 380 are positioned in the cover 272 so that the contact terminals 382 extend out of openings 385 formed in the back panel 352. To facilitate the securement of the power contacts 380 to the cover, the opposed ends of the power contacts are bent so as to be at an angle that is approximately 70° from the plane in which the contacts lie. The ends of the power contacts 380 are snap secured into grooves, (not illustrated) defined by rails 388 (one shown) formed as part of the cover. A first one of the rails 388 extends along the side of the web 379 opposed the side of the web on which the rail 378 is formed. The second rail 388 is integrally formed with the rim 354. The power contacts 380 are kept separated by partition plates 390 that extend between web 379 and rim 354.

Figure 21:
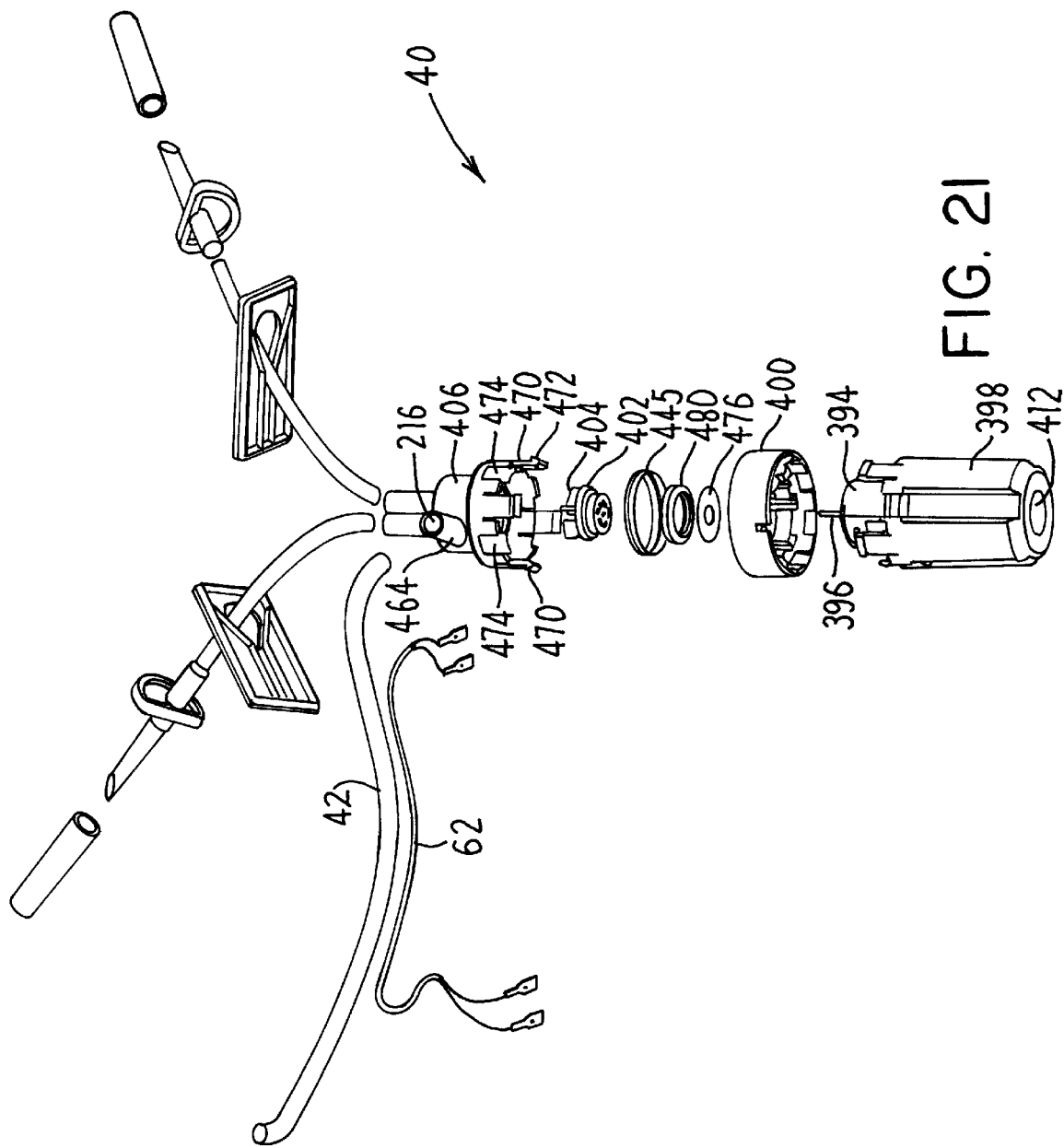
FIG. 21 is an exploded view of the pump incorporated into the tube set of this invention.

The pump 40, which is part of the tube set 34, is now described by initial reference to FIG. 21. The pump 40 includes a motor 394 that provides the motive power for forcing the sterile solution through the inflow tube 42. One suitable motor 394 is a DC motor manufactured by Mabuchi Motor, Ltd., of Japan as Motor No. FS-390/PH 4046. Motor 394 includes a shaft 396 that rotates in response to the application of energization signals to the motor. The motor 394 is housed in a back cap 398 that is generally cylindrical in shape and that is closed at one end. A hub 400 is fitted around the open end of the back cap 398. An impeller 402 is fitted over the exposed shaft 396 of the motor 394. The impeller 402 has a set of blades 404. When the impeller 402 is rotated by the motor 394, the solution surrounding the blades 404 is forced by the blades through the inflow line 42. A volute 406 is seated over the hub 400 and the impeller 402. As seen best by FIG. 24, inside of the volute 406 serves as the pump chamber 408 in which the impeller 402 is seated. The volute 406 is the component of the pump 40 formed with the inlet ports 214 through which the sterile solution is introduced to the pump. The volute 406 is also formed with the outlet port 216 through which the solution-under-pressure is discharged from the pump chamber 408 into the inflow tube 42.

Figure 22:
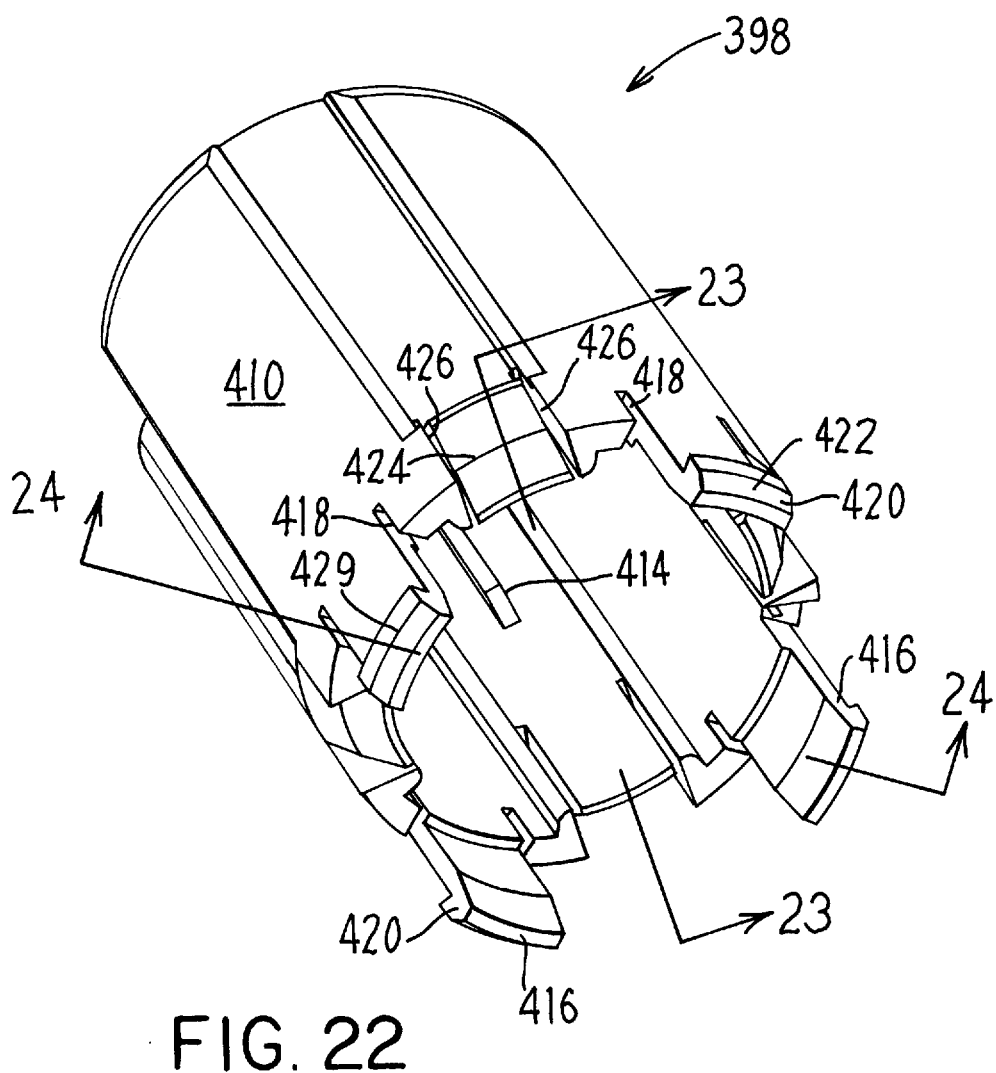
FIG. 22 is a perspective view of the back cap of the pump of FIG. 21.

As seen by reference to FIGS. 21 and 22, the back cap 398 has a generally cylindrical body 410. The closed end of the body 410, which forms the base surface of the pump 40, is shaped to have an inwardly directed sleeve 412 that extends into the center of the body, (opening to the sleeve shown in FIG. 21). The base of the motor 394 is seated on the end of the sleeve 412 in the body 410. The body 410 of the back cap 398 is also formed with a number of longitudinally extending, inwardly directed ribs 414 that extend into the center of the body (one rib shown). Ribs 414 abut the motor 394 so as to stabilize the motor in the body.

The back cap 398 is further formed so as to have four equidistantly spaced fingers 416 that extend upwardly from the top of the body 410. The fingers 416 are flush with the body and separated from the adjacent upper perimeter of the body by small slots 418. The fingers 418 are formed so that the upper ends thereof of have outwardly directed flanges 420 the tops of which are shaped to have downwardly beveled surfaces 422. The back cap 398 is further formed so that integral with the body 410 are four flexible tabs 424. The tabs 424 are located 90° apart from each other and each located between a separate two of the fingers 416. The tabs 424 are separated from the adjacent top section of the body 410 of the base cap by slots 426. The tabs 424 are shaped so as to have outer surfaces 429 that, from a level below the tope of the body 410 project out away from the body and that are tapered inward towards the upper perimeter of the body.

The hub 400, now described by reference to FIGS. 25A, 25B, 26 and 27, is the component of the pump 40 that covers the motor 394. The hub 400 is formed out of a single piece of plastic and is shaped to have a cap section 432 and a ring section 434 that surrounds the cap section. The cap section 432 has a disc-like top 436 in which an opening 438 is formed to accommodate a top, hub section, of the motor 394. The top 436 of the hub 400 is formed with teeth 440 that extend into the opening for engaging the top of the motor 394. The cap section 432 of the hub is formed with a sleeve-like rim 442 that extends around the top 436.

The hub 400 is shaped so that rim 442 extends a distance above and below the complementary top 436. A set of longitudinally extending ribs 443 are formed with the cap section 432 so as to extend downwardly from the bottom surface of the top 436 next to the inner surface of the rim 442. Ribs 443 are designed to engage the outer surface of the motor 394 so as to hold the motor steady in the pump 40. In order to facilitate the securement of the motor 394 in the pump ribs 443 are dimensioned so as to project a slight distance into the space occupied by the motor. When the pump 40 is assembled, the outer surfaces are sheared off and plastically deformed as a result of the insertion of the motor 394, this ensures that the motor will be tightly secured between the remaining material forming the ribs 443.

The top outer surface of the rim 442 of the hub 400 is shaped to have annular groove 444 extending therearound. Groove 444 is shaped to accommodate a ring-shaped peripheral seal 445 (FIG. 23) that provides a liquid-tight interface between the hub 400 and the abutting surface of the volute 406.

The ring section 434 of the hub 400 is generally sleeve like in shape. The ring section 434 has an inside diameter that is greater than the outsider diameter of the adjacent rim 442 of the cap 432. The ring section 434 is connected to the rim by eight spaced apart, wedge shaped webs 446. As will be described below, the complementary fastening members of the back cap 398 and of the volute 406 seat in the spaces between the webs 446. The ring section 434 itself is formed to have a rectangular slot 448 that extends upwardly from the bottom edge of the ring section. Slot 448 provides a through passage through the ring section through which the cable 62 extends for connection to the motor 394.

Figure 26:
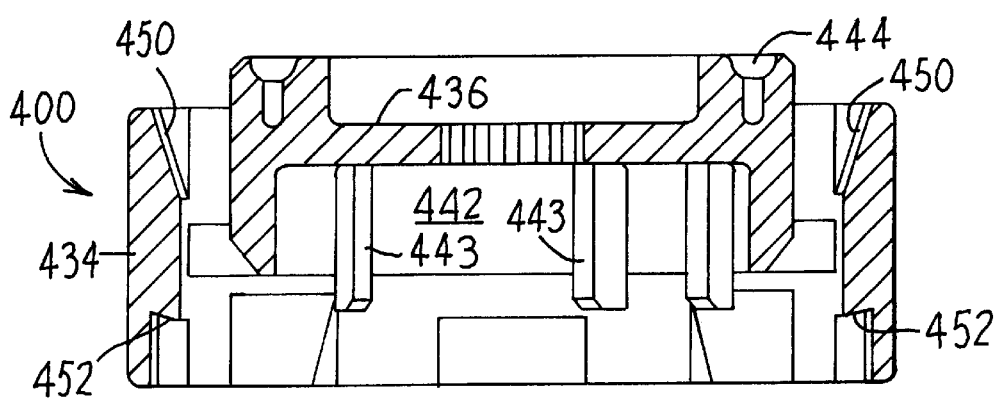
FIG. 26 is a cross sectional view of the hub taken along line 26—26 of FIG. 25A.
Figure 27:
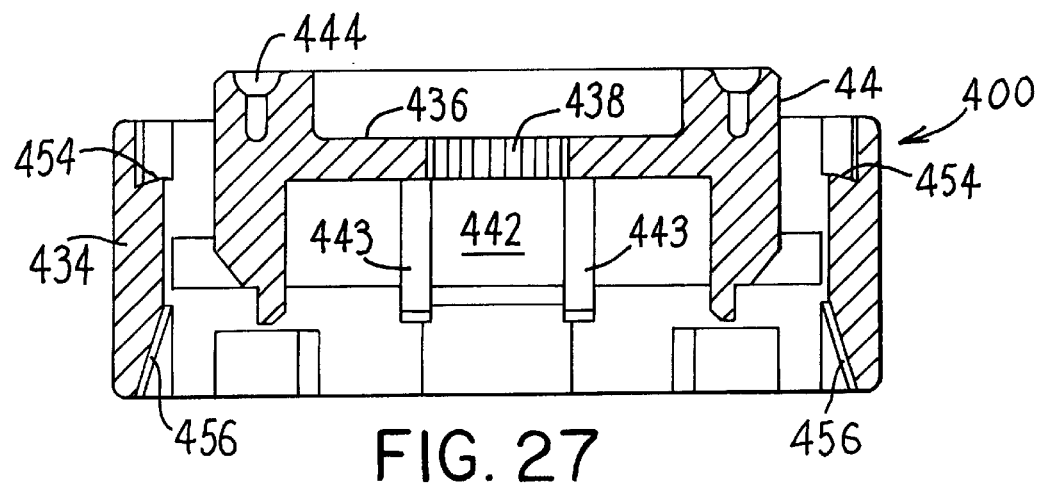
FIG. 27 is a cross sectional view of the hub taken along line 27—27 of FIG. 25A.

As seen by reference to FIG. 26, the top inside surface of the ring section 434 adjacent four of the alternating inter-web spaces is formed with an inwardly beveled surface 450. The complementary bottom inside surface of the ring section 434 is formed to have step 452 that extends both outwardly and slightly upwardly. FIG. 27 depicts the cross sectional profile of the ring section 434 adjacent the four remaining inter-web spaces. The inner surfaces of this section of the ring section 434 is formed so that the top sections thereof have outwardly directed steps 454. The complementary bottom sections of the ring section 434 have surfaces 456 that taper inwardly from the bottom face of the ring section.

Figure 23:
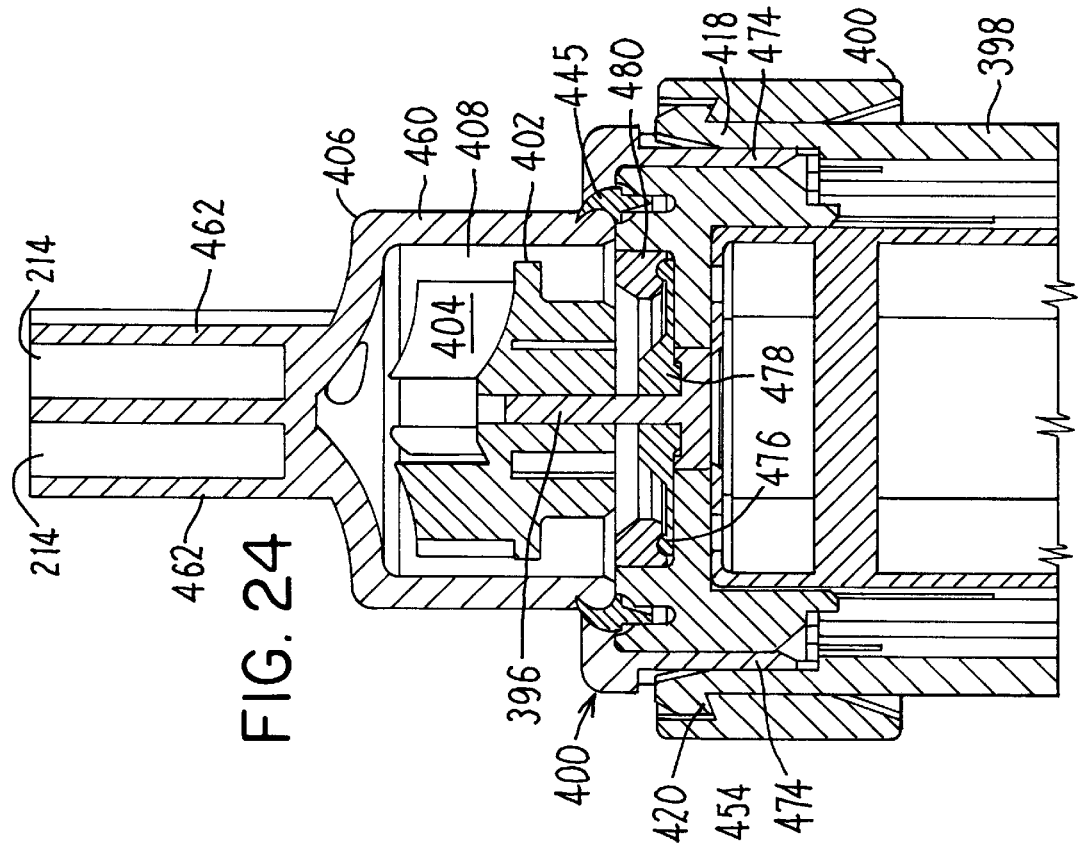
FIG. 23 is a cross sectional view of the pump taken along line 23—23 of FIG. 22.
Figure 24:
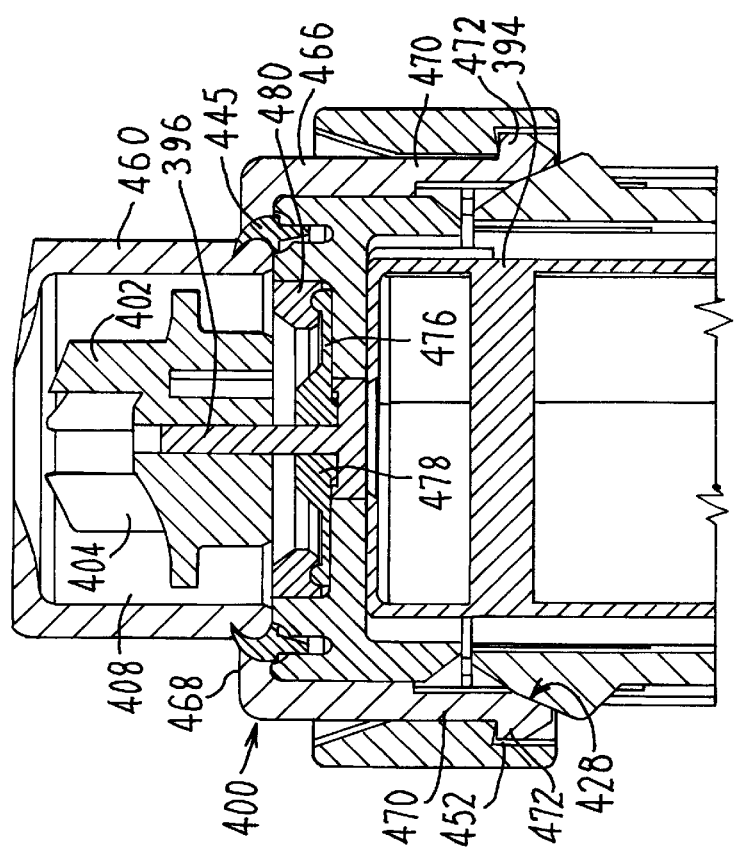
FIG. 24 is a cross sectional view of the pump take along line 24—24 of FIG. 22.
Figure 25A:
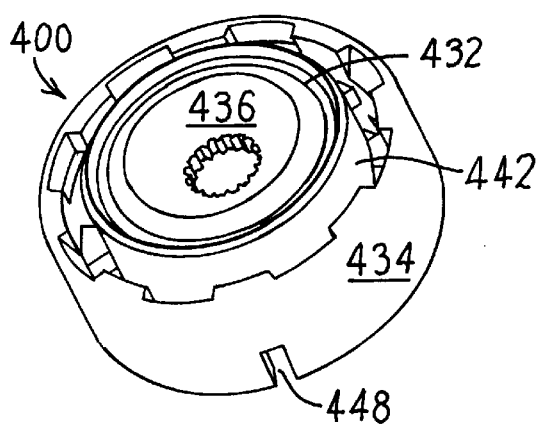
FIGS. 25A and 25B are, respectively, front and back perspective views of the hub of the pump.
Figure 25B:
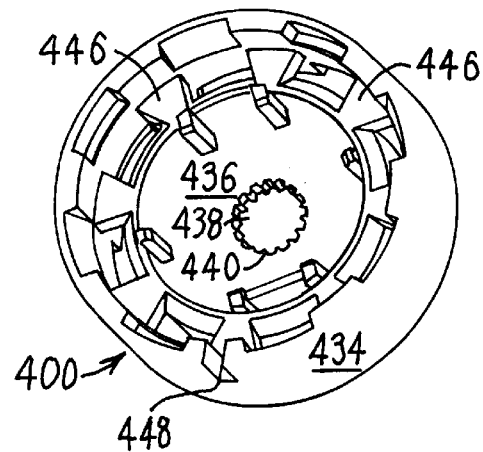

The volute 406, as illustrated in FIGS. 21, 23 and 24, includes a cylindrical main body 460 that defines the pump chamber 408. Integral with the main body 460 are upwardly directed tandem sleeves 462 in which the inlet ports 214 are defined and a laterally extending sleeve 464 that defines the outlet port 216. Extending downwardly for the main body 460 of the volute 406 is a base 466. The base 466 has a diameter that is greater than that of the main body 460. As seen best in FIG. 23, the relatively narrow width laterally extending transition ring 468 between the main body 460 and the base 466 is the portion of the section of the volute 406 that seats against the ring section of the base and the rim 442 of the hub 400.

The base 466 of the volute 406 is formed with four downwardly directed, equidistantly spaced fingers 470. Each finger 470 is formed so that the end thereof has an outwardly directed flange 472. The base 466 also is shaped to have four locking panels 474 that, relative the rest of the base, are inwardly recessed. The locking panels 474 are further formed to extend a slight distance below the bottom edge of the base 466, this distance not being as great as the distance the fingers 470 extend downwardly. The locking panels 474 are located 90° apart from each other so that each panel is located between two fingers 470.

When the pump 40 of this invention is assembled, the motor 394 is seated in the back cap 398 and the hub 400. The hub 400 is fitted over the back cap 398 so that the fingers 418 integral with the back cap extend through the inter-web spaces in the hub and the flanges 420 seat against the steps 434 formed in the hub.

A disc-like lip seal 476 is fitted over the shaft 396 of the motor 394 and is seated against the outer surface of the top 436 of the cap section 432 of the hub 400. It should be noted that in the illustrated version of the invention, while lip seal 476 is generally flat, it is formed to have a thicker center section 478 that defines the opening through which the shaft 394 of the motor 396 extends. A ring like hoop 480 formed of a plastic such as the previously disclosed Cycolac T2502 is compression seated against the inside surface of the rim 442 of the cap section 432 of the hub so as to be disposed against the outer perimeter of lip seal 476. Hoop 480 thus prevents movement of the lip seal 476 once installed. The impeller 402 is fitted directly to the shaft 396 of the motor 394.

Once the impeller 402, the seals 445 and 476 and the hoop 480 are in place, the volute 406 is placed over the hub 400. The volute 406 is oriented so that its fingers 470 extend through the inter-web spaces in the hub 400 in which the fingers 418 integral with the back cap 398 are not already seated. The flanges 472 integral with the fingers 470 of the volute 406 seat against the steps 452 formed in the hub 400.

Once the pump 40 is so assembled, the fingers 418 integral with the back cap 398 are not just seated in the complementary steps formed 454 formed in the hub; fingers 418 are also disposed against the outer surfaces of the locking panels 474 formed integrally with the volute 406. Thus, this arrangement prevents fingers 418 from inadvertently being bent inwardly so as to cause the unintentional separation of the back cap 398 from the rest of the pump. Similarly, the fingers 470 integral with the volute 406 are not just seated in the steps 452 formed in the hub 400. The fingers 470 are also disposed against the outer surfaces 429 of the tabs 428 integral with the back cap 398. The resistive force of the tabs 428 thus prevents the fingers 470 from inadvertently being flexed inwardly so as to cause the unintended separation of the volute from the other components of the pump 40. Thus, the pump 40 of the fluid management pump system 30 of this invention is constructed so that once assembled, its components remain assembled together without the aid of any additional fastening members such as screws that can, due to vibration or inaccurate instillation, work themselves lose. Moreover, the elimination of the additional fastening members likewise eliminates the initial manufacturing steps required to secure the fastening members in place.

Figure 29:
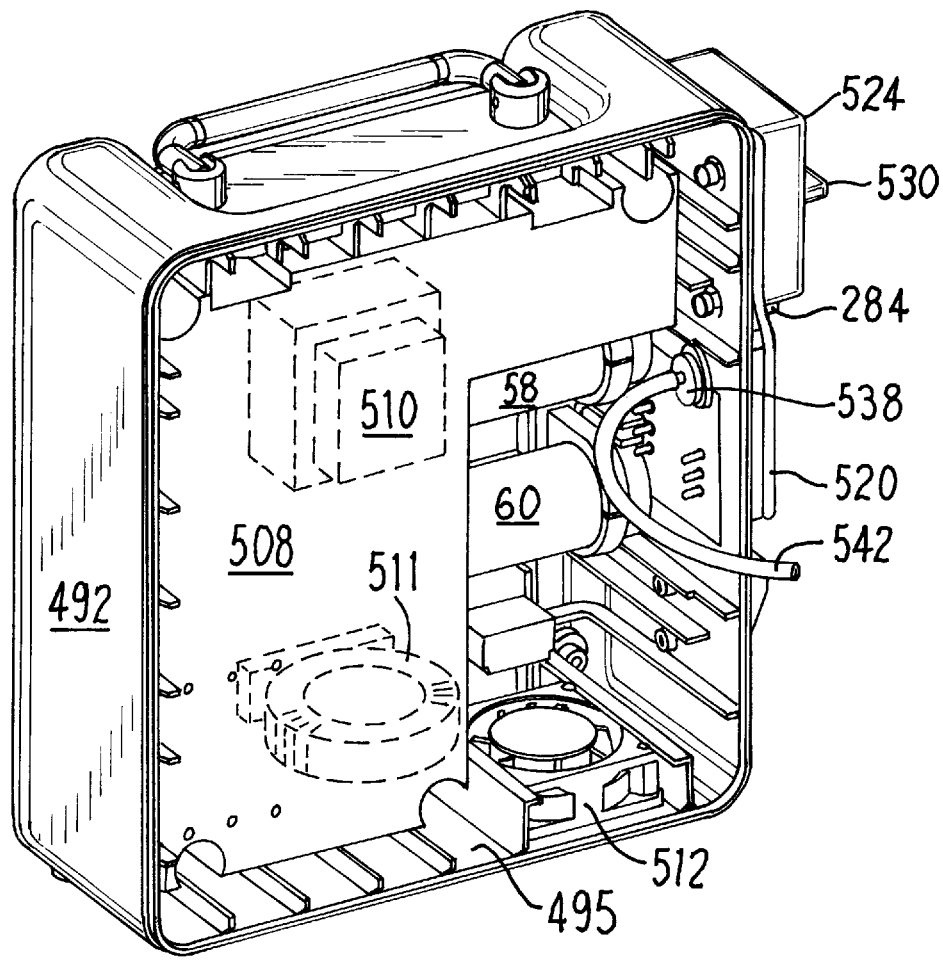
FIG. 29 is a perspective view of the inside of the rear shell of the control unit.

The control unit 50 of the fluid management pump system 30 of this invention is now described by reference to FIGS. 1, 28 and 29. The body of the control unit 50 is formed from an open shell 492 over which a cover 494 is seated. The shell 492 forms the rear of the control unit 50 and is the portion of the control unit to which the cassette 52 is mounted. The cover 494 forms the front face of the control unit 50 and is the structural component of the control unit to which the buttons and switches 64–70 and the displays 71 and 72 are mounted.

Both the shell 492 and the cover 494 are molded from rigid plastic. The inside of both the shell and cover are coated with a thin layer of copper 495, (represented by a stippled coating). When the shell 492 and cover 494 are sealed together to form the control unit, the copper layers 495 contact each other. The copper layers 495 thus collectively form a shield around electric components internal to the control unit 50. This shielded enclosure thus minimizes the extent to which ambient electric signals can affect the components internal to the control unit 50 and the extent to which the control unit itself serves as an electrical noise generator.

The shell 492 has a generally rectangular cross-sectional profile. A pole clamp bracket 496 is secured to the back wall of the shell 492 to facilitate securing the control unit 50 to an intravenous pole 498. A threaded lock rod 500 is provided with the pole clamp bracket 496 to provide the clamping force required to hold the control unit 50 to the pole 498. The head of the lock rod 500 is provided with a knob 502 to facilitate the rotation of the rod. The top of the shell 492 is formed to define a recessed space 504. A pivoting handle 506 is secured to the top of the shell 492 to provide a convenient means for transporting the control unit 50. When use of the handle 506 is not required, the handle is pivoted cited horizontally so as to be seated in the space 504.

The solenoids 58 and 60 that, respectively, control fluid flow through the inflow and outflow tubes 42 and 44 are secured to the inside surface of the back wall of the shell 492. Also secured to inside surface of the back wall of the shell 492 is a power board 508 for the control unit 50. The power board 508 provides the energization signals required to actuate the solenoids 58 and 60, the commutation current that is used to selectively actuate the pump 40 and voltages required to energize the components internal to the control unit 50. It will be further noted that the power board 508 serves as the physical platform to which most of the relatively heavy electrical components internal to the control unit 50 are mounted. For example, in illustrated version of the invention a power transformer 510 and a coil 511, both shown in phantom, are depicted as being mounted to the power board 508. The significance of the placement of these components in the control unit will be discussed hereinafter. A fan 512 is fitted in the base of the shell 492. The fan 512 draws air into the control unit 50 through slotted openings in the base (not shown) to foster the convective cooling of the components internal to the control unit. To accommodate all the components seated inside the shell 492 and to facilitate the fitting of the cassette 52 to the shell, the shell has a depth of approximately 4 inches.

The cassette 52 is fitted against one side of the shell 492. The cassette holder 294 is attached to the side of the shell 492 against which the cassette 52 is seated for supporting the cassette. The cassette holder 294 is a generally solid member that is formed with the two upwardly directed slots 292. The slots 292 serve as the spaces in which the legs 290 of the cassette 52 are seated. Integrally formed with the shell 492 are a pair of opposed restraining rails 520; one rail being located adjacent the open end of the shell, the second rail being located slightly forward the rear of the shell. When the cassette 52 is seated against the shell 492, the restraining rails 520 prevent lateral movement of the cassette.

It will further be seen that the rails 520 have a generally L-shaped profile such that each rail has a lip that extends outwardly, away from the cassette 52. This L-shaped profile allows the rails 520 to serve as gutters that direct any fluid spilled on the top of the control unit 50 away from the interface between the cassette 52 and the control unit.

The cassette 52 is locked in place against the control unit 50 by a latch assembly 524 attached to the side of the shell 492. Latch assembly 524 includes a housing 526 that is located above the restraining rails 522. The lock tongue 284 is slidably mounted in the housing 526. The lock tongue 284 extends downwardly from the housing 526 so as to be located in a space that is both between the restraining rails 522 and located slightly outwardly of the restraining rails. A spring, not illustrated, disposed in the housing 526, places a biasing force on the lock tongue 284 so as to normally maintain the lock tongue in the extended state. A horizontally oriented release tab 530 is attached to the top of the lock tongue 284 and extends outwardly from the housing 526. Release tab 530 provides a mechanical connection for displacing the lock tongue 284 so that the lock tongue can be manual moved into or of the latched or release states.

It will further be seen that the shell 492 is formed so that the flanges 521 integral with the rails 520 actual start a point near the top of the latch assembly 524 and the rails extend downwardly from the where the latch assembly is attached. Thus, as described above, if fluid is spilled on the control unit 50 the rails 520 and flanges 521 cooperate to cause the water to flow away from the interface between the cassette 52 and the control unit 50.

A cassette 52 is secured to the housing 50 by initially seating the legs 290 of the cassette in the slots 292 of cassette holder 294. Due to the angled orientation of the legs 290 of the cassette 52, the cassette initially projects diagonally away the control unit 50. Once the legs 290 are seated, the cassette 52 is then pivoted inwardly so that the latch landing 288 (FIG. 16) on the top of the cassette 52 abuts the exposed end of the lock tongue 284. The manual force applied to pivot the cassette 52 into position is sufficient to overcome the spring force holding the lock tongue 284 in place. Once the cassette is pressed against the surface of the shell 492, the latch tab 280 clears the lock tongue 284. As the latch tab 280 moves beyond the lock tongue 284, the spring internal to the latch assembly 524 returns the lock tongue 284 to the extended state so that the lock tongue holds the cassette 52 in position. Cassette 52 is removed from the control unit 50 by applying an upward force on the release tab 530 to retract the lock tongue 284 away from the latch tab 280 integral with the cassette.

The solenoids 58 and 60 are mounted in the shell 496 so that plungers integral therewith project through holes 532 in the side of the shell 492 so that the plungers can project against the pinch valves 54 and 56, respectively. Returning to FIG. 19, it can be seen that a plunger integral with solenoid 58, plunger 534, is positioned to press against the outer surface of the portion of the cassette cover 272 that forms valve blade 362. In preferred versions of the invention, solenoid 58 is constructed so that plunger 534 is normally extended so that pinch valve 54, the valve that controls flow through the inflow tube 42, is normally in the closed state. (In FIG. 19 plunger 534 is shown in the retracted state; the extended state of plunger 534 and the closed position of valve blade 362 are shown in phantom.) This prevents undesirable back flow of fluid from the surgical site to the pump 40. As will be discussed hereinafter, control unit 50 is configured to only retract plunger 534, open pinch valve 54, when the pump 40 is energized.

Returning to FIG. 20, the plunger integral with solenoid 60, plunger 536, is seen. Plunger 536 is positioned to selectively abut the outer surface of valve blade 364 so as to control the position of pinch valve 56 which regulates the open/closed state of the outflow tube 44. In preferred versions of the invention, plunger 536 is normally in the retracted state so that outflow tube 44 is normally in the open state.

A disc-shaped pressure fitting 538 is seated in a recess formed in the shell 492. The pressure fitting 538, now described by reference to FIGS. 19 and 29, is positioned to be the component integral with the control unit 50 against which the seal 320 associated with the cassette 52 is seated. The pressure fitting 538 is formed from plastic or other material suitable for ensuring that when the seal 320 is pressed against the fitting 538, a gas tight barrier forms therebetween. Pressure fitting 538 is formed with bore 316 located in the center of the fitting. Bore 316 of the pressure fitting 538 is the bore integral with the control unit 50 that is concentric with the feedback fluid outflow bore 310 formed in the cassette 52. Consequently, when the cassette 52 is coupled to the control unit 50, the variable pressure air column in the pressure sensing assembly 76 is placed in fluid communication with the control unit through bore 310 of the pressure fitting 538. An air tube 542, located inside the control unit 50 is connected between the pressure fitting 540 and the transducer 80. Air tube 542 serves as the conduit through which the head of the variable pressure air column is applied to the transducer 80.

A number of metal, conductive surface contacts 544 are mounted to the outside surface of the shell 492 to provide conductive connections between the control unit 50 and the cassette 52. Three surface contacts 544 are arranged in one vertical column below the pressure fitting. A cassette detect circuit 582 (FIG. 30) integral with the electronics internal to the control unit 50 applies a signal to the center one of the surfaces contacts 544 and monitors from which of the other two contacts the signal is received. In this manner the cassette detect circuit 582 determines the position of the ID contact 366 (FIG. 18B) and the type of the tube set 34 coupled to the control unit 50.

The remaining surface contacts 544 are arranged in a second vertical column. This set of surface contacts are positioned to abut the power contacts 380 integral with the cassette 52. This set of surface contacts are connected to the components on the power board 508 that generate the commutation current used to energize the pump 40, (surface contact-to-power board conductors not shown). Thus, the energization signals for actuating the pump are applied to the pump through these surface contacts 544. In the illustrated version of the invention there are three surface contacts 544 associated with the energization signals. The third surface contact 544 is for an optional ground connector.

The cover 494 is secured over the open face of the shell 492 by a set of threaded fasteners, not illustrated, that extend through the shell. The cover 494 is formed out of a single piece of plastic that is shaped to form a display panel 548. The display panel 548 is vertically oriented and extends over approximately the upper 70% of the open face of the shell. The display panel 548 is the portion of the control unit to which the pressure displays 71 and 72 are mounted. Also mounted to the display panel are a set of LEDs 550 for indicating the selected solution flow rate and a set of LEDs 552 for indicating if the tube set 34 and the hand control 74 are engaged with the control unit 50. A third set of LEDs 554 are also mounted to the display panel 548. LEDs 554 are selectively actuated to indicate: the run/stop state of the system 30; if the system is being operated in the lavage mode; a high pressure has been detected at the surgical site; or a potential pressure sensor failure has been detected.

The bottom section of the cover 494 is shaped to form a control panel 556. More particularly the cover 494 so that the control panel 556 extends diagonally outwardly and downwardly away from the adjacent display panel 548. For example, in one version of the invention, the line separating the display panel 548 from the control panel 556 is spaced approximately 4.5 inches from the rear of the control unit 50 and the most forward edge of the control panel 556 is approximately 5.75 inches from the rear of the control unit. The control panel 556 is the surface of the control unit 50 to which the buttons and switches 64–70 are mounted. Owing to the diagonal orientation of the control panel 556, and its position at the bottom of the control unit 50, when medical personnel depress one of the buttons and switches 64–70, the force they impose on the control unit is downwardly oriented towards the base of the pole 498 from which the control unit 50 is suspended. Thus, this force does not serve to destabilize the control unit relative to intravenous pole 498.

A control board 558 is mounted to the inside surface of the cover 494. The control board 558 contains the electrical components 560 (some components shown in phantom) that regulate the operation of the fluid management pump system 30 of this invention. As seen by reference to FIG. 29, mounted to the control board 558 is the pressure transducer 80. The control board 558 also contains the components that respond to the actuation of the switches 64–70. The control board 558, in response to the actuation of the switches 64–70 and the air column pressure monitored by pressure transducer 80, generates a set of control signals to the power board 508. In FIG. 28 one set of control board-power board conductors 562 is shown. The power board 508, in response to the control signals received from the control board 558, selectively generates the signals that actuate the solenoids 58 and 60 and selectively applies energize signals to the pump 40.

Figure 30:
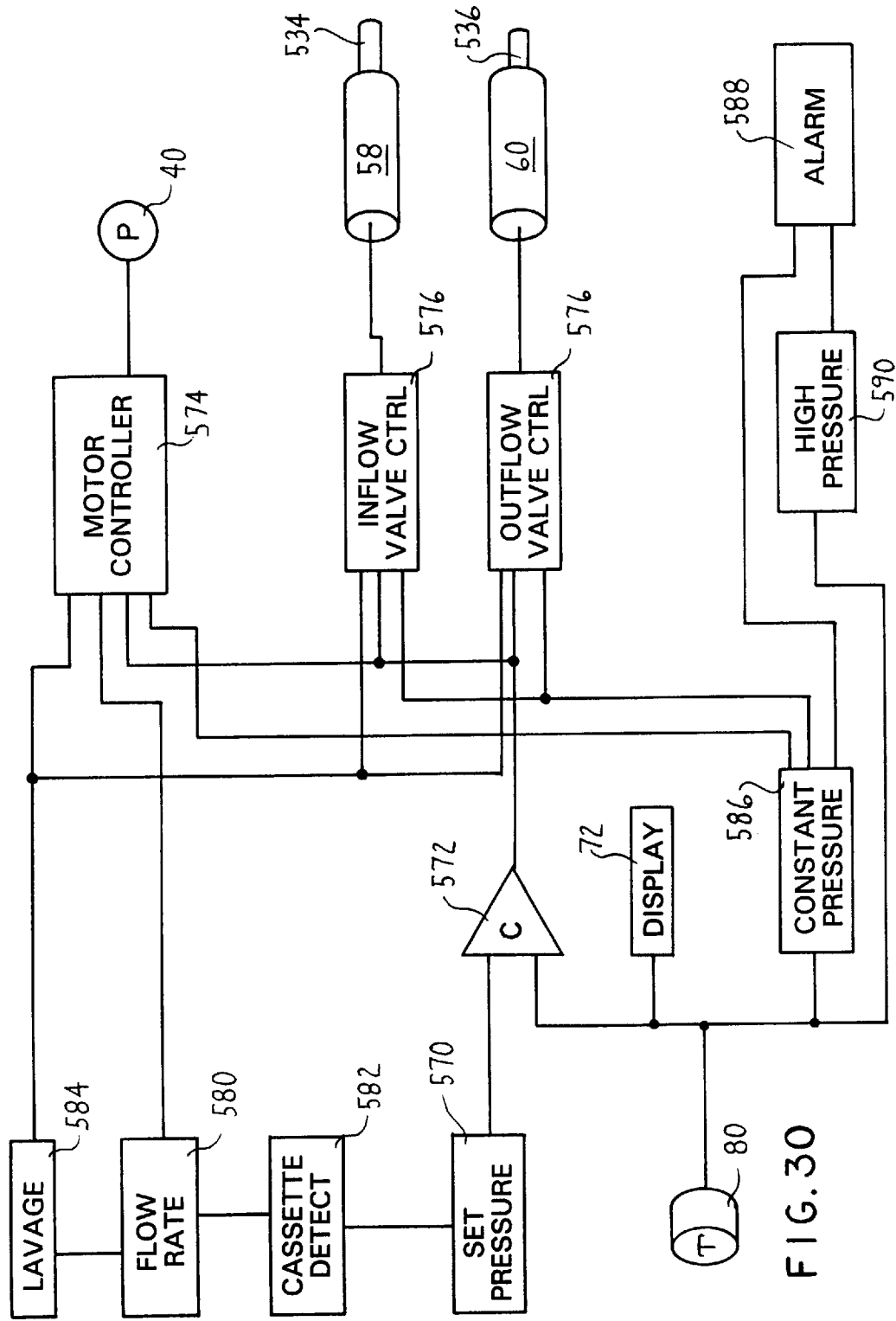
FIG. 30 is a block diagram of the electronics internal to the control unit that control the fluid management pump system of this invention.

FIG. 30 is a block diagram of the main sub-circuits internal to both the power board 508 and the control board 558 that control the actuation of the pump 40 and the valve-setting solenoids 58 and 60. As seen by FIG. 30, control unit 30 includes a set pressure circuit 570. The set pressure circuit 570 is the circuit that responds to the surgeon-entered commands to establish a set pressure for the surgical site to which the sterile solution is applied. The set pressure circuit 570, in response to the surgeon-entered commands, generates an analog signal represented of the selected pressure. Integral with the set pressure circuit 570 is the display 71 upon which the surgeon-entered command is presented.

The analog signal representative of the selected pressure is applied to a hystersis comparator 572. The second input to the hystersis comparator 572 is a signal from the transducer 80 representative of the measured pressure at the surgical site. If the hystersis comparator 572 determines that the actual pressure at the surgical site falls below the selected pressure by a given amount, the comparator asserts a LOW_PRESSURE (LW_PRSR) signal. (The conductors over which the LOW_PRESSURE signal and the other signals identified herein are asserted are presented in FIGS. 31A–31F.) The LOW_PRESSURE signal is applied to three other sub-circuits internal to the control unit: a motor controller 574; an inflow valve controller 576; and an outflow valve controller 578. The motor controller 574 controls the application of the commutation current to the pump 40 and applies the commutation current to the pump in response to receiving the LOW_PRESSURE signal. The inflow valve controller 576 controls the state of solenoid 58 so as to regulate the open/closed state of pinch valve 54. In response to receiving the LOW_PRESSURE signal, inflow valve controller 576 actuates the solenoid 58 so as to cause the retraction of plunger 534 and the opening of the inflow valve 54. The outflow valve controller 578 controls the state of solenoid 60 so as to control the open/closed state of outflow valve 56. When the LOW_PRESSURE signal is received, outflow valve controller 578 actuates solenoid 60 so as to cause the extension of plunger 536 so as to close outflow valve 56 and block fluid flow through outflow tube 44.

Control unit 50 further includes a flow rate controller 580. Flow rate controller 580 responds to the surgeon-entered flow rate control commands so as to generate to the motor controller a signal representative of the selected solution flow rate. The motor controller 574 quantifiably regulates the commutation current applied to the pump in response to the signal received from the flow rate controller 580.

A cassette detect circuit 582 is provided for determining the type of cassette 52 mounted to the control unit 50 and for asserting signals to the other circuits based on the type of cassette. In one version of the invention, it is contemplated that two types of tube sets 34 will be provided, each with its own cassette 52. Specifically, for arthroscopic surgery it is contemplated that a large joint tube set will be provided for supplying sterile solution that is applied to large joints such as knee joints. The second type of tube set 34 is a small joint tube set for supplying sterile solution to small joint surgical sites, such as the wrist region. The cassette detect circuit 582 determines what type of tube set 34 has been fitted to the control unit 52 by monitoring the state of the ID contact 366 integral with the cassette 52 that is part of the tube set.

Once the tube set type determination has been made, the cassette detect circuit 582 asserts appropriate signals to the other components internal to the control unit 50. In the depicted version of the invention, cassette detect circuit 582 asserts a signal to the set pressure circuit 570 in order to establish an initial selected pressure for the surgical site. The cassette detect circuit 582 also asserts a signal to the flow rate controller 580. The flow rate controller 580, in response to the signal received from the cassette detect circuit 582, generates signals that result in the pump 40 being actuated to cause either relatively large or small solution flows.

A lavage circuit 584 responds to the actuation of the lavage button 68. When the lavage button 584 is actuated the lavage circuit asserts a LAVAGE signal that is applied to the motor controller 574, the inflow valve controller 576, the outflow valve controller 578 and the flow rate controller 580. In response to the receipt of the LAVAGE signal, the motor controller 574 immediately applies the commutation current to the pump 40 so as to cause the pump to operate at its highest flow rate for the type of tube set 34 attached to the control unit 50. The inflow valve controller 576 and the outflow valve controller 578, in response to receipt of the LAVAGE signal, respectively open the inflow valve 54 and outflow valve 56 so as to allow fluid flow through the surgical site.

Control unit 50 also has a constant pressure circuit 586. Constant pressure circuit 586 monitors the state of the signal produced by transducer 80. In the event the signal remains constant for an extended period of time, for example, between 2 and 5 seconds, this condition is interpreted by the constant pressure circuit 586 as an indication that there is a potential fault in the pressure sensing assembling 76. If this determination is made, the constant pressure sensing circuit 586 asserts a PRESSURE_FAULT (PRS_FLT) signal to the motor controller 574, and to the inflow and outflow valve controllers 576 and 578, respectively. The motor controller 576, in response to receiving the PRESSURE_FAULT signal, negates the application of the energization signals to the pump. The inflow valve controller 576, in response to receiving the PRESSURE_FAULT signal, denergizes solenoid 58 so as to close pinch valve 54. The outflow valve controller 578, in response to receiving the PRESSURE_FAULT signal, denergizes solenoid 60 so as to open pinch valve 56.

The constant pressure circuit 586 is also connected to an alarm circuit 588. If a potential fault in the pressure sensing components is detected, alarm circuit 588 is actuated to cause the generation of appropriate audible and/or visual indications of the potential fault state of the fluid management system 30.

A high pressure circuit 590 is also connected to receive the output signal from transducer 80. High pressure circuit 590 monitors the output signal from the transducer 80 to see if it exceeds a predefined level, for example a level representative of a pressure greater than 150 mmHg +/– 4 mmHg. If the output signal from transducer 80 exceeds this set reference level, high pressure circuit 590 asserts a signal to alarm circuit 588. The alarm circuit 588, in turn, asserts the appropriate audible or visual notice of the detected pressure state. Also shown in FIG. 30 is the display 72 on which the actual pressure monitored at the surgical site is presented.

FIGS. 31A, 31B, 31C, 31D, 31E and 31F schematically illustrate the components internal to the control unit 50 that regulate the actuation of the pump 40 and the solenoids 58 and 60. Not illustrated, but should be recognized as part of the control unit 50, are the components integral with the power board 558 that generate the +15 VDC, +12 VDC, +5 VDC and –15 VDC voltages required to energize the components of the control unit.

Figure 31:
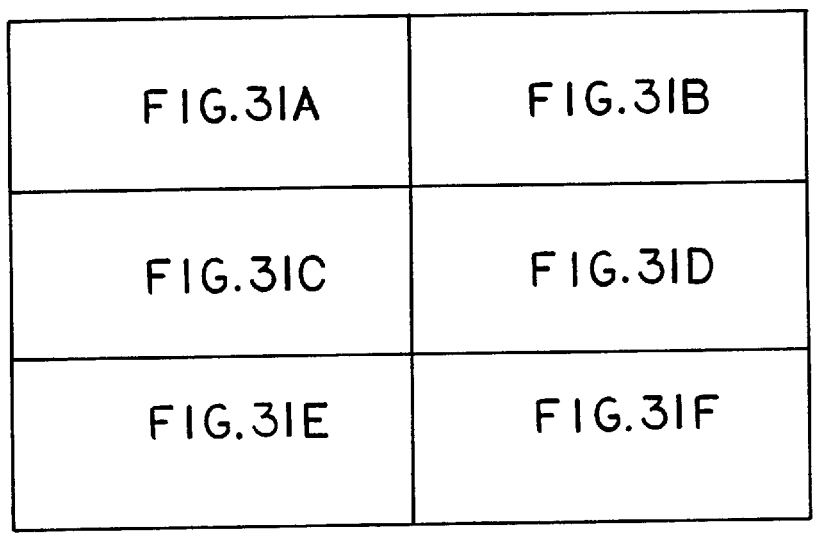
FIG. 31 is an assembly diagram illustrating how
Figure 31A:
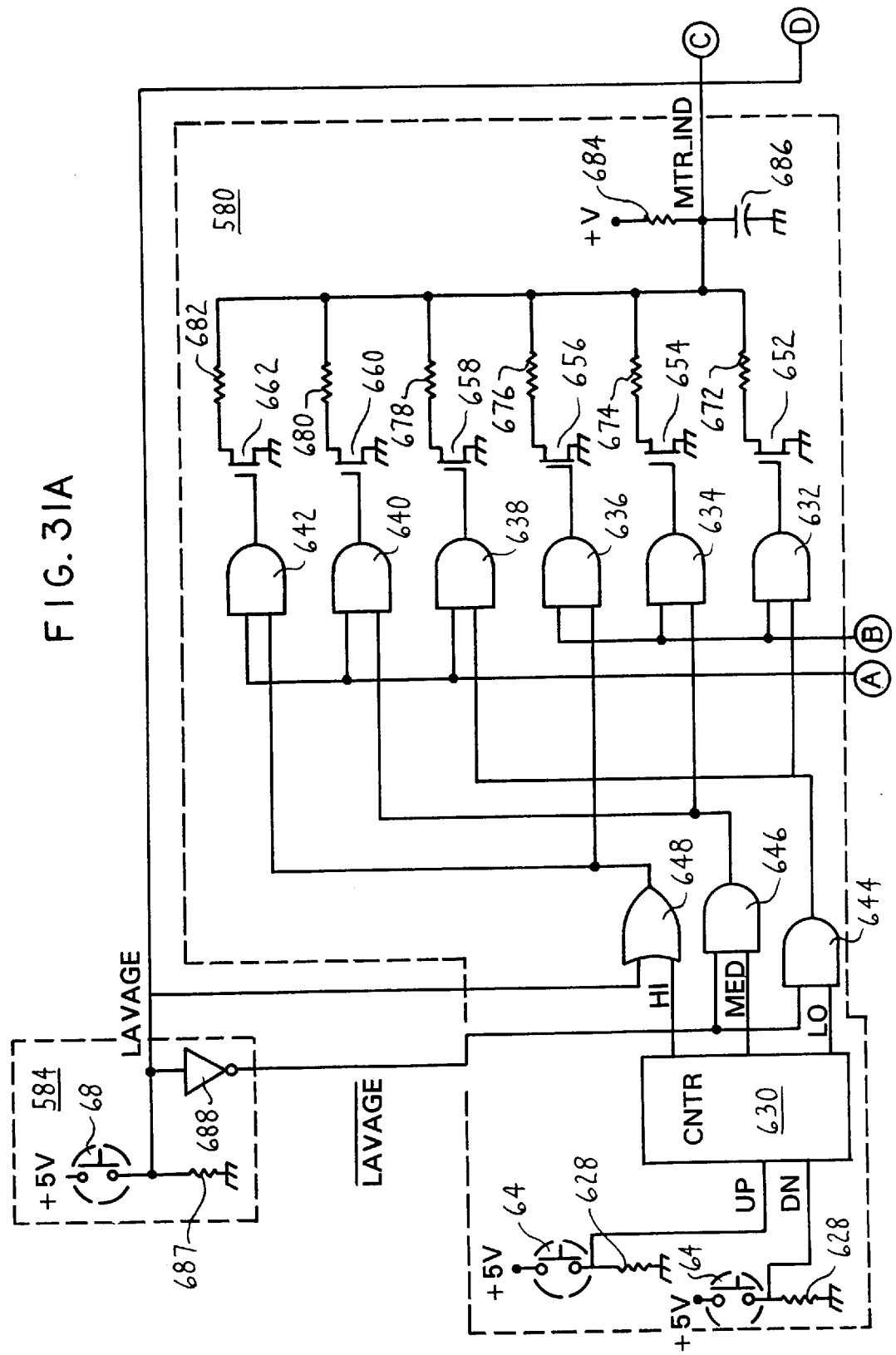
Figure 31B:
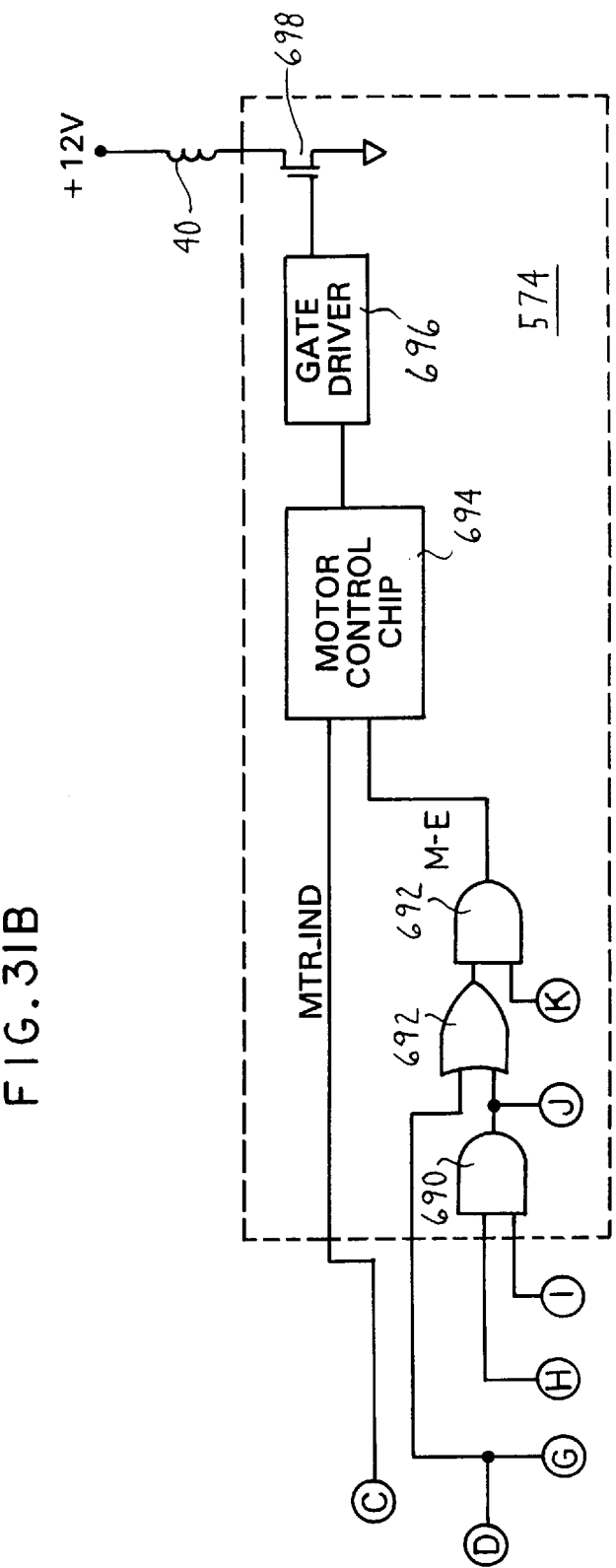
Figure 31C:
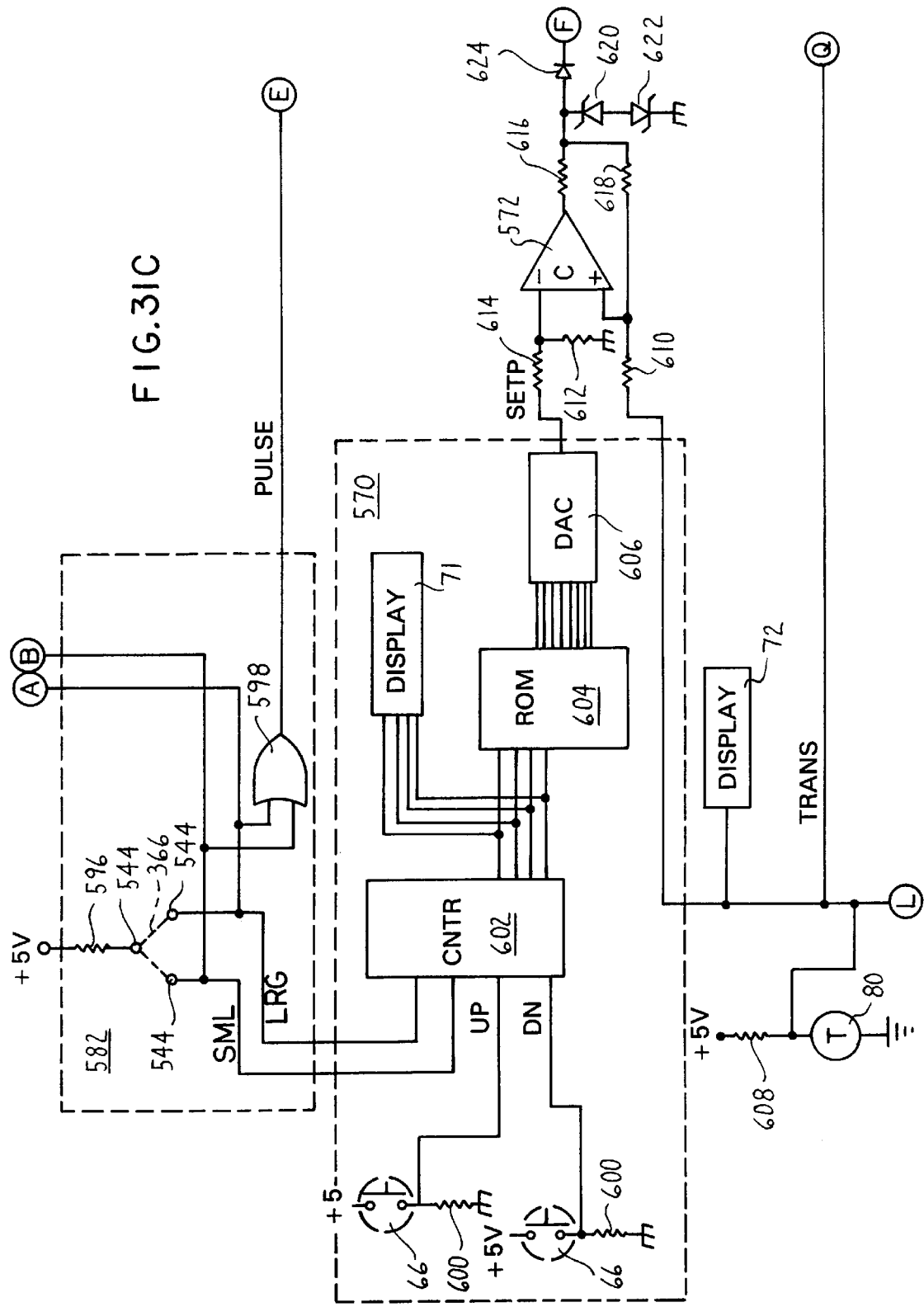

Turning first to FIG. 31C, it can be seen that the cassette detect circuit 582 includes a pull-up resistor 596 that is tied between the +5 VDC voltage source and the center one of the cassette-detect surface contacts 544 on the outside of the shell 492. The signal developed across resistor 596 is applied to one of the other two surface contacts 544 depending on the position of the ID contact 366 internal to the cassette 52 attached to the control unit 50. If the large joint tube set 34 is attached to the control unit 50, the signal is applied to a first one of the complementary surface contacts 544 as a LARGE (LRG) signal. If the small joint tube set is attached to the control unit 50, the signal is applied to the second one of the complementary surface contacts as a SMALL (SML) signal.

An OR gate 598 is connected to the surface contacts 544 over which the LARGE and SMALL signals are selectively asserted. If a tube set 34 is attached to the control unit 50, either one of the LARGE or SMALL signals will be asserted. The OR gate 598 will therefore assert a PULSE signal. The PULSE signal is applied to the other components internal to the control unit 50 to serve as an indication that a tube set has been attached to the control unit 50. As described hereinafter, the components to which the PULSE signal is applied do not energize the components they control unless the PULSE signal is received. This prevents actuation of the control unit 50 unless a tube set 34 is attached. The PULSE signal may also be used to regulate the actuation of one the LEDs 552 to indicate the attachment of a tube set 34 to the control unit 50.

The set pressure circuit 570 includes the surgeon actuated switches 66. Each switch 66 is selectively closed to cause the generation of a pulse signal from across a pull-up resistor 600 that is tied between the +5 VDC source and ground. Not shown are debouncing circuits attached to switches 66 so as to cause single, fixed period, pulses to be generated each time one of the switches is actuated. The switches 66 are connected to an up-down counter 602. One switch 66 is connected to the up-count input of the counter 602; the second switch 66 is connected to the down-count input of the counter.

Also connected to counter 602 are the conductors over which the LARGE and SMALL signals from the cassette detect circuit 582 are selectively asserted. These conductors are tied to different load count input pins of the counter 602. After a tube set 34 is coupled to the control unit 50, either the LARGE or SMALL signal is applied to the counter 602 in order to initially set the counter to count equal to a standard preset pressure for the tube set. In some versions of the invention, the initial pressure for a large joint tube set is between 20 and 40 mmHg and, in more preferred versions, approximately 30 mmHg. In some versions of the invention, the initial pressure setting for a small joint tube set is between and 4 and 25 mmHg and, in more preferred versions, approximately 18 mmHg. By selectively depressing the switches 66, the surgeon can adjust the selected pressure up or down from the initial setting.

Counter 602 asserts a parallel, multi-bit signal representative of its stored count. The signal asserted by counter 602 is applied to the display 71 so as to cause the visual indication of the selected pressure to be presented, (display drivers not illustrated.) The signal produced by counter 602 is also applied to a read-only memory (ROM) 604, such as an electronically programmable read-only memory. More particularly, the signal from the counter 602 is applied to the ROM 604 as a ROM address. The ROM retrieves from the designated address location a multi-bit digital signal representative of the designated pressure.

The multi-bit signal from the ROM 604 is applied as a parallel signal to a digital-to-analog converter (DAC) 606. The DAC 606 converts the signal into an analog SETP signal representative of the surgeon selected pressure for the surgical site. The SETP signal is then applied to the hystersis comparator 572.

The signal from the transducer 80 is the second signal applied to the hystersis comparator 572. In FIG. 31C transducer is represented as a variable resistance type device that changes resistance as a function of the pressure applied thereto. It should, of course be recognized that other types of transducers may be employed such as piezo-electric devices that generate different voltages as a function of the applied pressure. In the depicted version of the invention, transducer 80 is shown as connected between a resistor 608 and ground. A voltage is applied to the opposed end of resistor 608 so that resistor 608 and the transducer 80 function as a voltage divider. The signal present at the junction of resistor 608 and the transducer 80 is monitored as TRANS signal representative of the monitored pressure at the surgical site.

One location to which the TRANS signal is applied is the display 72. Based on the level of the TRANS signal, display 72 generates a visual presentation of the monitored liquid-state fluid pressure at the surgical site (display drivers not shown).

The TRANS signal is also the signal that is applied to the hystersis comparator 572. More particularly, it can be seen that the TRANS signal is applied to the inverting input of the comparator 572 through a resistor 610. A resistor 612 is tied between the inverting input of the comparator and ground. The SETP signal from the set pressure circuit 570 is applied to the non-inverting input of the comparator 572 through a resistor 614. The output signal from the comparator 572 is applied directly to a resistor 616. A feedback resistor 618 is tied between the end of resistor 616 distal from the comparator 572 and the non-inverting input. The junction of resistors 616 and 618 is the point at which the LOW_PRESSURE signal is asserted.

Collectively, resistors 610–618 are selected to provide a hystersis overshoot for the signal produced by the comparator. In one versions of this invention, this hystersis is set so as to cause the comparator 572 to assert the LOW_PRESSURE signal until the actual pressure rises to 3 mmHg above the selected pressure; on the down cycle, the hystersis is set to prevent the LOW_PRESSURE signal from being asserted until the actual pressure fall to 3 mmHg below the selected pressure. This hystersis prevents needless on-off cycling of the pump 40 and valves 54 and 56.

Series connected reverse and forward biased zener diodes 620 and 622, respectively are connected between the resistor 616-resistor 618 junction and ground. Diodes 620 and 622 clip the LOW_PRESSURE signal to maintain the voltage at appropriate level for downline logic components to which it is applied. The LOW_PRESSURE signal is applied to the downline components through a forward biased diode 624.

Turning to FIG. 31A, the flow rate controller 580 is now described in more detail. The switches 64 that are depressed by the surgeon control the assertion of digital pulses as represented by the switches being tied between the +5 VDC voltage and pull-up resistors 628. Not shown are debouncing circuits attached to switches 64 so as to cause single, fixed period pulses to be generated each time one of the switches is actuated. The pulses generated by the switches are applied to an up-down counter 630. One switch 64 is connected to the up-count input of the counter 630; the second switch 64 is connected to the down-count input of the counter.

Counter 630 has a set of output pins over which a parallel count signal is normally generated. In the depicted version of the fluid management system 30 of this invention, each output pin serves as the output terminal from which a signal represented of selected solution flow rate is generated by the counter 630. More particularly, depending on the number and type of input pulses applied to the counter 630, the counter will assert a HI signal representative of a high solution flow rate, a MED signal representative of a medium solution flow rate or a LO signal representative of a low solution flow rate.

The HI, MED and LOW signals are applied as input signals to a set of AND gates 632–642. More particularly, the LOW signal is applied to AND gates 632 and 638 through an AND gate 644, the second input of AND gate 644 will be discussed hereinafter. The MED signal is applied to AND gates 634 and 640 through an AND gate 646, the second input of AND gate 646 being discussed hereinafter. The HI signal is applied to AND gates 636 and 642 through an OR gate 648, the second input of OR gate 648 being discussed hereinafter.

The SMALL signal from the cassette detect circuit 582 is applied as the second input to AND gates 632, 634 and 636. The LARGE signal from the cassette detect circuit 582 is applied as the second input to AND gates 638, 640 and 642. Depending on which of the SMALL or LARGE signals and which of the HI, MED or LO signals are asserted, only one of the AND gates 632, 634, 636, 638, 640 or 642 asserts a high signal. The outputs of AND gates 632–642 are tied to the gates of FETs 652–662, respectively. The drain of each FET 652–662 is tied to ground. The sources of FETs 652–662 are tied to separate resistors 672–682, each of which has a different resistance. The opposed ends of each of the resistors 672–682 are tied to a common resistor 684.

The opposite end of resistor 684 is tied to the +5 VDC voltage. Thus resistor 684 forms a voltage divider with the one of the resistors 672, 674, 676, 678, 680 or 682 that is tied to ground. Thus, the voltage present at the junctions forming the voltage divider is determined by which one of the AND gates 632, 634, 636, 638, 640 or 642 asserts a high signal. The voltage present at this junction is applied to the motor controller 574 as a MOTOR_INDUCTION (MTR_IND) signal for controlling the speed of the pump 40. In the illustrated version of this invention, spikes are removed from the MOTOR_INDUCTION signal by a capacitor 686 tied between the center junction of the voltage divider and ground.

The HI, MED, and LO signals are also applied to a set of transistor switches, not illustrated. The transistor switches control the actuation of the LEDs 550 so that the LEDs 550 provide an indication of the current, surgeon selected flow rate.

The lavage circuit 584 includes the lavage button 68 which is shown as being selectively depressed to causing a +5 VDC signal to develop across a resistor 687. This signal is the LAVAGE signal. An invertor 688 is tied to the conductor over which the LAVAGE signal is asserted to produce a $\overline{\text{LAVAGE}}$ signal. The $\overline{\text{LAVAGE}}$ signal is applied to AND gates 644 and 646 so as to be the second input to these AND gates.

During normal operation of the system 30, when system is not being operated in the lavage mode, the $\overline{\text{LAVAGE}}$ signal, which is asserted high, is asserted. Thus if counter 630 asserts either the LO or MED flow signals, these signals will be gated through AND gates 644 and 646, respectively. The LAVAGE signal is applied to the second input of OR gate 648. During normal operation of the system 30, the LAVAGE signal, which is asserted high, is not asserted.

If however, the surgeon places the system 30 in the lavage mode, the LAVAGE signal is asserted and the $\overline{\text{LAVAGE}}$ signal is negated. The application of the LAVAGE signal to OR gate 648 causes a pseudo HI signal to be asserted by the OR gate. Simultaneously, the negation of the $\overline{\text{LAVAGE}}$ signal serves block the assertion of the LO and MED signal from AND gates 644 and 646, respectively.

Also part of the lavage circuit 584 but not shown is a transistor switch that is regulated by the LAVAGE signal. The transistor switch actuates one of the LEDs 554 to provide a visual indication that the system 30 is being operated in the lavage mode.

Motor controller 574, as seen in FIG. 31B, includes an AND gate 690 to which the LOW_PRESSURE signal from the hystersis comparator 572 is applied. The second input to AND gate 690 is the PRESSURE_FAULT signal from the constant pressure circuit 586. Since the PRESSURE_FAULT signal is asserted low, unless there is a detected fault, the signal normally presented to the second input of AND gate 676 is high.

The output signal from AND gate 690 is applied as one input to an OR gate 692. The output signal from AND gate 690 is also applied to the constant pressure circuit for a purpose to be discussed hereinafter. The second input to OR gate 692 is the LAVAGE signal. The output signal from OR gate is a MOTOR_ENABLE (M_E) signal that is asserted whenever the pump 40 is to be actuated. The MOTOR_ENABLE signal is applied to a motor control chip 694 through an AND gate 692. The second input to AND gate 692 is the PULSE signal from the cassette detect circuit 582. The AND gate 692 thus prevents the forwarding of the MOTOR_ENABLE signal to the motor control chip 694 unless the cassette detect circuit 582 asserts a PULSE signal indicating a tube set 34 is attached to the control unit 50.

The motor control chip 694 is any suitable chip for providing a signal for controlling the application of the commutation current to a DC motor. One suitable motor control chip 694 is manufactured by MicroLinear as ML4823. The motor control chip 694 receives as a second input the MOTOR_INDUCTION signal from the flow rate controller 580. Based on the state of the MOTOR_ENABLE signal, the motor control chip 682 selectively asserts control signals that cause a commutation current to be applied to the pump 40. The energization signals that are applied to the pump 40 are pulsed DC signals. More particularly the signals have a variable frequency pulses, in that each pulse has a variable period "current on" components and a fixed period "current off" component. The period of the "current on" component of each pulse, and therefore the overall pulse period and pulse frequency is established by the motor control chip 682 based on the level of the MOTOR_INDUCTION signal.

The MOTOR_INDUCTION signal can be set to cause the pump to operate at any desired rate. In one version of the invention, when a large joint tube set is installed, at the high flow rate for the pump 40 is 1600 ml/min±200 ml/min, the medium flow rate is 1000 ml/min±200 ml/min and the low flow rate is 500 ml/min±200 ml/min. When the small joint tube set is installed, the high flow rate for the pump 40 is set to be 300 ml/min±150 ml/min, the medium flow rate is 100 ml/min±50 ml/min and the low rate is between 15 and 50 ml/min and usually approximately 25 ml/min.

The output signal from the motor control chip 694 is applied to a gate driver 696. The gate driver 696, in response to the signal from the motor control chip 682 selectively applies a bias signal to the gate of a power FET 698 integral with the power board 558. As seen in FIG. 31B, the motor 394 internal to the pump, (represented by a coil) is normally tied to the +12 VDC source. The FET 698, in response to the bias signal applied thereto, selectively ties the motor 394 to ground so as to cause commutation current flow through the motor.

Figure 31D:
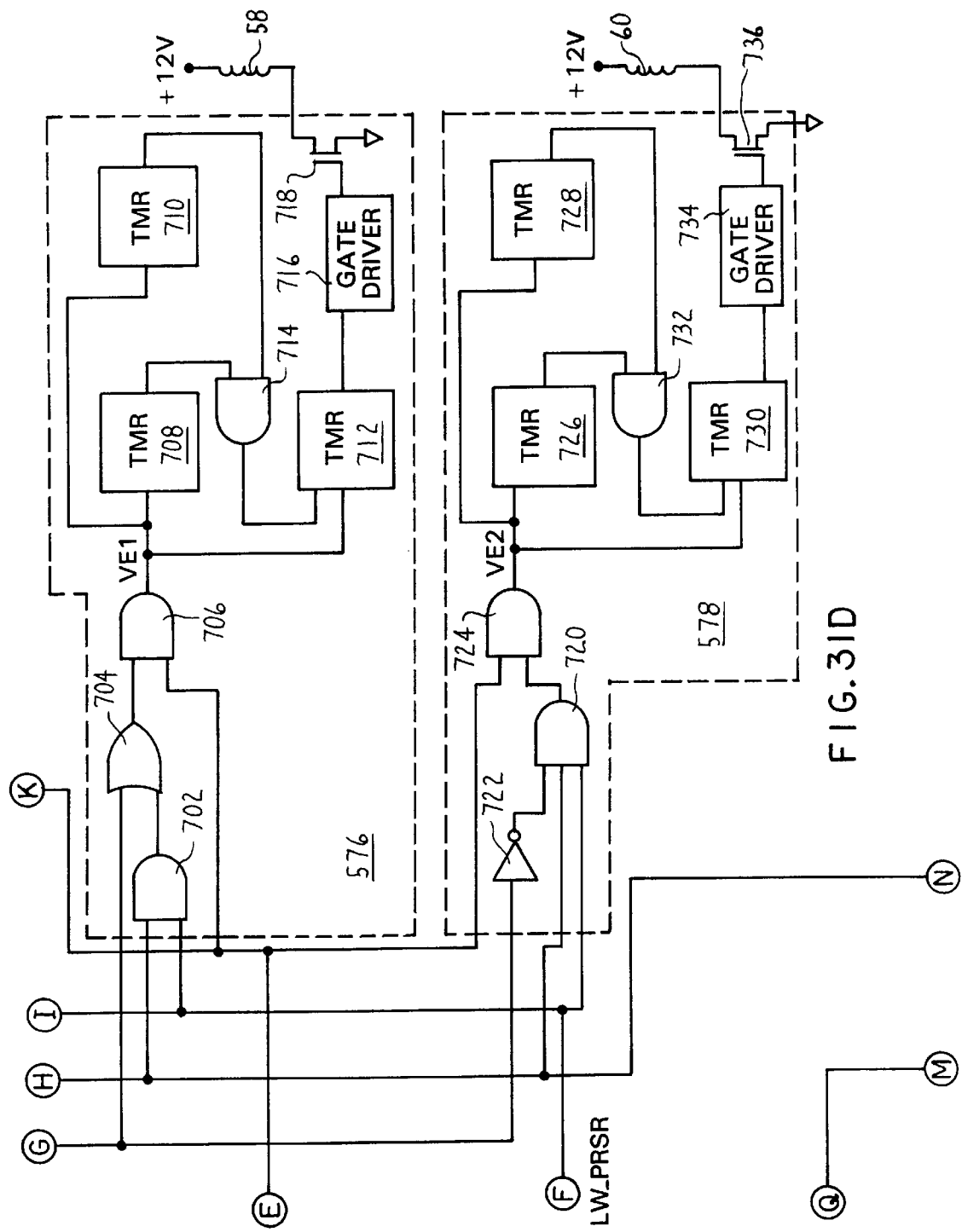
Figure 3I:
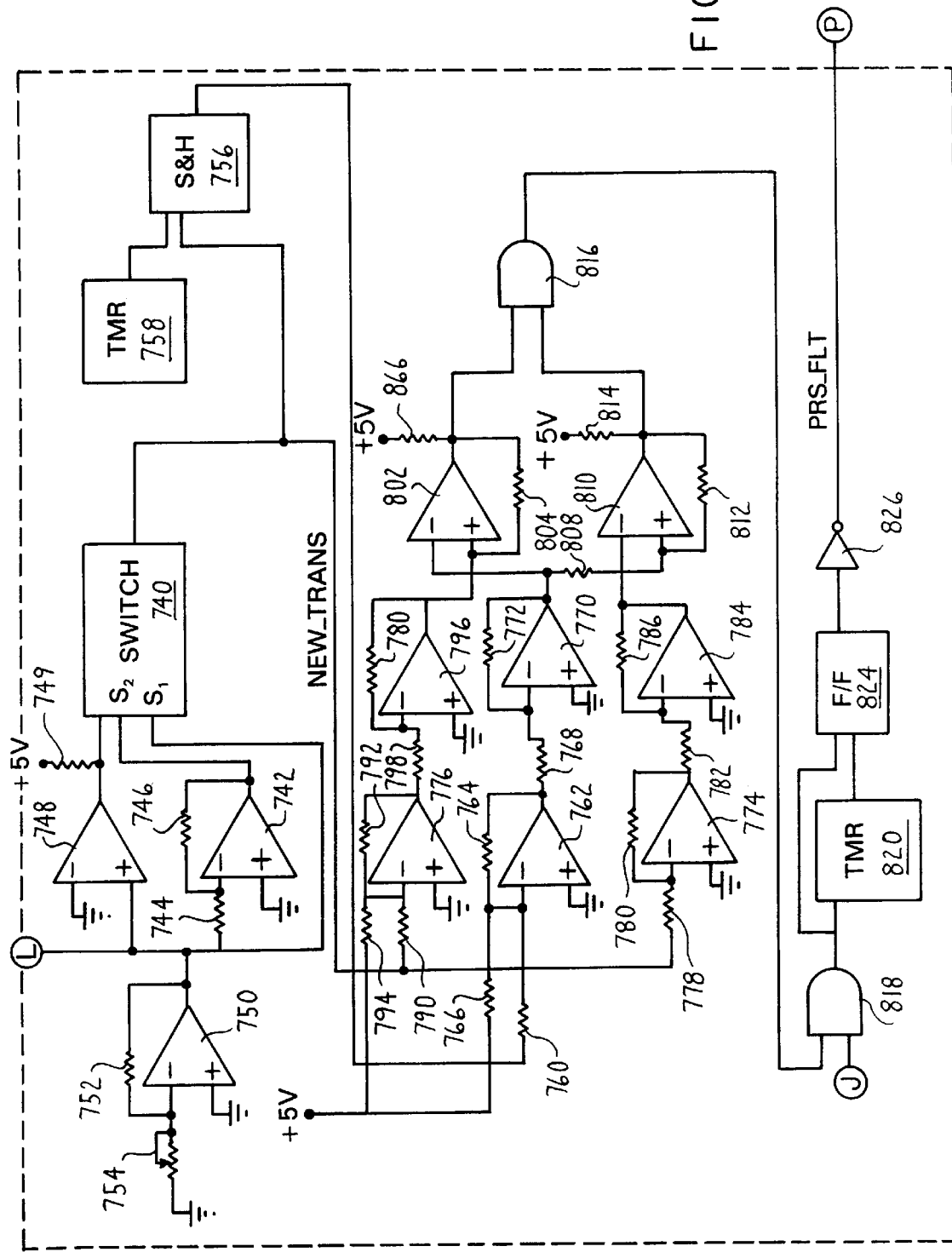
FIG. 3A is a longitudinal cross sectional view of the pressure sensing cannula.
Figure 3I:
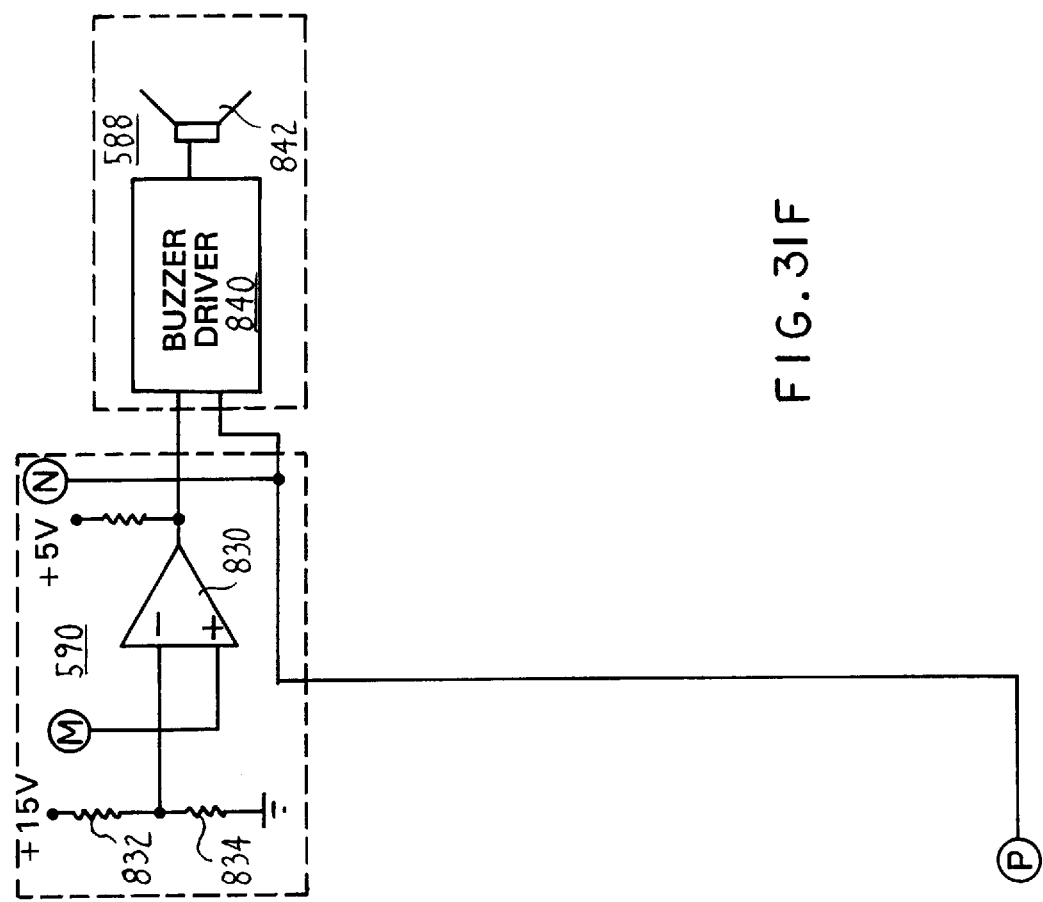

The inflow valve controller 576, now described by reference to FIG. 31D, includes an AND gate 702. The two inputs to AND gate 702 are the LOW_PRESSURE signal from the hysteresis comparator 572 and the asserted-low PRESSURE_FAULT signal from the constant pressure circuit 586. The output signal from AND gate 702 is applied to an OR gate 704. The second input to OR gate 704 is the LAVAGE signal. The output signal from OR gate 704 is a VALVE_1_ENABLE (VE1) signal. The VE1 signal is gated through an AND gate 706. The second input to AND gate 706 is the PULSE signal. The AND gate 706 thus prevents downline processing of the VALVE_1_ENABLE signal unless, as indicated by the assertion of the PULSE signal, a tube set 34 is attached to the control unit 50.

The VALVE_1_ENABLE signal, when asserted, is applied to three timers 708, 710, and 712 that collectively generate signals to the solenoid 58 so as to cause the retraction of plunger 534. (In FIG. 31D solenoid 58 is represented as a coil.) Timer 708 is configured to generate a constant output pulse as long as the VALVE_1_ENABLE signal remains asserted. Timer 710 is configured to assert a pulse of fixed length based on the initial receipt of the VALVE_1_ENABLE signal. In particular this pulse is of a length between 300 msec and 800 msec and in more preferred versions of the invention, approximately 510 msec. Timer 712 is configured to generate on-off pulses that have an "on" duty cycle of approximately 40 to 60% of the pulse width.

The output signals from timer 708 and 710 are applied to the inputs of an AND gate 714. The output signal from AND gate 714 is applied to a trigger input of timer 712. Consequently, once the VALVE_1_ENABLE signal is initially asserted, the output signals from timers 708 and 710 combine at AND gate 714 to present a trigger signal to timer 712. Timer 712, in response to receiving this trigger signal, asserts a constant, high output signal. This constant signal ensures that during an initial, valve trigger, period of the valve actuation cycle, enough current will be applied to the solenoid 58 to cause the retraction of plunger 534.

At the end of the valve trigger period, the output signal from timer 710 is negated so as to cause the like negation of the output signal from AND gate 714. The negation of the trigger signal to timer 712 causes the inflow valve controller 574 to enter a second, valve hold, period of the valve actuation cycle. During the valve hold period of the valve actuation cycle the output from timer is the on-off pulse stream. As will be discussed hereinafter this pulse stream causes enough current to be applied to the solenoid 58 so as to cause the solenoid to hold the plunger 534 in the retracted state.

The output signal from timer 712 is applied to a gate driver 716. The gate driver 716, in turn generates a bias current to the drain of a high current switching FET 718. The +12 VDC from the power board 558 is applied to one end of the solenoid 58. The other end of the solenoid 58 is tied to ground through the FET 718. During the valve trigger period of the valve actuation cycle, owing to the continuous on state of the FET 718 approximately 2 Amps are applied to the solenoid 58 so as to cause the retraction of plunger 534. During the valve hold period, owing to the rapid on-off cycling of the FET 718, only approximately 0.9 Amps are applied to the solenoid 58. This reduction in the amount of power applied to the solenoid 58 reduces the extent to which the solenoid generates thermal energy that unnecessarily heats the control unit 50.

The outflow valve controller 578 includes a three-input AND gate 720. A first one of the inputs to AND gate 720 is the conductor over which the LOW_PRESSURE signal is asserted. A second input to AND gate 720 is the conductor over which the asserted-low PRESSURE_FAULT signal is asserted. A third input to AND gate 720 is an inverted version of the LAVAGE signal. This signal is provided by an invertor 722 to which the LAVAGE signal is applied. The inputs to AND gate 720 thus ensure that the AND gate 720 will only assert a high signal when the hystersis comparator 572 provides an indication that the surgical site pressure is below the surgeon-selected pressure, that the constant pressure has not detected a potential fault in the pressure sensing components and the surgeon has not indicated that the system is to be operated in the lavage mode. The signal asserted by AND gate 720 is the VALVE_2_ENABLE (VE2) signal.

The VALVE_2_ENABLE signal from AND gate 720 is itself gated through an AND gate 724. The second input to AND gate 724 is the PULSE signal from the cassette detect circuit 582. The gating provided by AND gate 724 thus prevents the signal that actuates the outflow valve from being forwarded downline unless there actually is a tube set 34 attached to the control unit 50.

The output signal from AND gate 724 is applied to three timers 726, 728, and 730. Timers 726, 728 and 730 operate in the same manner as timers 708, 710 and 712, respectively, discussed with respect to the inflow valve controller 576. The output signals produced by timers 726 and 728 are gated by AND gate 732. The output signal of AND gate 732 is applied to the trigger input of timer 730.

The output signal produced by timer 730 is applied to a gate driver 734. The gate driver 734 controls the on/off state of a FET 736 that regulates the energization of solenoid 60 (solenoid 60 represented by a coil.) Owing to the signals asserted by the timers 726, 728 and 730, for approximately the first 510 msec after the VALVE_2_ENABLE signal is applied thereto, FET 736 is held continuously on. This causes a 2 Amp current to be applied to solenoid 60; this current is sufficient to force the extension of plunger 536. If the VALVE_2_ENABLE signal remains asserted after this initial trigger period, FET 736 is pulsed on and off so as to result in the application of a 0.9 Amp current to the solenoid 60. This later current is sufficient to hold the plunger 536 in the extended position and further serves to reduce the unnecessary production of heat by the solenoid. 590

The constant pressure circuit 586, now described by reference to FIG. 31E, includes an analog signal switch 740, (a two-input multiplexer.) A first one of the input signals applied to switch is the TRANS signal direct from the transducer 80. The second input to switch 740 is an inverted version of the TRANS which is produced by amplifier 742. In order to produce the inverted TRANS signal a resistors 744 is attached to the inverting input of the amplifier 742 and a resistor 746 is tied between the output and inverting input of the amplifier 742 that are equal to each other.

Switch 740 is set by a signal that is representative of the positive/negative state of the TRANS signal. This signal is produced by comparator 748. The TRANS signal is applied directly to the noninverting input of comparator 748. The inverting input of comparator 748 is tied to ground. A pull-up resistor 749 is tied between the output of the comparator and the +5 VDC voltage source.

Consequently, switch 740 outputs one of the two signals applied thereto. Whenever the TRANS signal is positive, the TRANS signal is the output signal. Whenever the TRANS signal is negative, the inverted trans signal from amplifier 742 is the output signal. Consequently, in this manner the output signal from switch 740 is always the absolute value of the TRANS signal, hereinafter the NEW_TRANS signal. The reason the NEW_TRANS signal is positive is that the downline components of the constant pressure circuit 586 are configured to only process positive signals. In a surgical suit where the fluid management system 30 of this invention is employed it is often a practice to maintain the suite at a slight negative pressure. Some transducers 80 may, in a negative pressure environment, respond to the exposure of a negative pressure or nearby ventilating system suction equipment by generating negative signals. Switch 740 and the associated components thus ensure that the downline components that monitor the state of the signal produced by the transducer 80 only have to process positive signals.

In the depicted version of the invention, the TRANS signal received by switch 740, amplifier 742 and comparator 748 may actually be an adjusted TRANS signal. A voltage offset assembly, represented by amplifier 750, feedback resistor 752 and adjustable resistor 754, can be set to provide an offset voltage to the TRANS signal.

The NEWTRANS signal is applied to a sample-and-hold circuit 756. The sample-and-hold circuit 756 receives pulses from a timer 758 that cause the circuit 756 to, once every 1.2 second sample the NEWTRANS signal and asserts the sampled signal as an output signal for a 1.2 second period. The sampled signal is applied to the inverting input of an amplifier 762 through a resistor 760. The noninverting input of amplifier 762 is tied to ground. A feedback resistor 764, having the same resistance as resistor 760 is tied between the output of amplifier 762 and the inverting input. A fixed offset voltage is applied to the inverting input through a resistor 766 that is tied between the +5 VDC source and the inverting input of amplifier 762.

The output signal from amplifier 762 is applied to the inverting input of an amplifier 770 through a resistor 768. The noninverting input of amplifier 770 is tied to ground. A feedback resistor 772 having the same resistance as resistor 768 is tied between the output of amplifier 770 and the inverting input. Thus, the output signal from amplifier 770 is the sampled-and held signal NEWTRANS signal from the sample-and-hold circuit 756 as modified by the offset voltage as applied from resistor 766. In some versions of the invention this voltage is 30 mV above the sample-and-held voltage.

The NEWTRANS signal, in addition to being applied to the sample-and-hold circuit 756, is applied to two amplifiers 774 and 776. The NEWTRANS signal is applied to the inverting input of amplifier 774 through a resistor 778. The noninverting input of amplifier 774 is tied to ground. A feedback resistor 780 having the same resistance as amplifier 778 is tied between the output of amplifier 774 and the inverting input. The inverted NEWTRANS signal produced by amplifier 774 is applied to the inverting input of an amplifier 784 through a resistor 782. The noninverting input of amplifier 784 is tied to ground. A feedback resistor 786 having the same resistance as resistor 782 is tied between the output of amplifier 784 and the inverting input. Consequently, since amplifier 784 inverts the inverted NEWTRANS signal it can be said that amplifier 784 thus produces a regenerated NEWTRANS signal.

The NEWTRANS signal is applied to the inverting input of amplifier 776 through a resistor 790. The noninverting input of amplifier 776 is tied to ground. A feedback resistor 792 having the same resistance as resistor 790 is tied between the output of amplifier 776 and the inverting input. An offset voltage is applied to amplifier 776 through a resistor 794 that is tied between the +5 VDC voltage source and the inverting input of amplifier 776. The output signal of amplifier 776 is inverted by an amplifier 796. More particularly, the output signal from amplifier 776 is applied to the inverting input of amplifier 796 through a resistor 798. The noninverting input of amplifier 796 is tied to ground. A feedback resistor 800 having the same resistance as resistor 798 is tied between the output of amplifier 796 and its inverting input. Amplifier 796 thus produces an output signal based on the NEWTRANS signal as modified by the offset voltage. In some versions of the invention this offset voltage is approximately 60 mV.

The offset NEWTRANS signal from amplifier 796 is applied to the noninverting input of a comparator 802. The offset sampled-and-held signal from amplifier 770 is applied to the inverting input of comparator 802. A feedback resistor 804 is tied between the output of comparator 802 and its noninverting input. A pullup resistor 806 is tied between the +5 VDC voltage source and the output of the comparator 802.

The offset sampled-and-held signal from amplifier 770 is also applied to the noninverting input of a comparator 810 through a resistor 808. The regenerated NEWTRANS signal from amplifier 784 is applied to the inverting input of comparator 810. A feedback resistor 812 is tied between the output of comparator 810 and its noninverting input. A pullup resistor 814 is tied between the +5 VDC voltage source and the output of comparator 810.

The output signals produced by both comparators 802 and 810 are applied as inputs to an AND gate 816. If for a 1.2 second period the NEWTRANS signal does not drop 30 mV, comparator 802 during that period will assert a high signal. If during the same period, the NEWTRANS signal does not rise 30 mV, comparator 810 will assert a high signal. If both comparators 802 and 810 assert high signals AND gate 816 will likewise assert a high signal. The assertion of a high signal by AND gate 816 is the first indication that the TRANS signal produced by transducer 80 has not undergone its normal variation as expected of the signal.

The output signal produced by AND gate 816 is supplied as one input to an AND gate 818. The second input to AND gate 818 is the output signal from AND gate 690 of the motor controller 574. The signal from AND gate 690 when asserted high, is recognized by the constant pressure circuit 586 as an indication that the system 30 is being operated in the normal, pressure sensitive mode as opposed to the lavage mode. Should both inputs to AND gate 818 be high, AND gate 818 will assert a high signal that serves as an indication that the system 30 is being operated in the normal mode and there is an initial possible of a pressure sensing fault.

The output signal generated by AND gate 818 is applied to the reset pin of a timer 820. Timer 820 is configured to generate a wait pulse, that is some preferred versions of the invention is between 3 to 5 seconds in length and, in more preferred versions of the invention, 4 seconds in length. The output pulse produced by timer 820 as well as the output signal from AND gate 818 are applied to a flip-flop 824. Flip-flop 824 is configured to assert a high signal if, at the end of the period during which the wait pulse from timer 820 is asserted, the signal from AND gate 818 remains high. Thus, flip-flop 824 is configured to assert a high signal if, at the end of the wait period there is still an indication that the TRANS signal has not undergone a significant change.

The output signal produced by flip-flop is applied to an invertor 826 that produces the PRESSURE_FAULT signal. This, asserted low PRESSURE_FAULT signal is the signal that is applied to the motor controller 574, the inflow valve controller 576 and the outflow valve controller 578 to inhibit operation of these components when the system 30 is being operated in the normal mode and there is an indication of a potential fault in the pressure sensing components of the system.

The high pressure circuit 590, as seen in FIG. 31F, includes a comparator 830. The TRANS signals from the transducer 80 is applied to the noninverting input of comparator 830. A reference voltage from a voltage divider consisting of resistors 832 and 834 is applied to the inverting input of comparator 830. A pullup resistor 836 is tied between the +5 VDC voltage source and the output of comparator 830.

The PRESSURE_FAULT signal from the constant pressure detect circuit 586 as well as the output signal produced by comparator 830 of the high pressure circuit 590 are applied to a buzzer driver 840 integral with the alarm circuit 588. If either a potential fault in the pressure sensing circuit or a high fluid pressure at the surgical site is detected, buzzer driver 840 actuates a buzzer 842. Also part of the alarm circuit 588 but not illustrated are transistor switches that control the actuation of LEDs 554 so that the LEDs can provide a visual indication of the state of the system 30.

The fluid management pump system 30 of this invention is readied for use by simply snap-securing the cassette 52 integral with the tube set 34 to the control unit 50. There is no need to thread the inflow or outflow tubes 42 and 44, respectively, through valve units or pump devices or to make special fluid connections between the pressure sensing assembly 76 and the control unit 50 or to route the tubing around rollers and valves. Thus, the time, effort and dexterity required to ready this fluid management pump system 30 for use is kept to a minimum. This feature of the invention can be very useful if, once a surgical procedure has started, a need to change the tube set 34 arises. Such need may occur if during the procedure, the surgeon requires a tube set with a different set of characteristics to work on the patient or if for any reason the sterility of the tube set in use is called into question. Since all it takes is one release of the lock tongue 284 integral with the control unit 50 to remove the first step and a simple motion to install the replacement step, significant time is not spent during the surgical procedure replacing the tube set. Such time savings serves to facilitate the goal of minimizing the time the patient needs to be held under anesthesia.

Moreover, the ID contact 366 internal to the cassette 50 provides the control unit 50 with an indication of the type of tube set 34 being attached thereto as soon as the cassette is locked in place. Thus, the control unit can automatically configure itself for use with the tube set. This automatic configuration can include the presenting of an initial maximum fluid pressure at the surgical site and/or the presenting of the type of energization signals that need to be supplied to the pump 40 integral with the tube set 34. Since the cassette 52 carries this information internally, medical personnel do not have to spend any time configuring the control unit for use with the tube set. The elimination of this activity both helps minimize the time required to set up this fluid management pump system 30 for use and further eliminates the possibility that human error will result in the improper configuring of the control unit.

Still other advantages are associated with the pressure sensing cannula 46 of the fluid management pump system 30 of this invention. Owing to the axially offset relationship between the endoscope 90 and the surrounding cannula tube 86 it has been found that relatively significant quantities of solution can be introduced into the surgical site through the cannula tube. For example with a cannula tube 86 having an inside diameter of 0.192 inches, ±0.002 inches, in which an endoscope 90 having a main body 132 with a diameter of 0.157 inches, ±0.005 inches, it has been found that 1600 ml/min, ±200 ml/min of solution can be introduced into the surgical site with the aid of a pump that produces a force of 25 psi ±0.5 psi. Similarly owing to the axially off-center relationship between the cannula tube 86 and the outer sleeve 88, a relatively large volume of feedback fluid has been found to flow through the outer sleeve. The reason for this is that owing to the off-center relationship between the cannula tube 86 and the outer sleeve 88, there is relatively little surface tension in the center of the flow through conduit defined therebetween in comparison to conventional cannulae wherein the cannula tube and the outer sleeve are axially aligned. Thus while the cannula tube 86 has a conventional outside diameter of 0.203 inches, ±0.001 inches, and the inside diameter of the sleeve 88 is also conventional, 0.244 inches, ±0.002 inches, the fluid flow is relatively great in the crescent shaped space therebetween.

Moreover, all that is required to lock an endoscope 90 into the pressure sensing cannula 46 of this invention is to insert the endoscope 90 into the cannula until the cap lock 162 latches into the neck section 131 of the endoscope. The endoscope 90 is withdrawn by simply momentarily manually displacing the cap lock 162 so that it spaces from the neck section 131. Thus, only a minimal amount of time and attention are required to both lock an endoscope in this pressure sensing cannula 46 and remove it from the cannula.

The pump 40 of this invention is constructed so that the impeller 402 is connected directly to the shaft 396 of the motor 394. There are no intermediate gears. Consequently, when the pump 40 is actuated it generates only a minimal amount of noise.

Still other advantages are associated with the construction of the control unit. The heavy components internal to the control unit 50 are all mounted to the back wall of the shell 492. Thus, when this control unit 50 is mounted to an intravenous pole 498 its center of gravity is located in relatively close proximity to the pole. Moreover, as discussed above, whenever one of the buttons or switches 64–70 a downward force is exerted on the control unit 50. Collectively these features, help maintain the stability of the control unit when it is mounted to the intravenous pole.

Moreover, the pump 40 is designed so as to have two inlet ports 214. The provision of the twin inlet ports eliminates the need to provide an extra externa Y-connector when supply solution from multiple containers 36.

Still another feature of this invention, is that the air-water separator 234 performs two functions. A first function performed by the air water separator is that it functions as a microbial filter that prevents air borne contaminates from the air column used for fluid pressure sensing from reaching the interior of the control unit 50. Secondarily, the air-water separator 234 prevents liquid from pressure line inlet tube 78 from inadvertently reaching the control unit.

The control unit 50 of this invention is further arranged to block fluid flow through the inflow tube 42 unless the pump 40 is actuated. Thus, when the system is not supplying solution, backflow of possibly contaminated material from the surgical site to the pump is prevented It should be recognized that the foregoing description has been limited to a specific embodiment of the invention. It will be apparent, however, from the description of the invention that it can be practiced using alternative components other than what has been specifically described. For example, there is no need that the described pressure sensing cannula 46 always be used with this invention or that the cannula 46 only be used with this invention. Moreover, with regard to the pressure sensing cannula 46, it may be desirable to provide it with a cap different from the described cap 92 in order to facilitate its use with a different endoscope.

The tube set 34 may also have a different construction. For example, while one particular type of pump 40 has been described for use with the tube set, other pumps may be used as desired. In some versions of the invention, it may not even be required to provide a pump or have the pumps integrally attached to the tube set. Similarly, there is no requirement to always construct the tube set so that it includes a pressure sensing assembly with a dedicated set of tubing. In some versions of the invention, it may be desirable to design the tube set so that internal to the cassette there is a branch line attached to the outflow tube. This branch could be provided with some type of water-air barrier to present a air column that originates in the cassette to the control unit that has a pressure representative of liquid-state fluid pressure at the surgical site. An advantage of this arrangement is that it would eliminate some of the tubing and hardware associated with the dedicated pressure sensing assembly.

Furthermore, other types of tube sets can be provided to facilitate the use of the fluid management pump system 30 of this invention during surgical procedures other than endoscopic surgical procedures. It may, for example be desirable to provide lavage-only and/or suction irrigator only tube sets that can be used to facilitate the use of this system during general surgery. These tube sets would, in addison to having a inflow tube that is seated in a cassette might only have just a pump attached to the inflow tube. The tube sets designed to facilitate lavage fluid flow, which is pulsed fluid flow, would have valve associated with the inflow tube. The tube sets designed to perform suction irrigation, which is a continuous flow may not, in all circumstances require an inflow valve to regulate flow through the inflow tube. It should be recognized that each of the cassettes integral with these tube sets would have an ID contact or other data device that would provide an indication to the complementary control unit of the nature of the tube set. Based on the received data, the control unit would appropriately configure itself.

Moreover, while in the described versions of the invention, the valves that control fluid flow through the inflow and outflow tubes 42 and 44, respectively, are pinch valves. That need not always be the case. It may, for example, be desirable to provide some type of magnetically valve members. These valve members would then open and close based on the selective generation of localized magnetic fields generated by the control unit. Similarly, a back-flow valve could be employed as the inflow valve.

It similarly should be recognized that the control unit may have constructions different form what has been described. While one construction of the control unit out of a specific arrangement of analog signal processing components, timers and logic gates has been described, it should be clear that other constructions out of alternative discrete components may be provided. For example, in an alternative version of the invention the MOTOR_ENABLE signal may be used to both control the application of the energization signal to the pump 40 and the actuation of the solenoid 58 that regulates the open/closed actuation state of the inflow valve 54.

Figure 32:
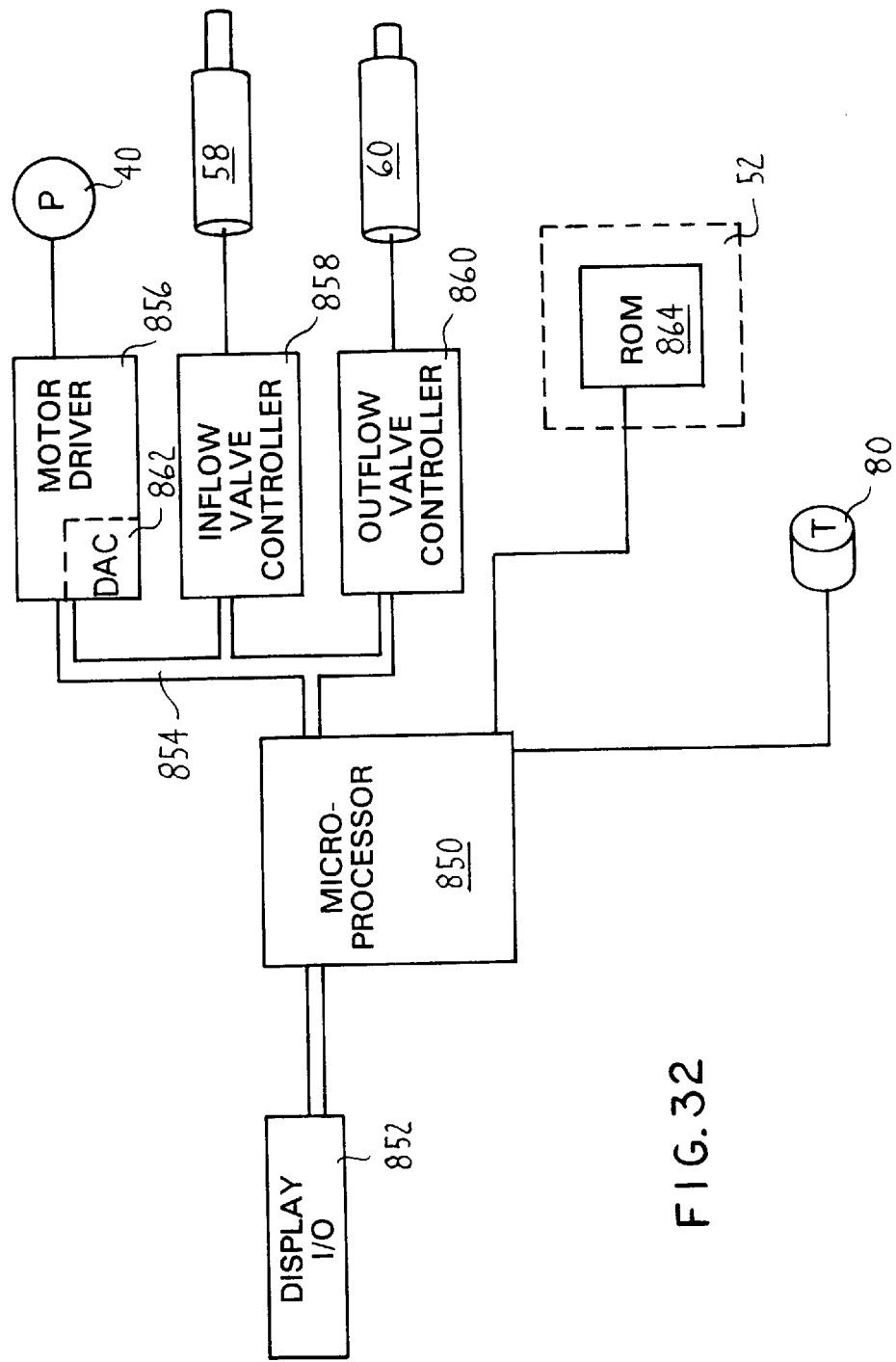
FIG. 32 is a block diagram of the basic components contented in one processor-controlled control unit of this invention.

Similarly, there is no requirement that the control unit include the control circuit formed of the described discrete components. FIG. 32 illustrates how the control unit may include a microprocessor 850 that provides the control signals that regulate the generation of the pump energization signals and the energization of the solenoids 58 and 60. In FIG. 32, the microprocessor is connected to receive the signals produced by the transducer 80, (internal analog-to-digital signal converter for the transducer signals in the microprocessor not shown.) The microprocessor 850 also causes buttons to be presented on a small touch screen display 852 attached to the front of the control unit 50.

Based on the signal from the transducer 80 and the commands entered over the touch screen display 852, microprocessor 850 generates instructions over a data bus 854. These instructions are selectively acted upon by a motor driver 856, an inflow valve controller 858 and a outflow valve controller 860, each of which is connected to bus 854. Motor driver 856, inflow valve controller 858 and outflow valve controller 860 each act on the specific instructions there are sent. As part of the instruction processing, it may necessary to convert at least a portions of the instructions into analog signals, (only the digital-to-analog converter 862 internal to the motor driver 854 is shown.) In this manner the motor driver 854 causes the appropriate energization signals to be sent to the pump 40, and the inflow valve controller 858 and 860 cause the appropriate energization signals to be sent to the solenoids 58 and 60, respectively.

It should be seen that in the fluid management pump system depicted in FIG. 32 that the cassette 52 is provided with a read only memory 864. Memory 864 is used to provided detailed information about the tube set 34 with which the cassette 52 is integral. For example, the memory 864 can provide basic information regarding whether or not the tube set is a large joint tube set, a small joint tube set, a lavage only tube set or a suction irrigation-only tube set. The microprocessor 850 can then use this information to determine if it should monitor the signals produced by the transducer and which of the solenoids 58 and 60 should be actuated.

Memory 864 can also be used to provided more detailed information about the components forming the tube set 34. For example, the memory 864 can provide data regarding the nature of the pump and or the structure of the valves. Microprocessor 850, upon can retrieve this data and use this data to determine the commands it should generate in order to cause the motor driver 856 to generate the appropriate energization signals for the particular pump. Similarly, microprocessor 850 can used the retrieved data to determine the magnitude of the solenoid energization currents that should be generated and the periods of time for which these currents should be generated. Thus, the tube sets can be provided with pumps 40 and valves that require the generation of different signals for their actuation.

In a similar manner, microprocessor 850 can use the data contained in the memory 864 to determine what buttons should be presented on the touch screen display 852. For example, if the memory 864 indicates the tube set 34 is a lavage-only tube set, microprocessor 850 is programmed to only present lavage buttons on the display 852; touch screen buttons that allow the setting of surgical site pressure will not be presented.

One suitable memory that can be employed as the cassette memory 864 is a DS2505P write-once NOVRAM manufactured by Dallas Semiconductor. This NOVRAM is well suited for instillation in the cassette 52 as data is read serially therefrom, this eliminates the need to provide a parallel signal connector between the control unit 50 and the cassette. One microprocessor that can be used to retrieve the data from the cassette in serial form is the 80C552 manufactured by Phillips Semiconductor.

Alternatively an electronically erasable memory such as a Dallas Semiconductor DS2430AP can be employed as the memory 864 internal to the cassette 52. This memory can be written to by the microprocessor 850 internal to the control unit 50. During the operation of the system 30, the control unit can write into the memory 864 data indicating that the tube set with which the memory is associated has been used.

This data can, for example take the form of a date-and-time stamp. Then, during any subsequencies uses of the tube set, the microprocessor 850 can initially read this data field to determine if the tube set was previously used. If a previously use of a single use tube set is detected, the microprocessor can display a warning notice on the display 852 and/or be configured to inhibit the generation of the energization signals that would allow the later uses of the tube set.

It should also be recognized that it may be desirable to, in some versions of the invention to install a flow meters in the cassette to monitor fluid flow through the inflow and outflow tubes. These flow meters may be desirable if, for a particular surgical procedure it is desirable to quantitatively monitor the volume of solution applied to a surgical site or drained from a surgical site.

Therefore it is an object of the appended claims to cover all such modifications as come within the true spirit and scope of this invention.

The embodiments of the invention in which an exclusive property or privilege is claimed are defined as follows:

1. A fluid management pump system for supplying a liquid-state fluid from a container to a surgical site, said fluid management pump system including:
   a tube set, said tube set including:
      a cassette, said cassette having a back panel, a front panel spaced from said back panel and a coupling member;
      an inflow tube for providing a conduit for the fluid from the container to the surgical site, said inflow tube extending through said cassette;
      an outflow tube for providing a conduit through which fluid is drained from the surgical site, said outflow tube extending through said cassette;
      first and second fluid control valves attached to said cassette, wherein: said first fluid control valve is associated with said inflow tube for regulating fluid flow therethrough; and said second fluid control valve is associated with said outflow control valve for regulating fluid flow therethrough; and
      a pressure feedback assembly attached to said cassette and in fluid communication with the surgical site for forming a variable-pressure air column that is representative of liquid fluid pressure at the surgical site, said pressure feedback assembly having a port through which the variable-pressure air column is directed outwardly from the back panel of the cassette and a seal disposed around said port;
   an electrically actuatable pump connected between the container and said inflow tube of said tube set for forcing fluid from the container through said inflow tube, said pump being actuated in response to the application of an energization signal thereto; and
   a control unit, said control unit including:
      a housing, said housing having a surface against which said back panel of said cassette is positioned and including a locking mechanism for releasably securing said cassette to said housing;
      a pressure sensing assembly disposed in said housing, said pressure sensing assembly including a conduit disposed in said housing, said conduit having an opening in said surface of said housing against which said cassette is seated and positioned to be aligned with said port of said pressure feedback assembly so that the variable-pressure column flows into said conduit of said pressure sensing assembly and a pressure transducer in said conduit of said pressure sensing assembly, said pressure transducer being configured to generate a sensed-pressure signal representative of the pressure of the variable-pressure air column;
      first and second valve controllers mounted in said housing positioned to be adjacent said surface of said housing against which said cassette is seated, said first valve controller being positioned to open/close said first control valve of said tube set in response to a inflow control signal so as to control fluid flow through said inflow tube, and said second valve controller being positioned to open/close said second control valve of said tube set in response to an outflow control signal so as to control fluid flow through said outflow tube; and
   a pump controller disposed in said housing, said pump controller being connected to receive operator generated commands and said sensed-pressure signal, to generate said energization signal to said pump, to generate said inflow and outflow control signals to said first and second valve controllers and being configured to control the open/closed states of said first and second control valves in response to the operator-generated commands and said sensed-pressure signal.

2. The fluid management pump system of claim 1, wherein: said control unit is provided with a set of contacts on said surface of said housing to which the energization signals for said pump are applied; said cassette is provided with a set of contacts that extend from said back panel of said cassette that are designed to electrical connect to said contacts on said housing to which the energization signals for said pump are applied; and said pump is connected to said cassette of said tube set by a set of conductors that extend from said contacts on said cassette so that the said energization signals are applied to said pump over said conductors.

3. The fluid management pump system of claim 1, wherein said pump controller is configured to generate said inflow control signal so as to block fluid flow through said inflow tube of said tube set when said energization signals are not applied to said pump.

4. The fluid management pump of claim 1, wherein:
   said first and second fluid control valves each including a valve arm that is pivotally attached to said cassette and that is normally biased to be in a first state for regulating fluid flow through said tube which said valve is associated; and
   said first and second valve controllers each include an electrically actuated plunger designed to selectively displace said valve arm of said fluid control valve with which said valve controller is actuated so that the actuation of said plunger causes the displacement of said valve arm.

5. The fluid management pump of claim 4, wherein: said valve arms of said first and second fluid control valves are biased to normally allow fluid flow through said inlet tube and said outflow tube; and said electrically actuated plungers of said first and second valve controllers are configured to be selectively extended outside of said housing of said control unit so that when each said plunger is so extended said plunger displaces said valve arm with which said plunger is associated so as to block fluid flow through said tube with which said valve arm is associated.

6. The fluid management system of claim 5, wherein said electrically actuated plunger of said first valve controller is normally in an extended state so as to normally maintain said first fluid control valve in the closed state.

7. The fluid management pump system of claim 1, wherein said pressure feedback assembly of said tube set includes: a pressure sensing line that is in fluid communication with the surgical site, said pressure sensing line being constructed so that a column of liquid from the surgical site has a head in said pressure sensing line so that the base of the variable-pressure air column is adjacent the head of the water column; and an air column line connected between said pressure sensing line and said cassette through which the variable-pressure air column is applied to said control unit.

8. The fluid management system of claim 1, wherein said first valve controller and said second valve controller each include a selectively movable member that extends outside of said housing of said pump control unit for contacting said fluid control valve with which said valve controller is associated for regulating the open/closed state of said fluid control valve.

9. A tube set for use with a control unit to supply fluid from a container to a surgical site, said tube set including:
   a cassette, said cassette having a coupling member for attaching said cassette to the control unit;
   an inflow tube for providing a conduit for the fluid from the container to the surgical site, said inflow tube extending through said cassette;
   an outflow tube for providing a conduit through which fluid is drained from the surgical site, said outflow tube extending through said cassette;
   a pressure feedback tube attached to said cassette for providing a conduit through which fluid representative of fluid pressure at the surgical site is applied to the control unit;
   first and second fluid control valves attached to said cassette, wherein: said first fluid control valve is associated with said inflow tube for regulating fluid flow therethrough; said second fluid control valve is associated with said outflow control valve for regulating fluid flow therethrough; and both said first and second control valves are open/closed by separate actuating members integral with the control unit;
   a feedback conduit integral with said cassette for providing a fluid communication path between said pressure feedback tube and the control unit, said feedback conduit having an opening directed towards the control unit; and
   a seal attached to said cassette around said opening of said feedback conduit so as to provide a fluid tight barrier between the control unit and said cassette around said opening of said feedback conduit.

10. The tube set of claim 9, wherein: said cassette is formed to have a back panel that is disposed against the control unit and a front panel that is spaced from said back panel so as to be spaced away from the control unit; and said first fluid control valve and said second fluid control valve each include a cantilever arm that is pivotally attached to said back panel of said cassette, whereby said cantilever arms are selectively displaced by the actuating members integral with the control unit for controlling the open/closed state of said fluid control valves with which said cantilever arms are associated.

11. The tube set of claim 10, wherein said cantilever arms of said first and second fluid control valves are integrally formed with said back panel of said cassette housing so as to form portions of said back panel of said cassette.

12. The tube set of claim 9, further including: an electrically driven pump connected to said inflow tube for forcing fluid from the container through said inflow tube; a set of terminals attached to said cassette, said terminals being positioned to contact complementary terminals on the control unit so that a commutation current can be applied to said terminals on said cassette; and a set of conductors extending from said terminals on said cassette to said pump for providing a conductive path for the commutation current from said terminals attached to said cassette to said pump.

13. The tube set of claim 12, wherein said pump includes a motor with a rotating shaft and an impeller that is connected directly to said rotating shaft of said motor for providing a motive force to displace the fluid.

14. The tube set of claim 9, wherein said pressure feedback tube includes: a first tube section connected to receive liquid-state fluid from the surgical site, said first tube section being formed of a hydrophobic material so that a liquid column forms in said first tube section; and a second tube section connected to an end of said first tube section distal from the surgical site and to said cassette so that a variable-pressure air column is located in said second tube and said variable pressure air column is presented to the control unit through said opening of said feedback conduit integral with said cassette.

15. The tube set of claim 14, wherein: a portion of said first tube section of said pressure feedback tube is formed as a helical winding; and said inflow tube or said outflow tube extends through said helical winding of said first tube section of said pressure feedback tube.

16. The tube set of claim 14, further including an air-water separator located between said first tube section of said pressure feedback tube and said second section of said pressure feedback tube, said air-water separator including a member for prohibiting liquid flow from said first tube section to said second tube section.

17. The tube set of claim 9, wherein said pressure feedback tube is formed to have at least one section thereof that is in the form of a helical winding and said inflow tube or said outflow tube extends through said helical winding of said pressure feedback tube.

18. The tube set of claim 9, further including: an electrically conductive member disposed in said cassette for providing at least one signal identifying characteristics of said tube set; and a set of contacts mounted on said cassette and providing electrical paths from the control unit to said at least one electrically conductive member.

19. The tube set of claim 18, wherein said electrically conductive member comprises a conductive strip that extends between said contacts with which said conductive member is associated.

20. The tube set of claim 18, wherein said electrically conductive member comprises a memory disposed in said cassette, said memory containing data that describes characteristics of said tube set.

21. The tube set of claim 9, wherein: said inflow tube includes a section of tube that extends from outside said cassette, through said cassette and outwardly through said cassette; and said first fluid control valve includes a valve member that selectively compresses said section of said of inflow tube disposed inside cassette so as to regulate fluid flow through said inflow tube.

22. The tube set of claim 9, wherein: said outflow tube includes a section of tube that extends from outside said cassette, through said cassette and outwardly through said cassette; and said second fluid control valve includes a valve member that selectively compresses said section of said of outflow tube disposed inside said cassette so as to regulate fluid flow through said outflow tube.

23. A control unit for a fluid management pump system, the fluid management pump system including a tube set that includes: a cassette; an inflow tube that is connected to the cassette; an outflow tube that is connected to the cassette; a pump connected to the inflow tube to force solution through the inflow tube and connected to the cassette to receive energization signals therefrom; a first control valve mounted in the cassette for controlling solution flow through the inflow tube; a second control valve mounted in the cassette for controlling flow through the outflow tube; and an ID member in the cassette for storing data regarding the pump, said control unit including:

a housing, said housing having a surface against which a back panel of the cassette is positioned and including a locking mechanism for releasably securing the cassette to said housing;

first and second valve controllers mounted in said housing positioned to be adjacent said surface of said housing against which the cassette is seated, said first valve controller being positioned to open/close the first control valve of said tube set in response to an inflow control signal so as to control fluid flow through the inflow tube, and said second valve controller being positioned to open/close the second control valve of the tube set in response to an outflow control signal so as to control fluid flow through the outflow tube; and a pump controller disposed in said housing, said pump controller being connected to receive operator generated commands and to read the ID member in the cassette and being configured to generate energization signals to the pump through the cassette and to generate said inflow and outflow control signals to said first and second valve controllers and being configured to selectively generate energization signal to said pump and to control the open/closed states of said first and second control valves in response to the operator-generated commands and the data contained in the ID member.

24. A pressure sensing cannula for a fluid management system for receiving an endoscope with an elongated main body, said pressure sensing cannula including:

a cannula body with opposed ends and a bore for extending between said opposed ends for receiving the endoscope;

an elongated cannula tube extending from one end of said cannula body, said cannula tube having a bore extending therethrough that is in communication with said bore of said main body so that said main body of the endoscope can extend through said cannula bore, said bore being centered around an elongated cannula tube axis; and wherein said cannula body is formed to have a socket at said end opposite said end from which said cannula tube extends for receiving the endoscope, said cannula body being formed so that said socket is axially offset from said axis of said cannula tube so that when the endoscope is seated in said bore of cannula tube, the main body of the endoscope is axially offset from said axis of said cannula tube.

* * * * *